US010985325B2

United States Patent
Kato et al.

(10) Patent No.: US 10,985,325 B2
(45) Date of Patent: Apr. 20, 2021

(54) AROMATIC AMINE DERIVATIVE, AND ORGANIC ELECTROLUMINESCENT ELEMENT USING SAME

(71) Applicant: IDEMITSU KOSAN CO., LTD., Chiyoda-ku (JP)

(72) Inventors: Tomoki Kato, Ichihara (JP); Takayasu Sado, Urayasu (JP); Takahiro Fujiyama, Kisarazu (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 168 days.

(21) Appl. No.: 14/424,703

(22) PCT Filed: Aug. 29, 2013

(86) PCT No.: PCT/JP2013/073183
§ 371 (c)(1),
(2) Date: Feb. 27, 2015

(87) PCT Pub. No.: WO2014/034793
PCT Pub. Date: Mar. 6, 2014

(65) Prior Publication Data
US 2015/0263292 A1   Sep. 17, 2015

(30) Foreign Application Priority Data

Aug. 30, 2012   (JP) .............................. 2012-190598

(51) Int. Cl.
*H01L 51/00*   (2006.01)
*H01L 51/50*   (2006.01)
(Continued)

(52) U.S. Cl.
CPC ........ *H01L 51/0061* (2013.01); *C07D 307/91* (2013.01); *C07D 333/76* (2013.01); *C07D 405/12* (2013.01); *C07D 409/12* (2013.01); *C09B 57/00* (2013.01); *C09B 57/008* (2013.01); *C09K 11/06* (2013.01); *H01L 51/006* (2013.01); *H01L 51/0054* (2013.01); *H01L 51/0072* (2013.01); *H01L 51/0073* (2013.01); *H01L 51/0074* (2013.01); *C09K 2211/1007* (2013.01); *C09K 2211/1011* (2013.01); *C09K 2211/1014* (2013.01); *C09K 2211/1044* (2013.01); *C09K 2211/1088* (2013.01); *C09K 2211/1092* (2013.01); *H01L 51/0058* (2013.01);
(Continued)

(58) Field of Classification Search
CPC .. C07D 307/91; C07D 333/76; C07D 405/12; C07D 409/12; C07D 407/12; C07D 407/10; C09K 11/06; C09K 2211/1007; C09K 2211/1011; C09K 2211/1014; C09K 2211/1088; C09K 2211/1092; C09K 2211/1044; C09K 2211/301; C09K 2211/308; H01L 51/0054; H01L 51/0058; H01L 51/006; H01L 51/0061; H01L 51/0073; H01L 51/0072; H01L 51/0074; H01L 51/5016; H01L 51/5056; H01L 51/5064; H01L 51/5088; H01L 51/5206; H01L 51/5221; H01L 51/5231; H01L 51/0059; H01L 51/5048; H01L 51/5052; H01L 51/506; C09B 57/00; C09B 57/008
USPC ....... 549/43, 460; 428/690, 917, 336, 411.4, 428/691; 313/500–512; 257/40, 88–104, 257/E51.001–E51.052; 427/58, 66; 252/301.16–301.35
See application file for complete search history.

(56) References Cited

U.S. PATENT DOCUMENTS 7,431,997 B2   10/2008   Hwang et al.
7,737,627 B2   6/2010   Hwang et al.
(Continued)

FOREIGN PATENT DOCUMENTS

CN   101432272 A   5/2009
EP   2 175 005 A1   4/2010
(Continued)

OTHER PUBLICATIONS

Combined Office Action and Search Report dated Jan. 12, 2016 in Chinese Patent Application No. 201380045222.9 (with English translation of category of cited documents).
(Continued)

*Primary Examiner* — Dylan C Kershner
*Assistant Examiner* — Elizabeth M. Dahlburg
(74) *Attorney, Agent, or Firm* — Oblon, McClelland, Maier & Neustadt, L.L.P.

(57) ABSTRACT

An aromatic amine derivative represented by formula (1):

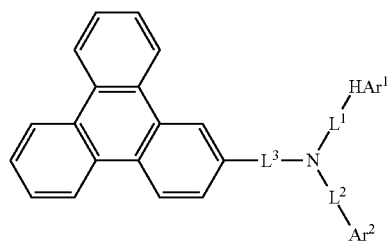

wherein $HAr^1$, $Ar^2$, $L^1$, $L^2$, and $L^3$ are as defined in the specification, is useful as a material for constituting an organic EL device and realizes an organic EL device having a high efficiency and a long lifetime even when driving at a low voltage.

16 Claims, No Drawings

(51) Int. Cl.
  *C07D 307/91* (2006.01)
  *C07D 409/12* (2006.01)
  *C09K 11/06* (2006.01)
  *C07D 333/76* (2006.01)
  *C09B 57/00* (2006.01)
  *C07D 405/12* (2006.01)
  *H01L 51/52* (2006.01)

(52) U.S. Cl.
  CPC ...... *H01L 51/0085* (2013.01); *H01L 51/5016* (2013.01); *H01L 51/5056* (2013.01); *H01L 51/5064* (2013.01); *H01L 51/5088* (2013.01); *H01L 51/5206* (2013.01); *H01L 51/5221* (2013.01); *H01L 51/5231* (2013.01); *H01L 2251/301* (2013.01); *H01L 2251/308* (2013.01)

(56) References Cited

U.S. PATENT DOCUMENTS

| | | | |
|---|---|---|---|
| 8,021,764 | B2 | 9/2011 | Hwang et al. |
| 8,021,765 | B2 | 9/2011 | Hwang et al. |
| 8,188,315 | B2 | 5/2012 | Hwang et al. |
| 8,974,922 | B2 | 3/2015 | Hwang et al. |
| 9,478,745 | B2 | 10/2016 | Hwang et al. |
| 2005/0221124 | A1 | 10/2005 | Hwang et al. |
| 2006/0020136 | A1 | 1/2006 | Hwang et al. |
| 2006/0115680 | A1 | 6/2006 | Hwang et al. |
| 2007/0215889 | A1 | 9/2007 | Kawakami et al. |
| 2007/0231503 | A1 | 10/2007 | Hwang et al. |
| 2007/0278938 | A1 | 12/2007 | Yabunouchi et al. |
| 2008/0107919 | A1 | 5/2008 | Hwang et al. |
| 2010/0108997 | A1 | 5/2010 | Kim et al. |
| 2012/0091887 | A1* | 4/2012 | Osaka ............... C07D 405/04 313/504 |
| 2012/0157694 | A1* | 6/2012 | Osaka ............... C07F 5/025 549/43 |
| 2012/0211733 | A1 | 8/2012 | Hwang et al. |
| 2012/0211743 | A1 | 8/2012 | Ito et al. |
| 2012/0326137 | A1* | 12/2012 | Song ............... H01L 51/5064 257/40 |
| 2013/0207092 | A1 | 8/2013 | Huh et al. |
| 2013/0256649 | A1* | 10/2013 | Huh ............... C09K 11/06 257/40 |
| 2015/0221872 | A1 | 8/2015 | Hwang et al. |
| 2017/0005273 | A1 | 1/2017 | Hwang et al. |

FOREIGN PATENT DOCUMENTS

| | | |
|---|---|---|
| JP | 2005/290000 | 10/2005 |
| JP | B-6367117 | 7/2018 |
| KR | 2012-0030793 | 3/2012 |
| KR | 2012-0076314 | 7/2012 |
| WO | 2007/148660 | 12/2007 |
| WO | 2008/062636 | 5/2008 |
| WO | 2011/021520 | 2/2011 |
| WO | WO 2011/126224 A1 | 10/2011 |
| WO | 2012/039534 | 3/2012 |
| WO | 2012/091428 | 7/2012 |
| WO | 2013/055132 | 4/2013 |
| WO | 2013/061805 | 5/2013 |

OTHER PUBLICATIONS

International Search Report dated Oct. 22, 2013 in PCT/JP13/073183 Filed Aug. 29, 2013.
Extended Search Report dated Mar. 22, 2016 in European Patent Application No. 13832674.9.
Taiwanese office action in Application 106136814 dated Oct. 1, 2018.
Extended European Search Report dated Mar. 28, 2018 in European Patent Application 17198969.2.
Japanese Office Action in corresponding patent application No. 2017-195220, dated Aug. 7, 2018. (w/English Translation).
Combined Office Action and Search Report dated Jul. 1, 2019 in Chinese Patent Application No. 201710648042.X with unedited computer generated English translation of the Office Action and English translation of category of cited documents.
Office Action in Korean Application No. 10-2015-7005239, dated Feb. 11, 2020 (w/English Translation).

* cited by examiner

AROMATIC AMINE DERIVATIVE, AND ORGANIC ELECTROLUMINESCENT ELEMENT USING SAME

TECHNICAL FIELD

The present invention relates to aromatic amine derivatives and organic electroluminescence devices using the aromatic amine derivatives. For example, the present invention relates to aromatic amine derivatives having a triphenylene skeleton and one or both of a dibenzofuran skeleton and a dibenzothiophene skeleton and organic electroluminescence devices employing the aromatic amine derivative.

BACKGROUND ART

Generally, an organic electroluminescence (EL) device includes an anode, a cathode, and at least one organic thin film layer interposed between the anode and the cathode. When applying a voltage between both electrodes, electrons are injected into an emission region from the cathode side and holes are injected into the emission region from the anode side. The injected electrons and holes are recombined in the emission region to generate an excited state. When the excited state returns to a ground state, light is emitted. Therefore, to obtain a high-efficiency organic EL device, it is important to develop a compound which efficiently transports electrons or holes into an emission region and facilitates the recombination of electron and hole.

Generally, when driving or storing an organic EL device in a high-temperature environment, various problems occur, for example, the emission color is changed, the emission efficiency is reduced, the driving voltage is increased, and the emission life is shortened. To eliminate these drawbacks, various hole transporting materials have been proposed, for example, Patent Document 1 discloses an aromatic amine derivative in which a N-carbazolyl group is directly bonded to a 9,9-diphenylfluorene skeleton, Patent Document 2 discloses an aromatic amine derivative in which a 3-carbazolyl group is directly bonded to a 9,9-dimethylfluorene skeleton, Patent Document 3 discloses an aromatic amine derivative in which a N-carbazolylphenyl group is bonded to a 9,9-diphenylfluorene skeleton via a nitrogen atom, and Patent Document 4 discloses an aromatic amine derivative in which a 3-carbazolyl group is bonded to a 9,9-diphenylfluorene skeleton via a nitrogen atom. Patent Document 5 describes an aromatic amine derivative which includes a skeleton selected from a fluorene skeleton, a carbazole skeleton, a dibenzofuran skeleton, and a dibenzothiophene skeleton.

However, the aromatic amine derivatives disclosed in Patent Documents 1 to 5 are still insufficient for reducing the driving voltage, improving the efficiency at low-voltage driving, and prolonging the lifetime. Therefore, a further improvement has been required.

Patent Document 6 describes an aromatic amine compound having a triphenylene skeleton and a dibenzofuran skeleton (or a dibenzothiophene skeleton). Many of the exemplary compounds thereof must have a carbazole skeleton or a terminal diarylamino group as an essential structure. Patent Document 6 further describes the following compounds.

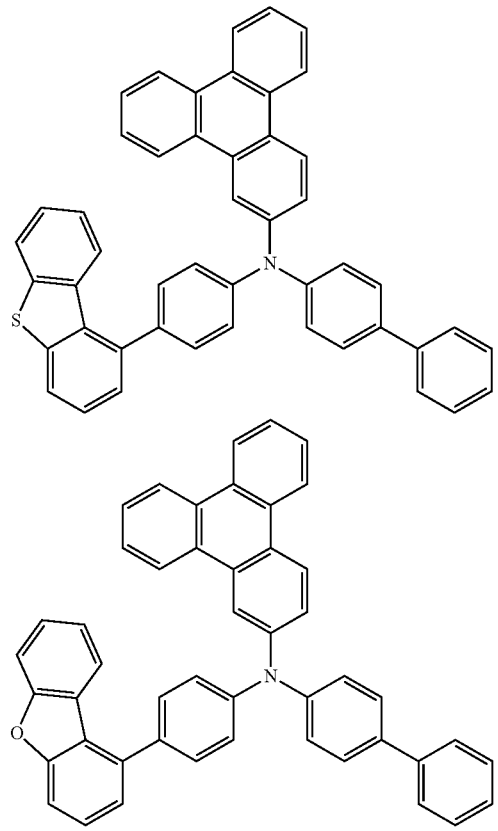

The above compounds have a 1-dibenzothiophenyl group or a 1-dibenzofuranyl group. Since these groups are less effective for improving the efficiency and the lifetime, the above amine compounds having a 1-dibenzothiophenyl group or a 1-dibenzofuranyl group are poor in the efficiency and the lifetime.

Therefore, it has been required to develop a material for an organic EL device, particularly a hole transporting material, which realizes an organic EL device exhibiting a high efficiency even at a low-voltage driving and having a long lifetime.

CITATION LIST

Patent Documents

Patent Document 1: WO 07/148660
Patent Document 2: WO 08/062636
Patent Document 3: US 2007/0215889A
Patent Document 4: JP 2005-290000A
Patent Document 5: WO 2011/021520
Patent Document 6: WO 2012/039534

SUMMARY OF THE INVENTION

Problems to be Solved by the Invention

The present invention has been made in view of solving the above problems and an object of the invention is to provide a material for an organic EL device, for example, a hole transporting material, which realizes a long-lifetime, high-efficiency organic EL device capable of driving at a low voltage.

Means for Solving the Problems

As a result of extensive research in view of achieving the above object, the inventors have found that a compound having a triphenylene skeleton and a nitrogen atom to which one or both of a 2- or 4-dibenzofuranyl group and a 2- or 4-dibenzothiophenyl group are bonded directly or via a linker is excellent in the hole injecting ability and a hole transporting ability, and further found that such a compound realizes an organic EL device capable of driving a low voltage and having a long lifetime and a high efficiency.

Namely, the present invention provides an aromatic amine derivative represented by formula (1):

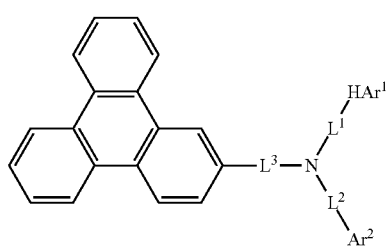

(1)

wherein $HAr^1$ represents a group selected from formulae (2) to (5):

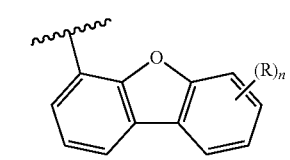

(2)

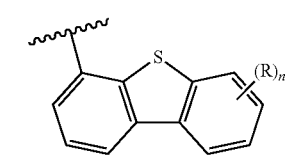

(3)

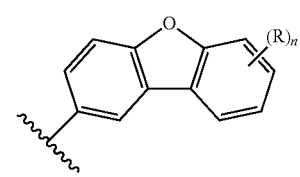

(4)

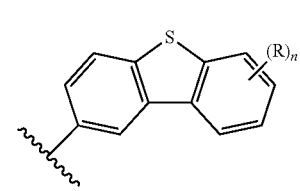

(5)

in formulae (2) to (5), n represents an integer of 0 to 4; and each R independently represents a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, when more than one R is present, the groups R may be the same or different;

$L^1$ to $L^3$ may be the same or different and each independently represents a single bond, a group represented by formula (6), or a group represented by formula (7):

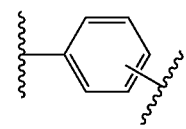

(6)

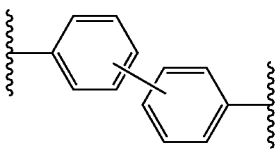

(7)

$Ar^2$ represents a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 carbon atoms, or a group selected from formulae (8) to (11), provided that $Ar^2$ does not include a carbazole skeleton and a substituted or unsubstituted amino group:

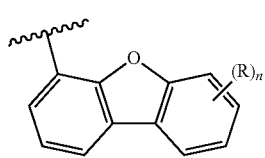

(8)

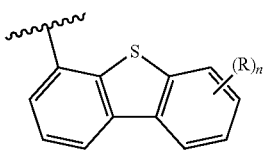

(9)

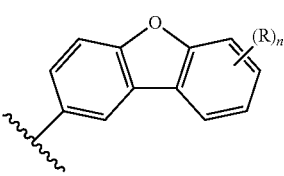

(10)

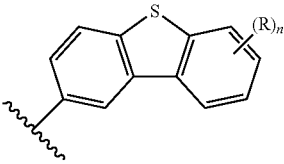

(11)

in formulae (8) to (11), n represents an integer of 0 to 4; and each R independently represents a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, when more than one R is present, the groups R may be the same or different.

The present invention further provides an organic electroluminescence device comprising an anode, a cathode, and at least one organic thin film layer between the anode and the cathode, wherein the at least one organic thin film layer comprises a light emitting layer and at least one layer of the organic thin film layer comprises the aromatic amine derivative represented by formula (1).

Effects of the Invention

By using the aromatic amine derivative of the invention, a long-lifetime, high-efficiency organic EL device capable of driving at a low voltage is obtained.

MODE FOR CARRYING OUT THE INVENTION

The term of "a to b carbon atoms" referred to by "a substituted or unsubstituted X group having a to b carbon atoms" used herein is the number of carbon atoms of the unsubstituted X group and does not include any carbon atom in the substituent of the substituted X group.

The definition of "hydrogen atom" used herein includes isotopes different in the neutron numbers, i.e., light hydrogen (protium), heavy hydrogen (deuterium), and tritium.

The optional substituent referred to by "substituted or unsubstituted" used herein is selected from the group consisting of an alkyl group having 1 to 50, preferably 1 to 10, more preferably 1 to 5 carbon atoms; a cycloalkyl group having 3 to 50, preferably 3 to 6, more preferably 5 or 6 ring carbon atoms; an aryl group having 6 to 50, preferably 6 to 24, more preferably 6 to 12 ring carbon atoms; an aralkyl group having 1 to 50, preferably 1 to 10, more preferably 1 to 5 carbon atoms which includes an aryl group having 6 to 50, preferably 6 to 24, more preferably 6 to 12 ring carbon atoms; an amino group; a mono- or dialkylamino group having an alkyl group having 1 to 50, preferably 1 to 10, more preferably 1 to 5 carbon atoms; a mono- or diarylamino group having an aryl group having 6 to 50, preferably 6 to 24, more preferably 6 to 12 ring carbon atoms; an alkoxy group having an alkyl group having 1 to 50, preferably 1 to 10, more preferably 1 to 5 carbon atoms; an aryloxy group having an aryl group having 6 to 50, preferably 6 to 24, more preferably 6 to 12 ring carbon atoms; a mono-, di- or tri-substituted silyl group having a substituent selected from an alkyl group having 1 to 50, preferably 1 to 10, more preferably 1 to 5 carbon atoms and an aryl group having 6 to 50, preferably 6 to 24, more preferably 6 to 12 ring carbon atoms; a heteroaryl group having 5 to 50, preferably 5 to 24, more preferably 5 to 12 ring atoms and having 1 to 5, preferably 1 to 3, more preferably 1 to 2 hetero atoms, such as a nitrogen atom, an oxygen atom and a sulfur atom; a halogen atom selected from a fluorine atom, a chlorine atom, a bromine atom and an iodine atom; a cyano group; and a nitro group.

The aromatic amine derivative of the invention comprises a triphenylene skeleton and is represented by formula (1):

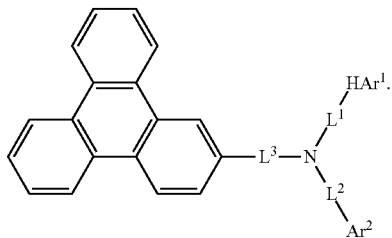

Since the triphenylene skeleton is highly planar, the molecules of the aromatic amine derivative are closely aligned together in a thin film to provide a thin film with a good orientation, this reducing the driving voltage. In addition, since the triphenylene skeleton increases the glass transition point (Tg), the aromatic amine derivative has a high Tg and is stable, thereby prolonging the lifetime of an organic EL device.

In formula (1), $HAr^1$ represents a group selected from formulae (2) to (5):

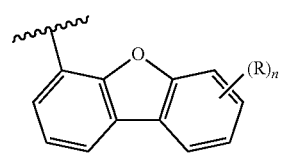

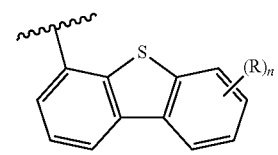

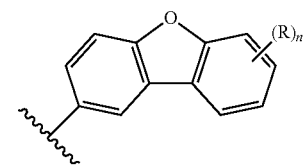

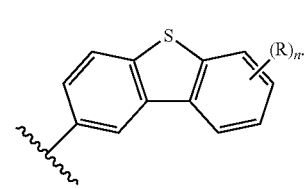

When $HAr^1$ is a group represented by formula (2) or (3), a long lifetime is expected, and a high efficiency is expected when $HAr^1$ is a group represented by formula (4) or (5).

In formulae (2) to (5), n represents an integer of 0 to 4, preferably an integer of 0 to 2, and particularly preferably 0, wherein n=0 means the absence of the substituent R.

Each R independently represents a substituted or unsubstituted alkyl group having 1 to 20, preferably 1 to 5, and more preferably 1 to 4 carbon atoms, a substituted or unsubstituted aryl group having 6 to 50, preferably 6 to 24, and more preferably 6 to 18 ring carbon atoms, a substituted or unsubstituted heterocyclic group having 3 to 50, preferably 3 to 24, and more preferably 3 to 18 ring atoms, a halogen atom, a substituted or unsubstituted fluoroalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted fluoroalkoxy group having 1 to 20, preferably 1 to 5, and more preferably 1 to 4 carbon atoms, a substituted or unsubstituted aryloxy group having 6 to 50, preferably 6 to 24, and more preferably 6 to 18 ring carbon atoms, or a cyano group. When more than one R is present, the groups R may be the same or different.

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). Preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group and a t-butyl group being particularly preferred.

Examples of the aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an as-indacenyl group, a fluoranthenyl group, and a perylenyl group. Preferred are a phenyl group, a naphthylphenyl group, a biphenylyl group, a terphenylyl group, a naphthyl group, and a 9,9-dimethylfluorenyl group, with a phenyl group, a biphenylyl group, a naphthyl group, and a 9,9-dimethylfluorenyl group being more preferred, and a phenyl group being particularly preferred.

The heterocyclic group having 3 to 50 ring atoms includes at least one, preferably 1 to 2 hetero atoms, for example, a nitrogen atom, a sulfur atom, and an oxygen atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group. Preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group. More preferred are a benzofuranyl group, a benzothiophenyl group, a dibenzofuranyl group, and a dibenzothiophenyl group.

Examples of the halogen atom include a fluorine atom, a chlorine atom, a bromine atom and an iodine atom, with a fluorine atom being particularly preferred.

Examples of the fluoroalkyl group having 1 to 20 carbon atoms include a group obtained by substituting a fluorine atom for at least one hydrogen atom, preferably 1 to 7 hydrogen atom of the alkyl group having 1 to 20 carbon atoms mentioned above, and preferably a heptafluoropropyl group, a pentafluoroethyl group, a 2,2,2-trifluoroethyl group, and a trifluoromethyl group, more preferably a pentafluoroethyl group, a 2,2,2-trifluoroethyl group, and a trifluoromethyl group, and particularly preferably a trifluoromethyl group.

Examples of the alkoxy group having 1 to 20 carbon atoms are represented by —OR$^{10}$, wherein R$^{10}$ represents the alkyl group having 1 to 20 carbon atoms mentioned above, and preferably a t-butoxy group, a propoxy group, an ethoxy group and a methoxy group, more preferably an ethoxy group and a methoxy group, and particularly preferably a methoxy group.

Examples of the fluoroalkoxy group having 1 to 20 carbon atoms are represented by —OR$^{11}$, wherein R$^{11}$ represents the fluoroalkyl group having 1 to 20 carbon atoms mentioned above, and preferably a heptafluoropropoxy group, a pentafluoroethoxy group, a 2,2,2-trifluoroethoxy group, and a trifluoromethoxy group, more preferably a pentafluoroethoxy group, a 2,2,2-trifluoroethoxy group, and a trifluoromethoxy group, and particularly preferably a trifluoromethoxy group.

The aryloxy group having 6 to 50 ring carbon atoms is represented by —OR$^{12}$, wherein R$^{12}$ represents the aryl group having 6 to 50 ring carbon atoms mentioned above, preferably a terphenyl group, a biphenyl group and a phenyl group, more preferably a biphenyl group and a phenyl group, and particularly preferably a phenyl group.

In a preferred embodiment of the invention, each R in formulae (2) to (5) represents a substituted or unsubstituted alkyl group having 1 to 20, preferably 1 to 5, and more preferably 1 to 4 carbon atoms, and particularly preferably a methyl group or a t-butyl group; a substituted or unsubstituted aryl group having 6 to 50, preferably 6 to 24, and more preferably 6 to 18 ring carbon atoms, and particularly preferably a phenyl group; a halogen atom, more preferably a fluorine atom; or a cyano group. Each R is preferably bonded to 6-position and/or 8-position of the 2- or 4-dibenzofuranyl group and the 2- or 4-dibenzothiophenyl group.

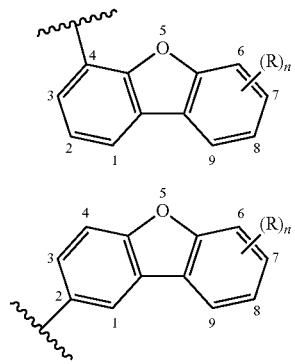

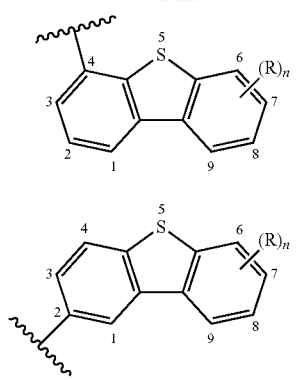

(5)

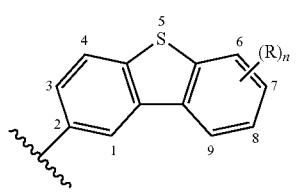

(8)

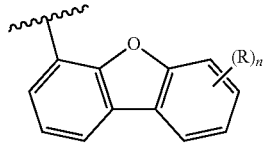

(9)

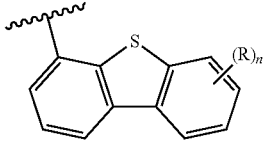

(10)

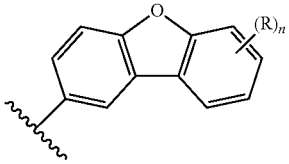

(11)

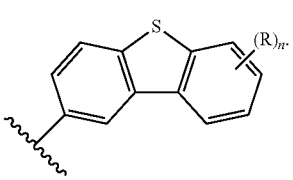

In formula (1), $L^1$ to $L^3$ may be the same or different and each independently represents a single bond, a group represented by formula (6), or a group represented by formula (7):

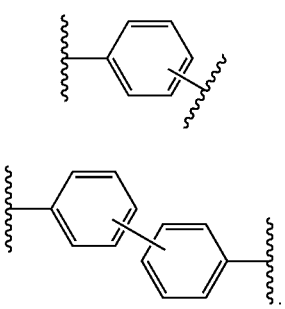

(6)

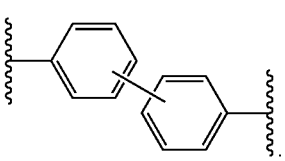

(7)

The group represented by formula (6) may include an o-phenylene group, a m-phenylene group, and a p-phenylene group, and the group represented by formula (7) may include an o-biphenylene group, a m-biphenylene group, and a p-biphenylene group.

Each of $L^1$ to $L^3$ preferably represents a single bond, a p-phenylene group or a p-biphenylene group, $L^1$ is particularly preferably a p-phenylene group, $L^3$ is particularly preferably a single bond, a p-phenylene group, or a p-biphenylene group.

In formula (1), $Ar^2$ represents a substituted or unsubstituted alkyl group having 1 to 20, preferably 1 to 5, and more preferably 1 to 4 carbon atoms, a substituted or unsubstituted aryl group having 6 to 50, preferably 6 to 24, and more preferably 6 to 18 ring carbon atoms, a substituted or unsubstituted heterocyclic group having 3 to 50, preferably 3 to 24, and more preferably 3 to 18 ring atoms, a substituted or unsubstituted fluoroalkyl group having 1 to 20, preferably 1 to 5, and more preferably 1 to 4 carbon atoms, a substituted or unsubstituted alkoxy group having 1 to 20, preferably 1 to 5, and more preferably 1 to 4 carbon atoms, a substituted or unsubstituted fluoroalkoxy group having 1 to 20, preferably 1 to 5, and more preferably 1 to 4 carbon atoms, substituted or unsubstituted aryloxy group having 6 to 50, preferably 6 to 24, and more preferably 6 to 18 ring carbon atoms, or a group selected from formulae (8) to (11):

The details of the alkyl group, the aryl group, the heterocyclic group, the fluoroalkyl group, the alkoxy group, the fluoroalkoxy group, the aryloxy group, and their preferred embodiments which are represented by $Ar^2$ are the same as those mentioned above with respect to R of formulae (2) to (5). Provided that Are does not include a carbazole skeleton and a substituted or unsubstituted amino group. In a preferred embodiment, $HAr^1$ does not include a carbazole skeleton and a substituted or unsubstituted amino group.

The details of R, n and their preferred embodiments in formulae (8) to (11) are the same as those mentioned above with respect to R and n in formulae (2) to (5). R is preferably bonded to 6-position and/or 8-position of the 2- or 4-dibenzofuranyl group or the 2- or 4-dibenzothiophenyl group.

$Ar^2$ is preferably a substituted or unsubstituted aryl group having 6 to 50, preferably 6 to 24, and more preferably 6 to 18 ring carbon atoms, or a group selected from formulae (8) to (11), and particularly preferably an aryl group selected from a phenyl group, a biphenyl-2-yl group, a biphenyl-3-yl group, a biphenyl-4-yl group, a 1,1':4',1''-terphenyl-4-yl group, a 1,1':3',1''-terphenyl-4-yl group, a 1,1':2',1''-terphenyl-4-yl group, a 1,1':4',1''-terphenyl-3-yl group, a 1,1':3',1''-terphenyl-3-yl group, a 1,1':2',1''-terphenyl-3-yl group, a 1,1':4',1''-terphenyl-2-yl group, a 1,1':3',1''-terphenyl-2-yl group, a 1,1':3',1''-terphenyl-2'-yl group, a 1,1':3',1''-terphenyl-4'-yl group, a 1-naphthyl group, a 2-naphthyl group, a 9,9-dimethylfluorene-2-yl group, a 9-methyl-9-phenylfluorene-2-yl group, 9,9-diphenylfluorene-2-yl group, and a triphenylene-2-yl group, or a group selected from formulae (8) to (11).

The group represented by $Ar^2$ may be substituted with at least one substituent selected from an alkyl group having 1 to 20, preferably 1 to 5, and more preferably 1 to 4 carbon atoms, for example, a methyl group, an ethyl group, a n-propyl group, an isopropyl group, a n-butyl group, an isobutyl group, a s-butyl group, and a t-butyl group; an aryl group having 6 to 50, preferably 6 to 24, and more preferably 6 to 18 ring carbon atoms, for example, a phenyl group; a halogen atom, for example, a fluorine atom; a fluoroalkyl group having 1 to 20, preferably 1 to 5, and more preferably 1 to 4 carbon atoms, for example, a trifluoromethyl group; an alkoxy group having 1 to 20, preferably 1 to 5, and more preferably 1 to 4 carbon atoms, for example, a methoxy group; a fluoroalkoxy group having 1 to 20, preferably 1 to 5, and more preferably 1 to 4 carbon atoms, for example, a trifluoromethoxy group; and a cyano group. Preferably, $Ar^2$ is an unsubstituted group.

The aromatic amine derivative of the invention is preferably represented by formula (12):

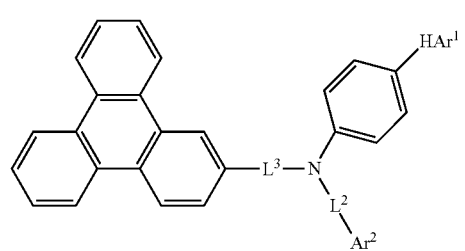

(12)

wherein $HAr^1$, $Ar^2$, $L^2$, and $L^3$ are as defined in formula (1). An aromatic amine derivative represented by formula (1) or (12), wherein $L^3$ is a single bond or a group represented by formula (13) or (14);

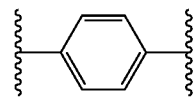

(13)

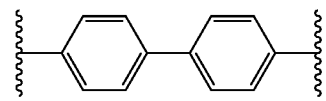

(14)

is also preferred.

Formula (12) and $HAr^1$ which is selected from formulae (2) to (5) include a p-biphenyl structure partly. The p-position of the benzene ring which is directly bonded to the central nitrogen atom is dense with electron and therefore electrochemically unstable. Since the p-biphenyl has a structure where the p-position of the benzene ring is substituted and protected with a phenyl group, the stability of the compound is improved and the material is prevented from being deteriorated, thereby prolonging the lifetime of an organic EL device.

Examples of the aromatic amine derivative represented by formula (1) are shown below, although not limited to the following compounds.

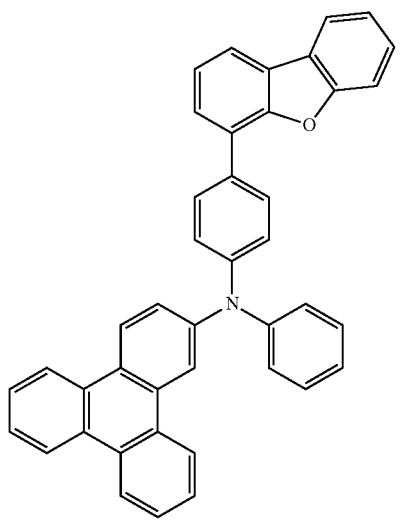

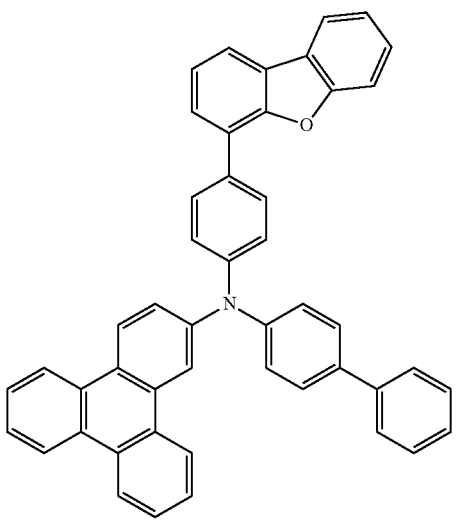

13
14
-continued
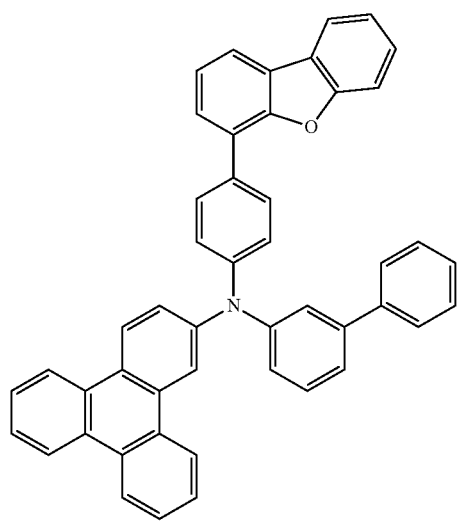
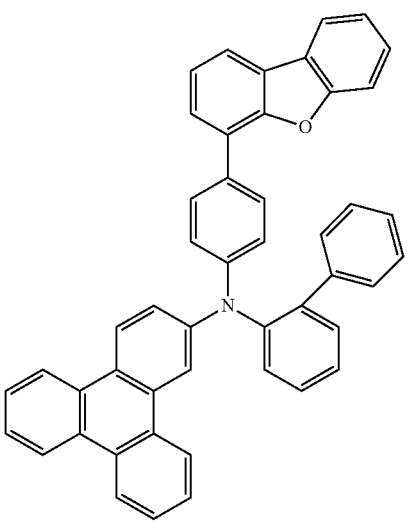
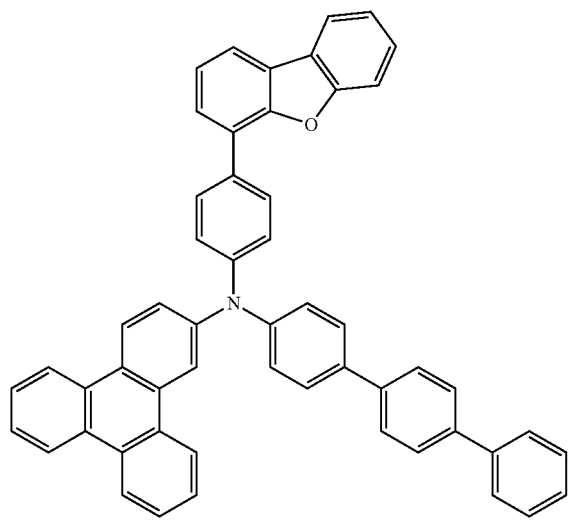
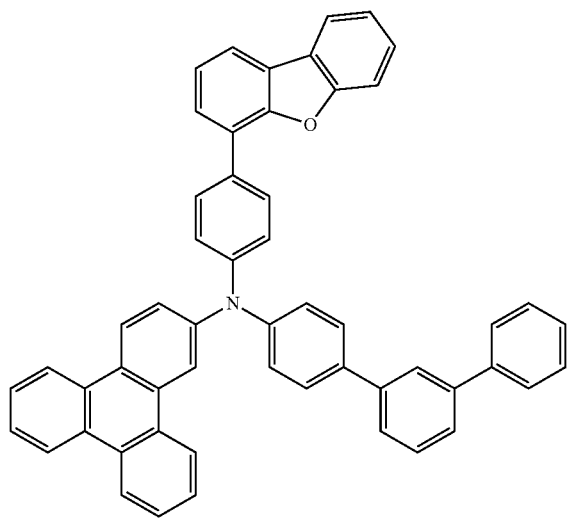
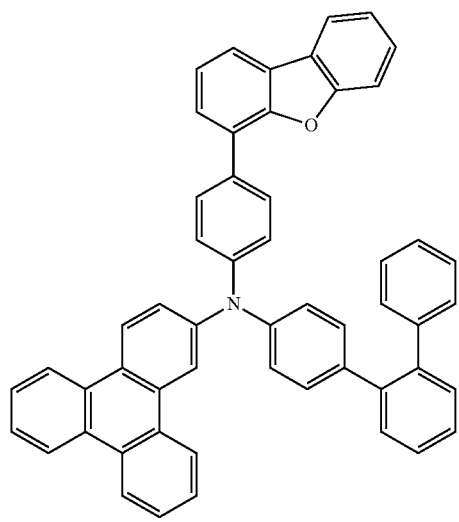
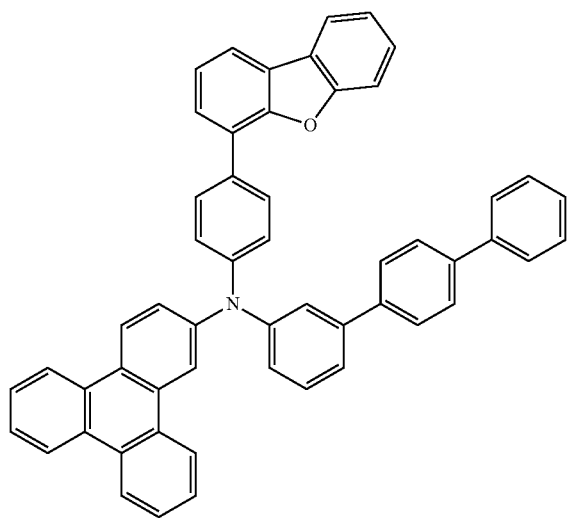

15
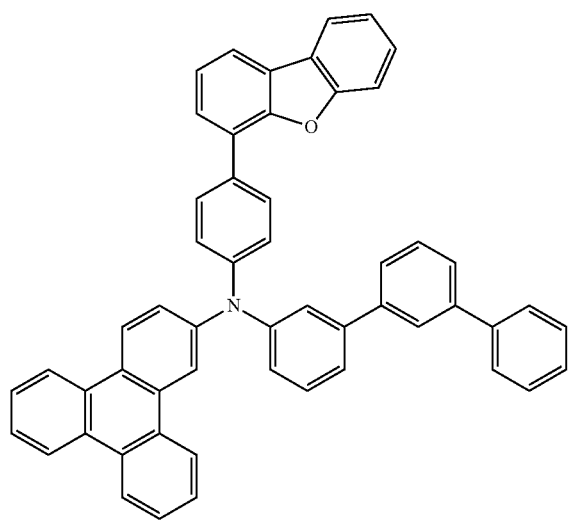
16
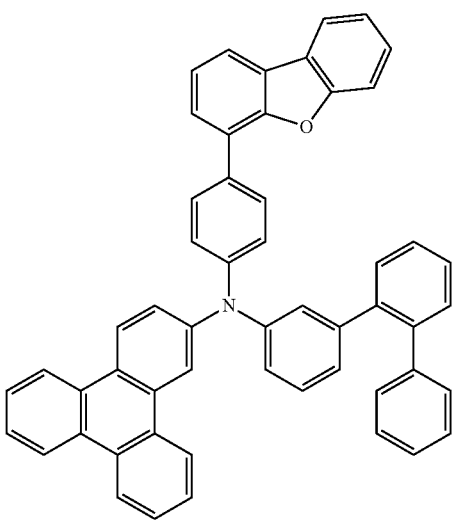
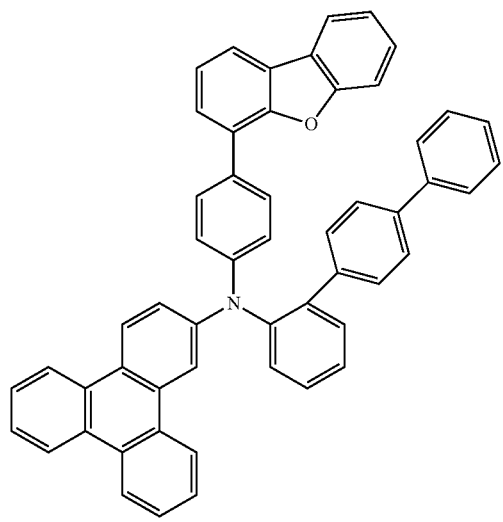
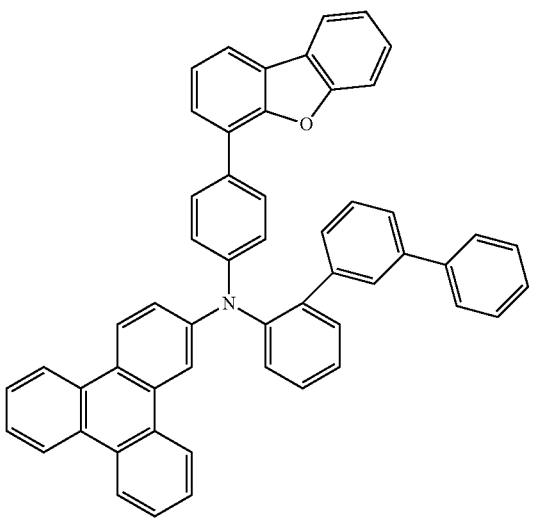
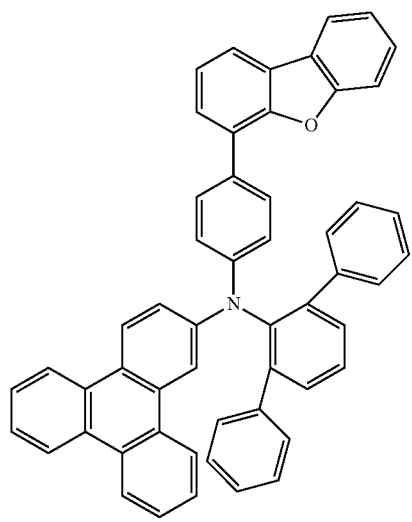
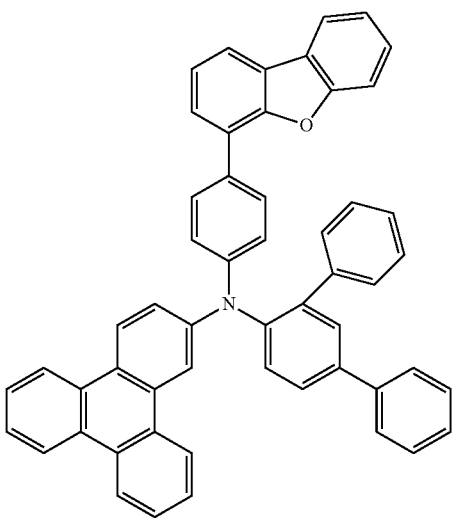

-continued
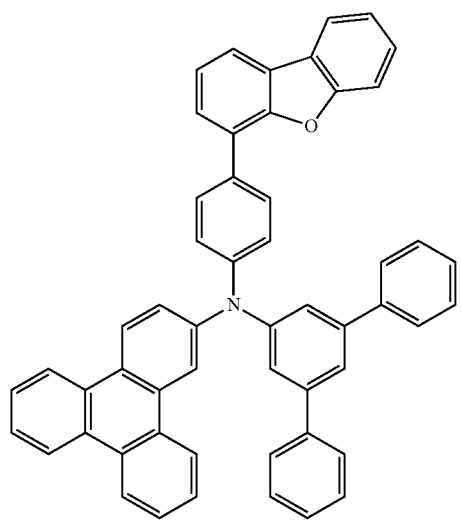
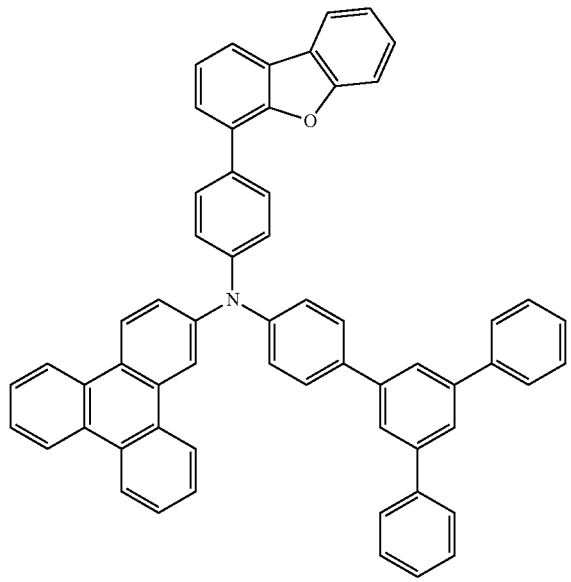
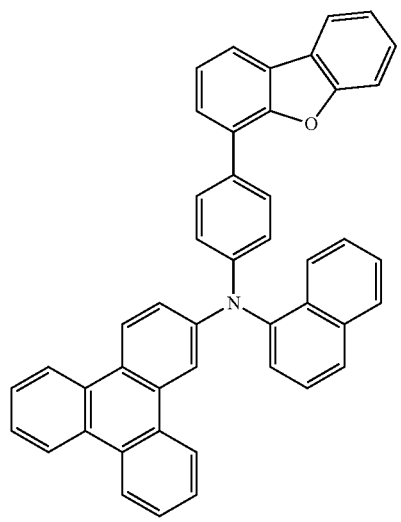
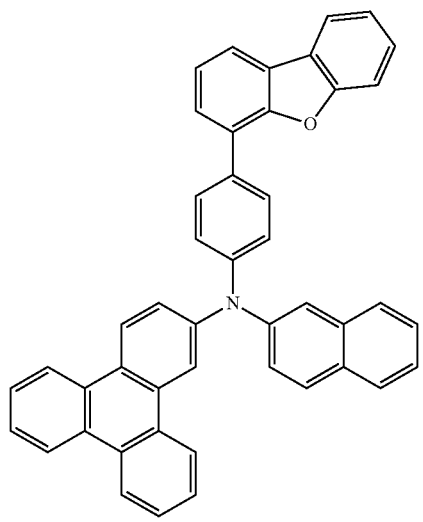
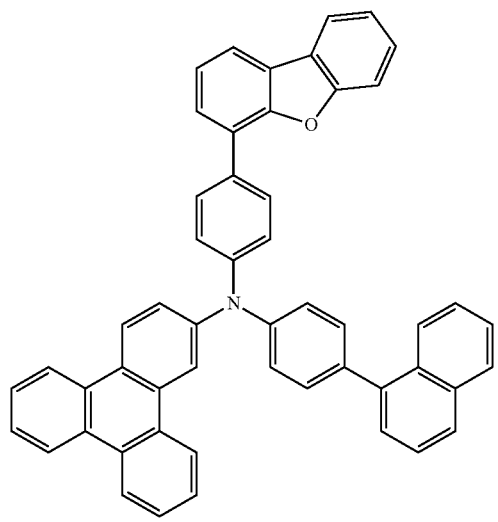
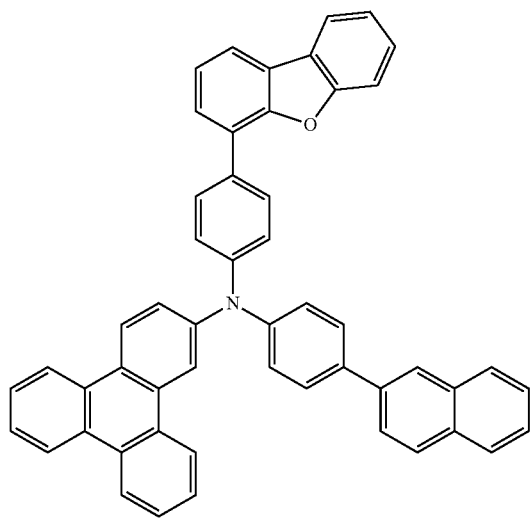

-continued
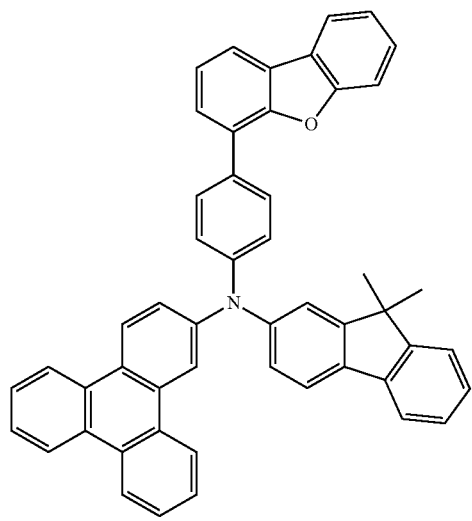
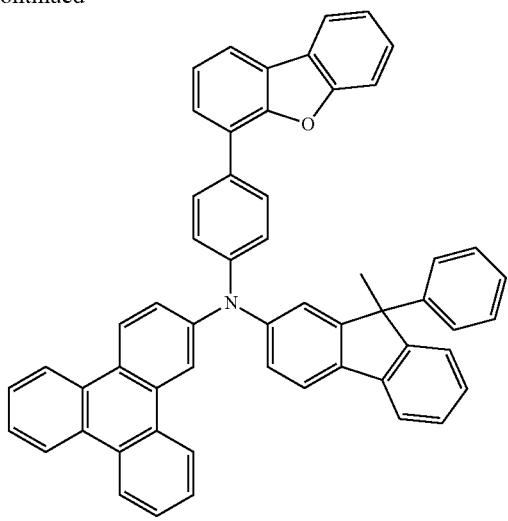
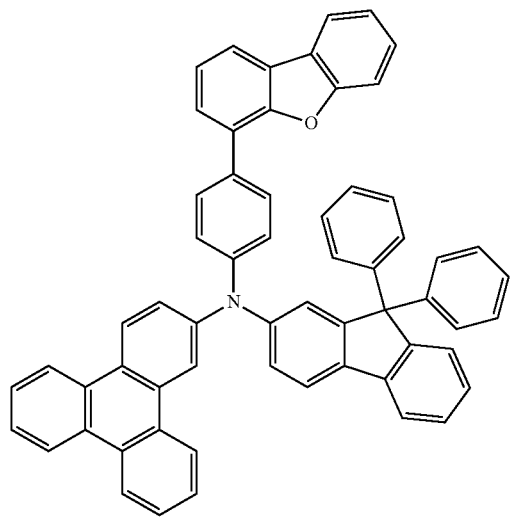
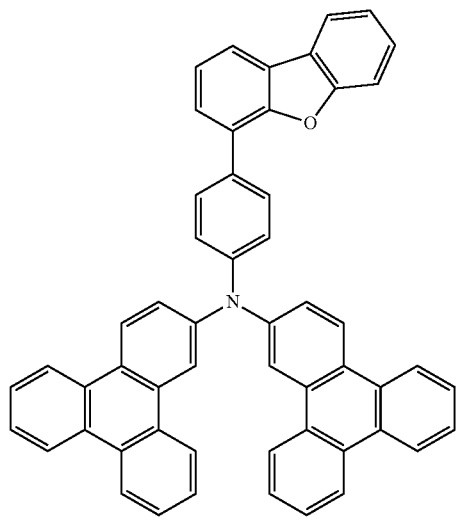
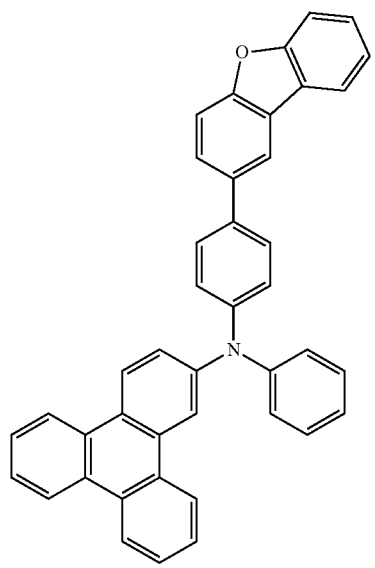
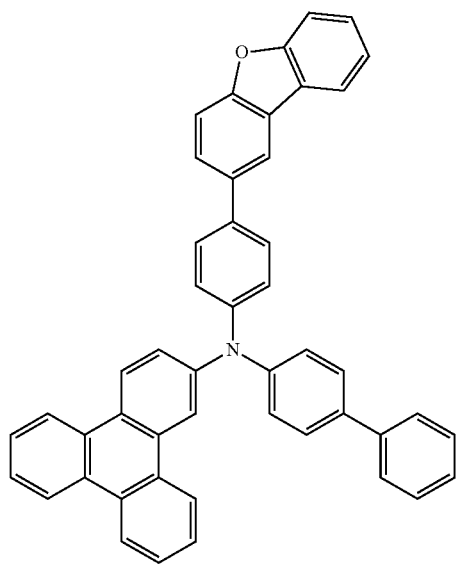

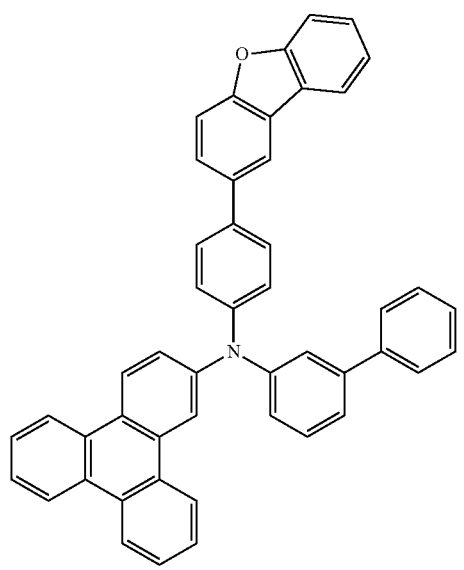
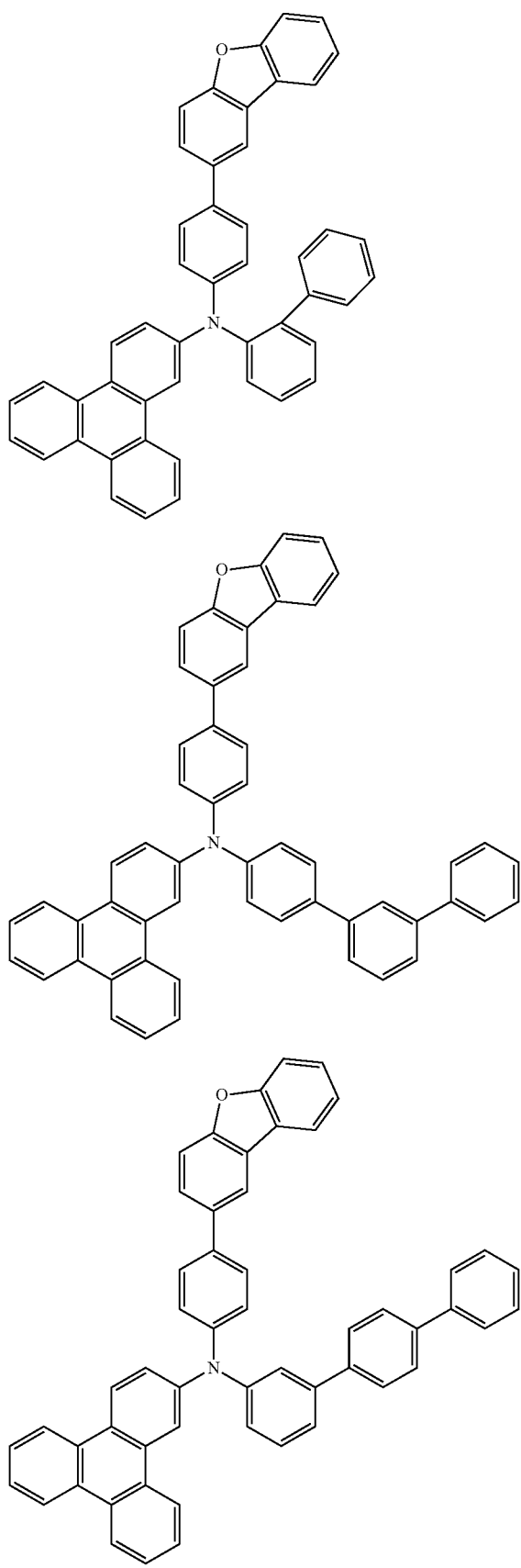

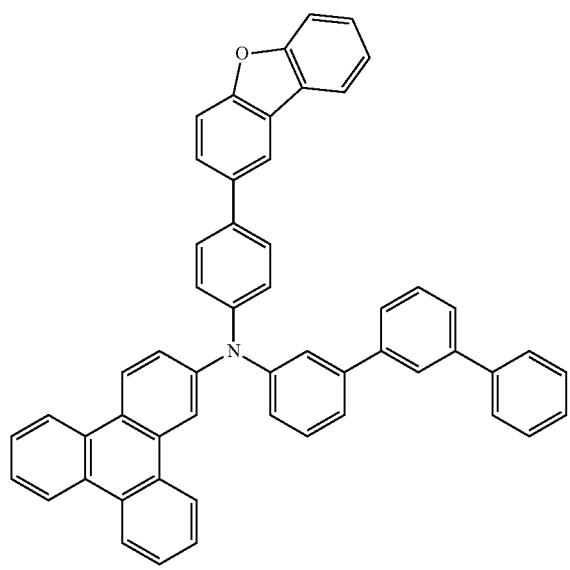
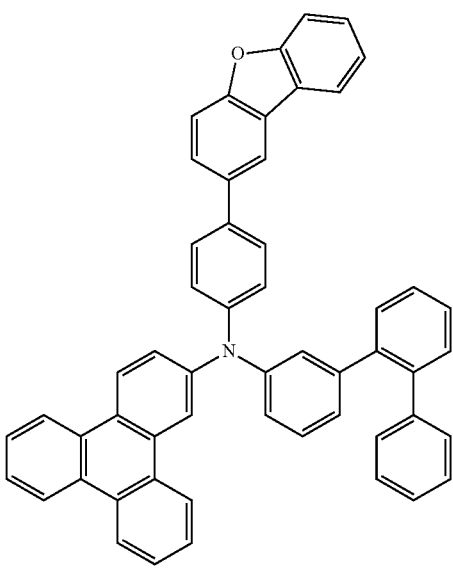
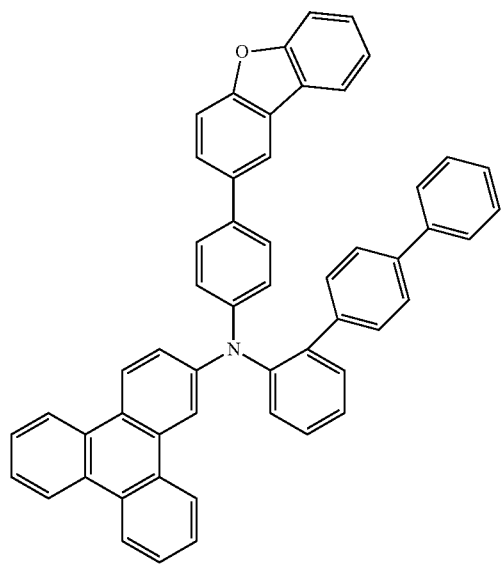
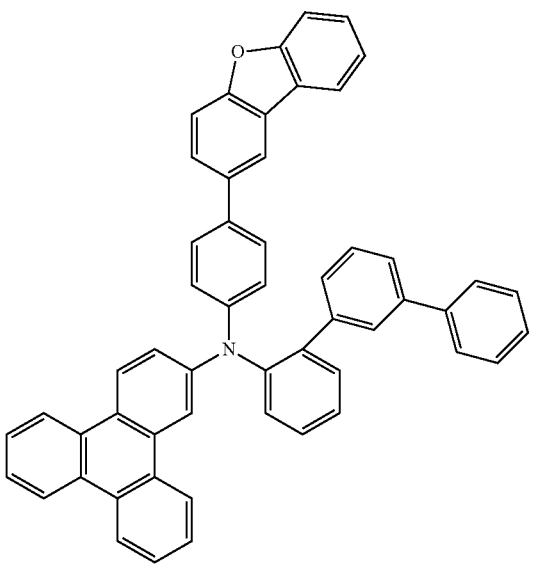
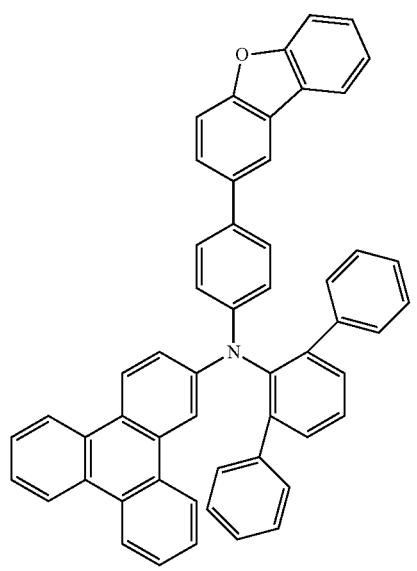
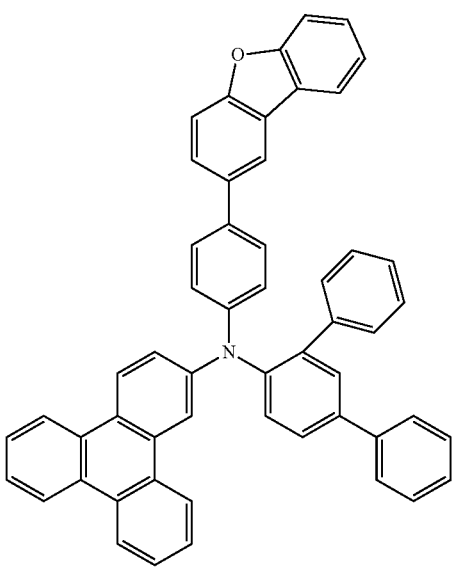

-continued
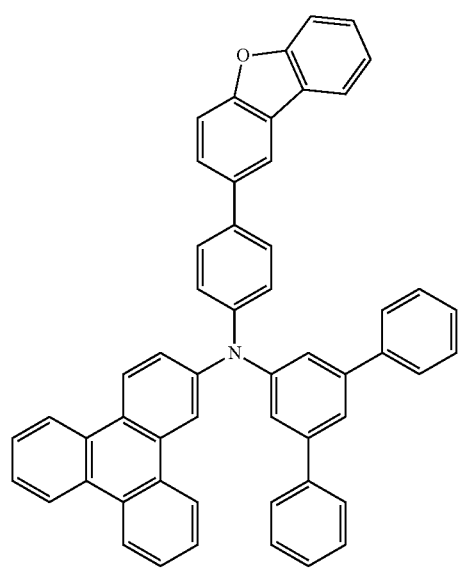
25
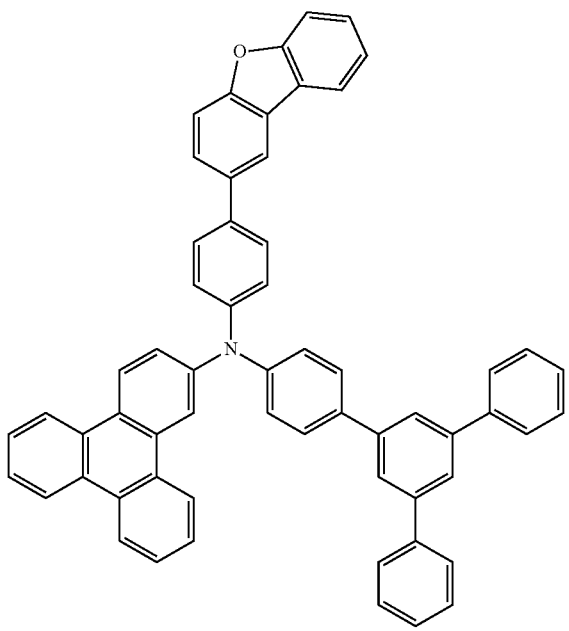
26
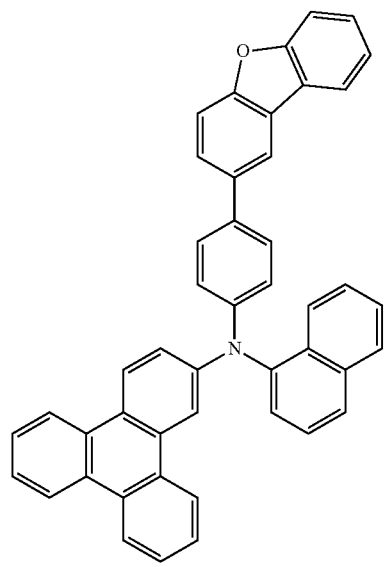
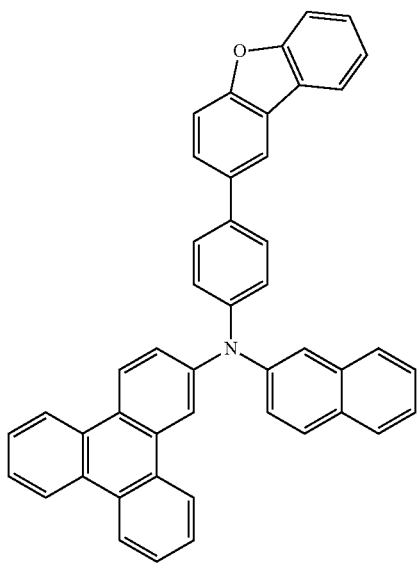

-continued
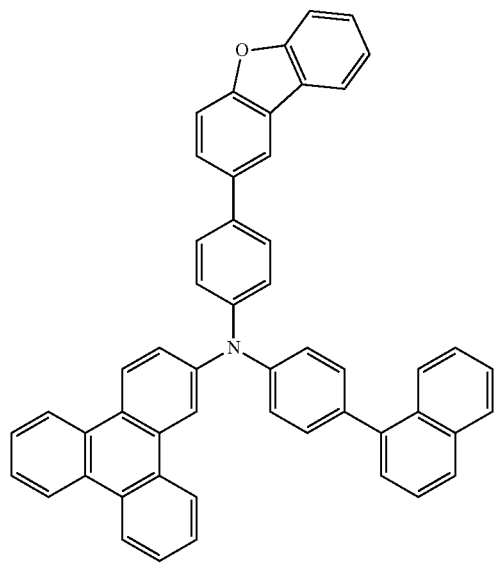
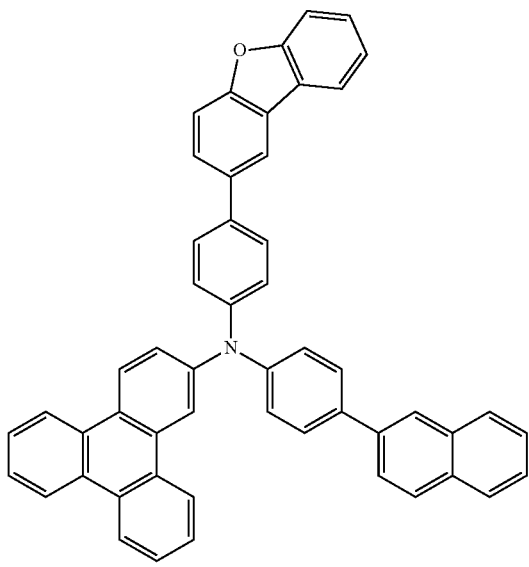
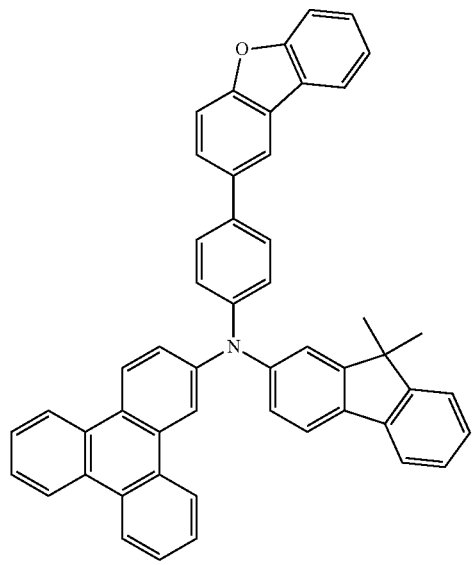
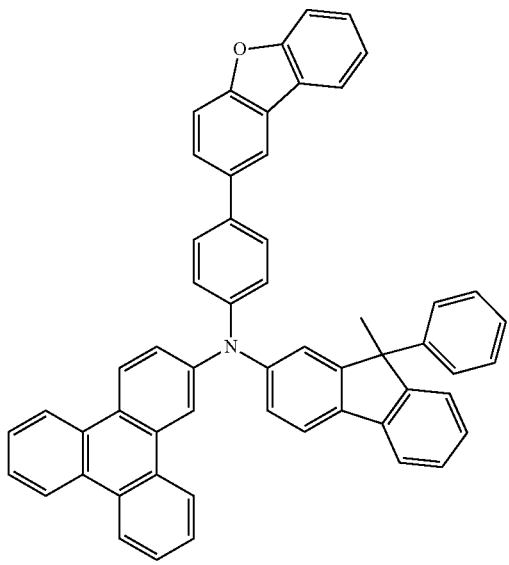
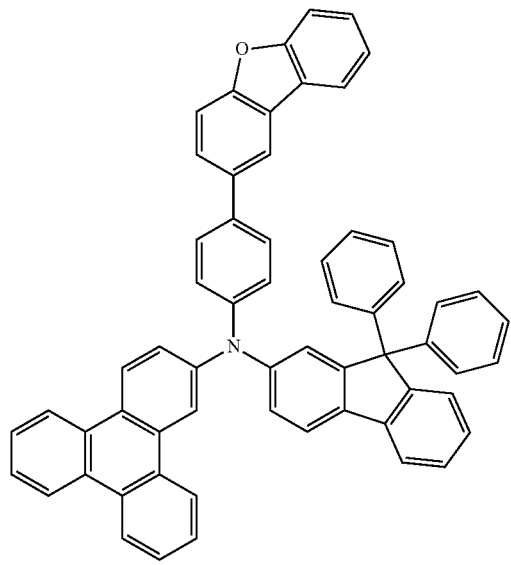
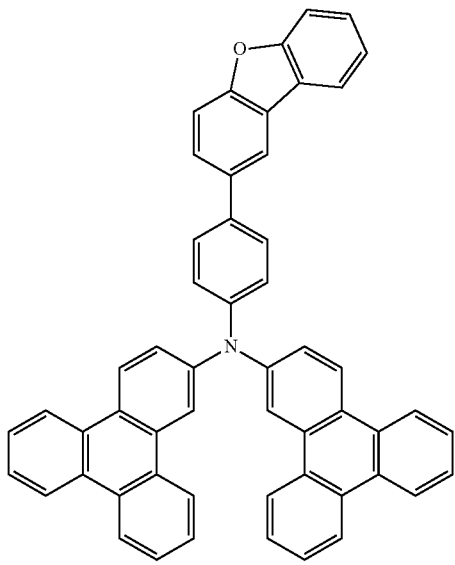

-continued
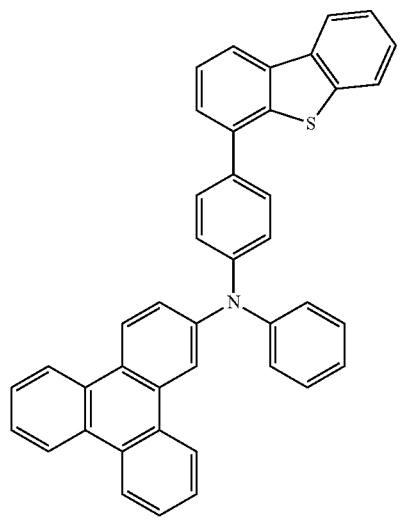
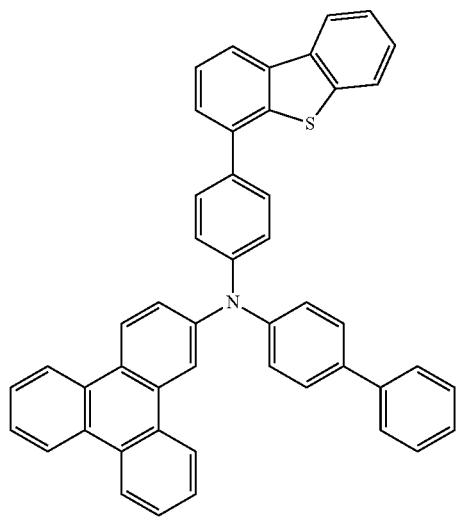
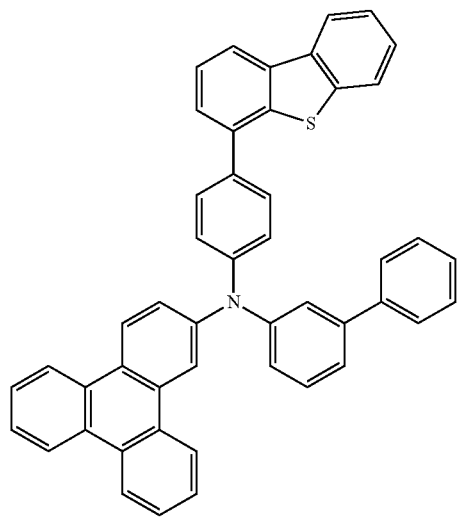
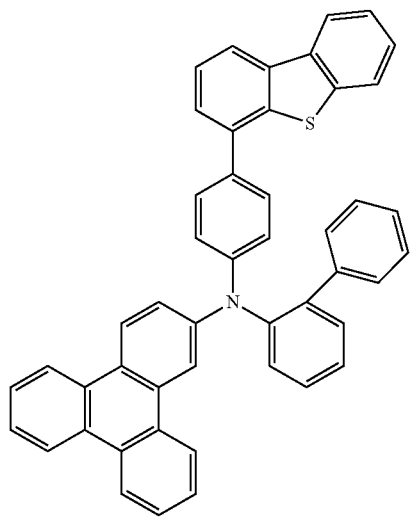
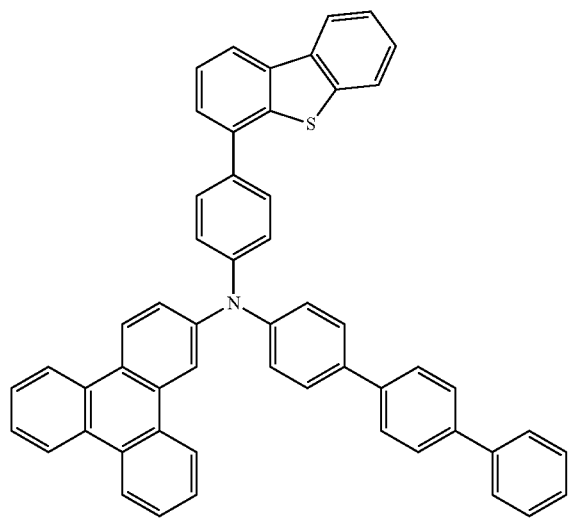
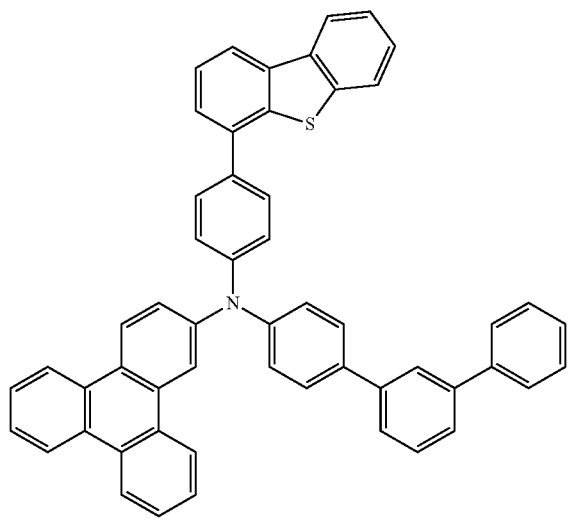

31
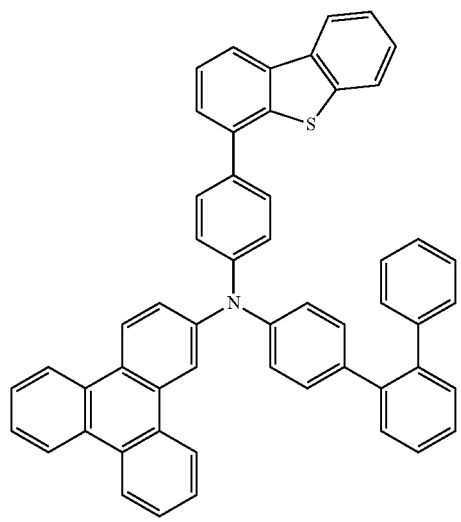
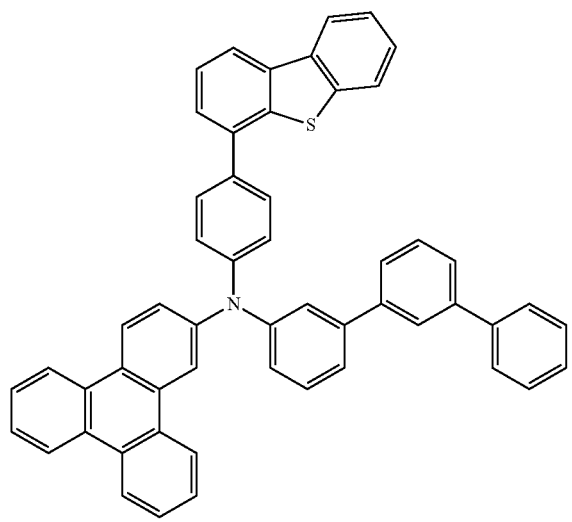
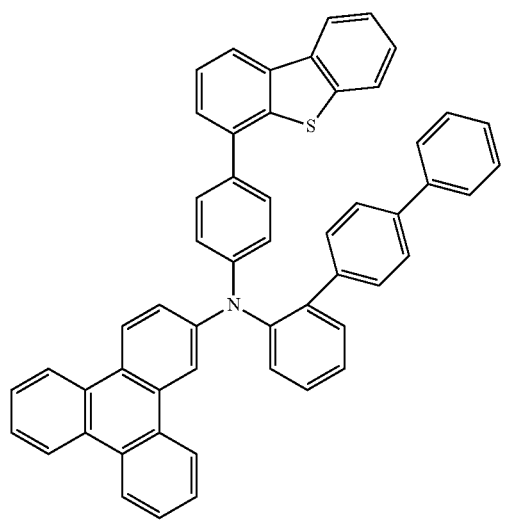
32
-continued
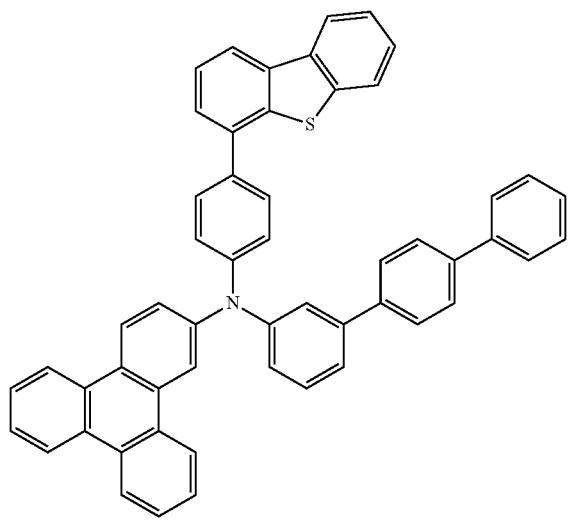
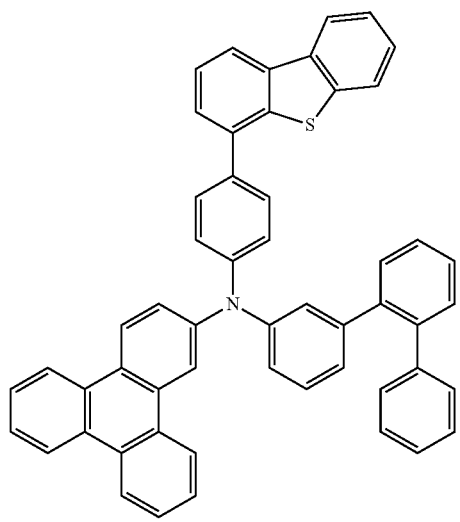
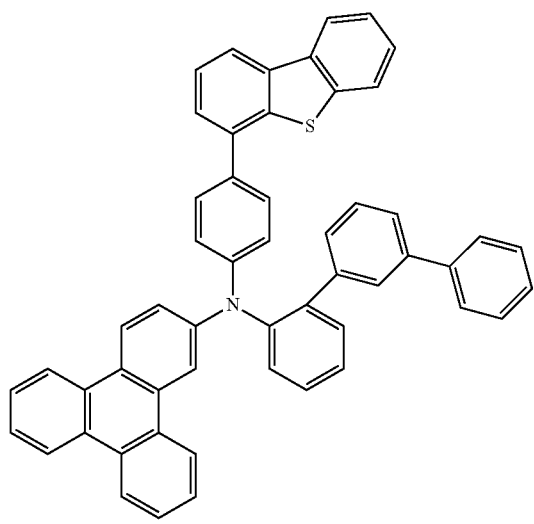

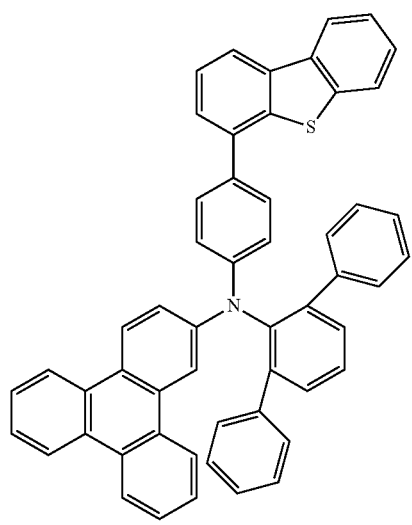
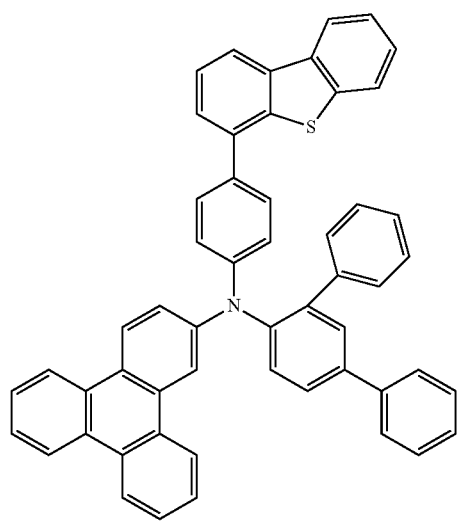
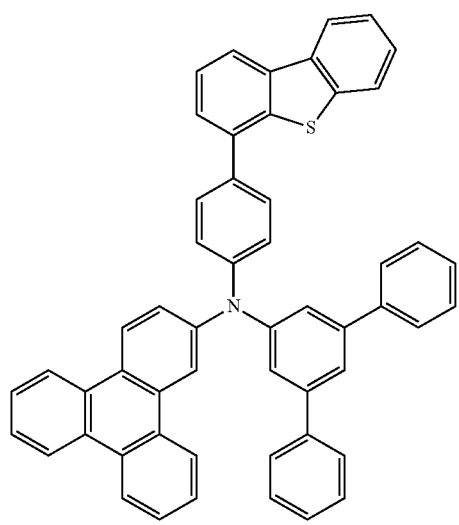
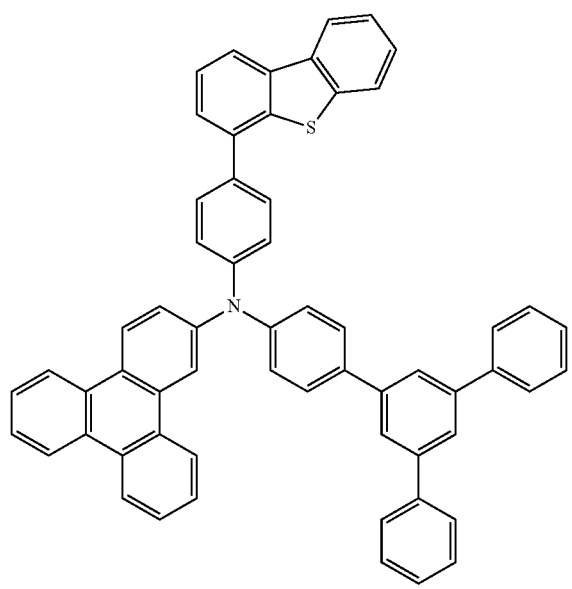
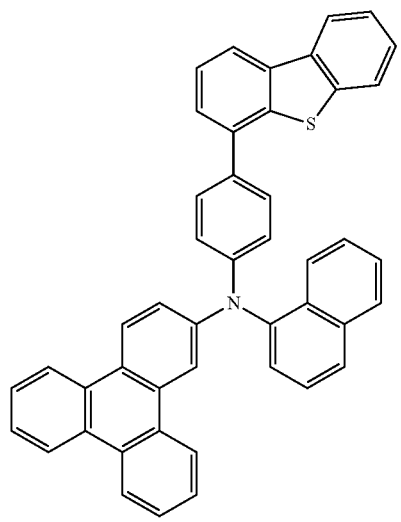
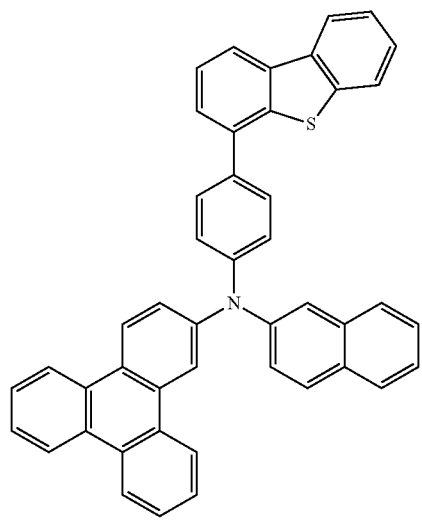

-continued
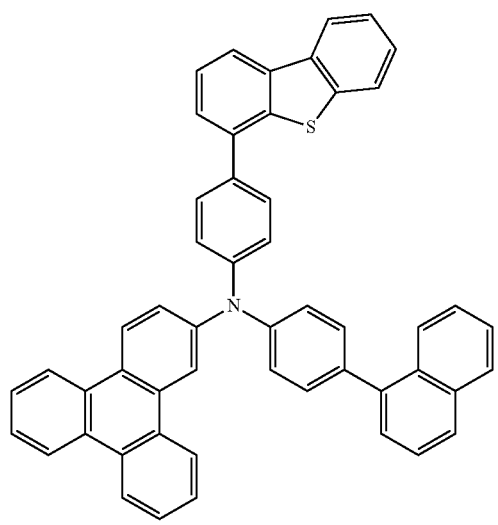
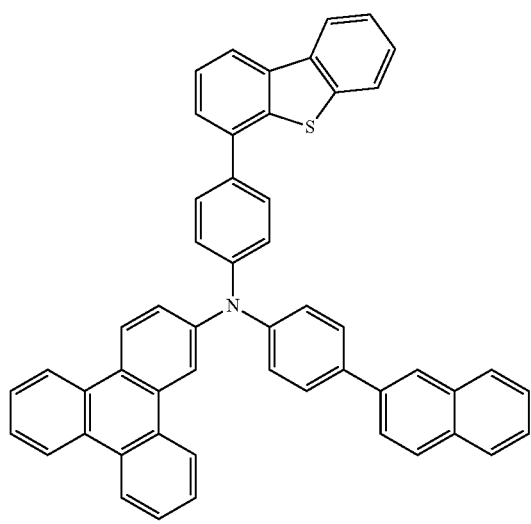
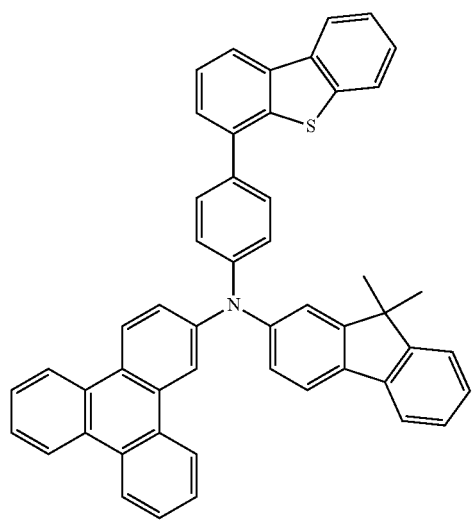
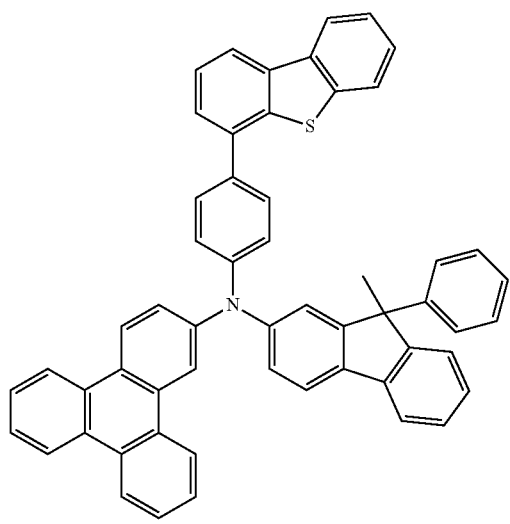
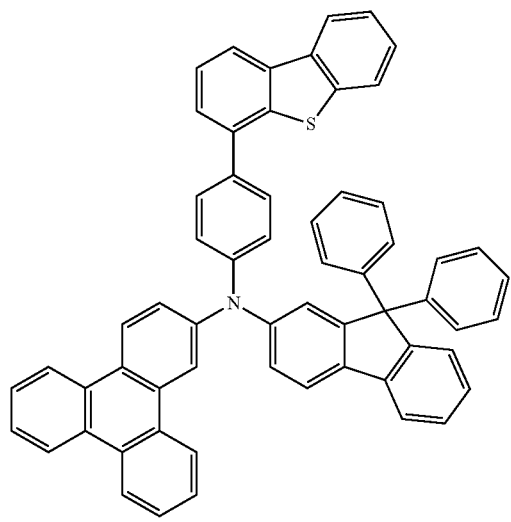
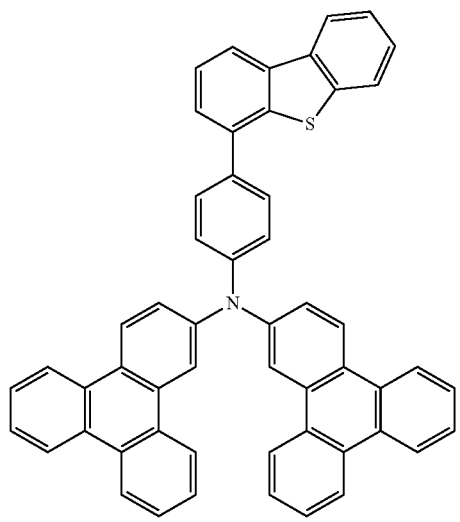

-continued
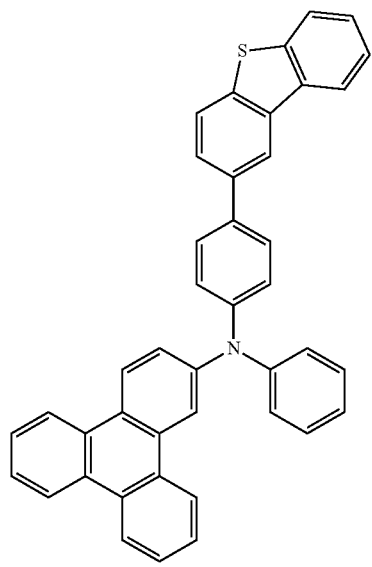
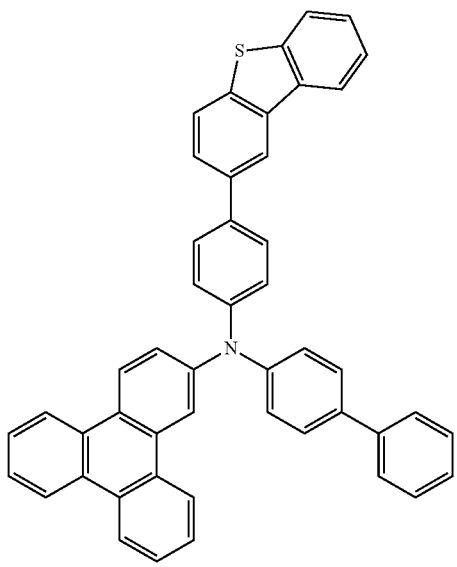
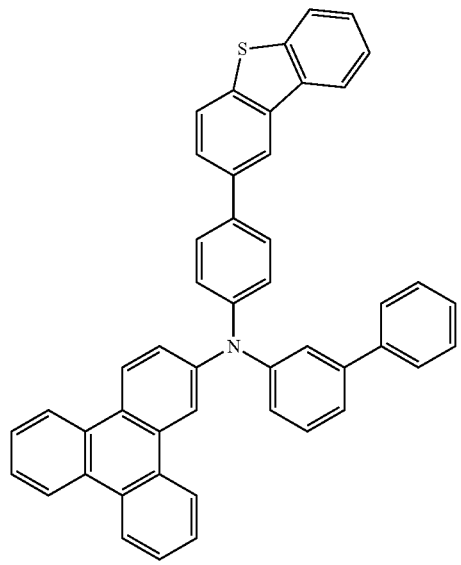
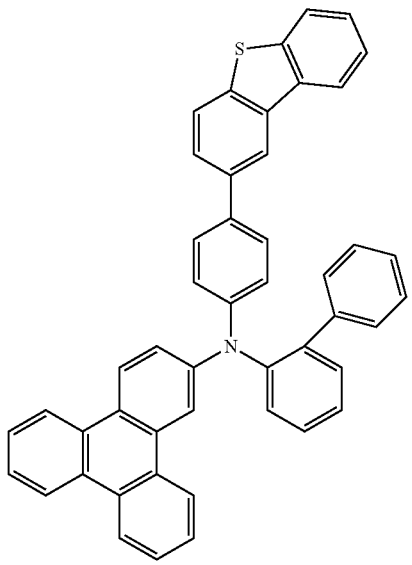
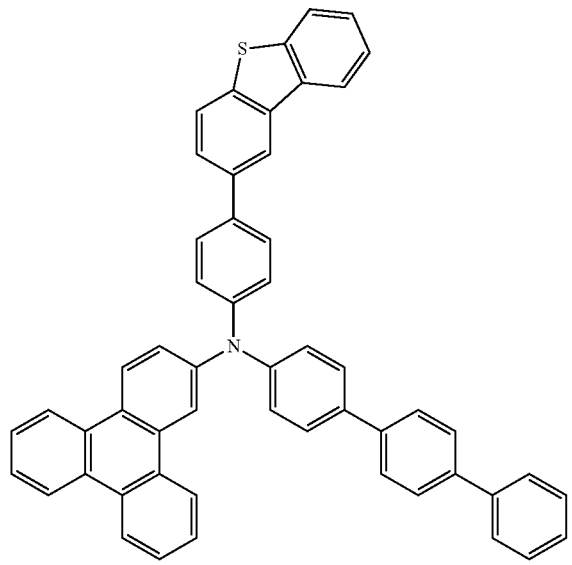
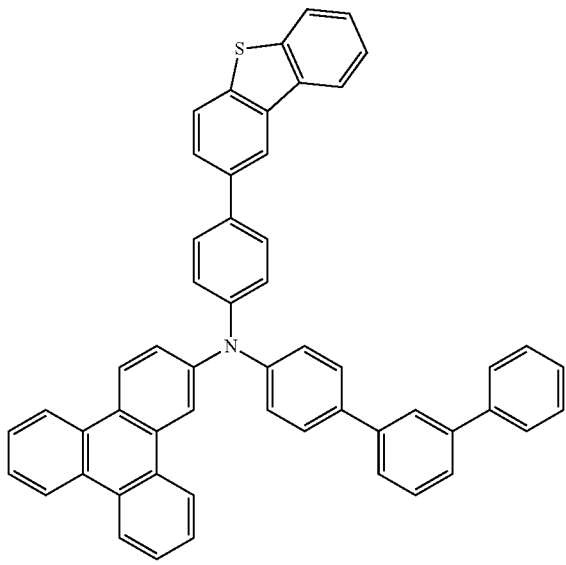

-continued
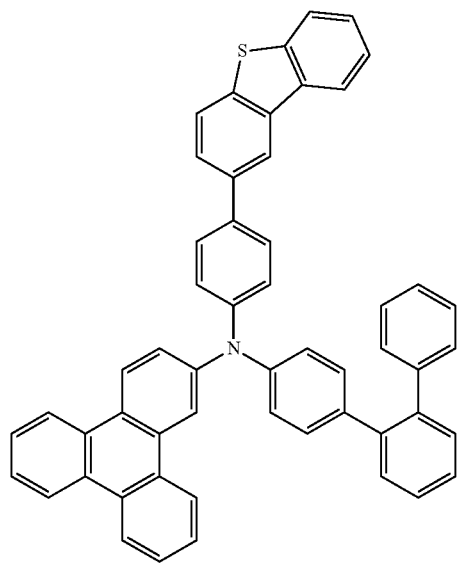
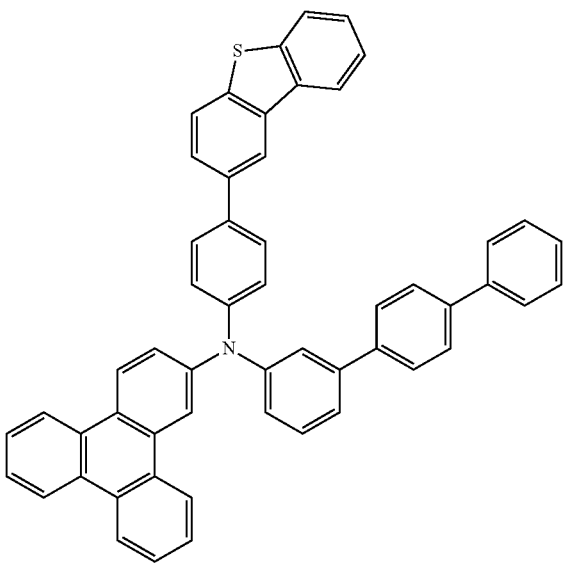
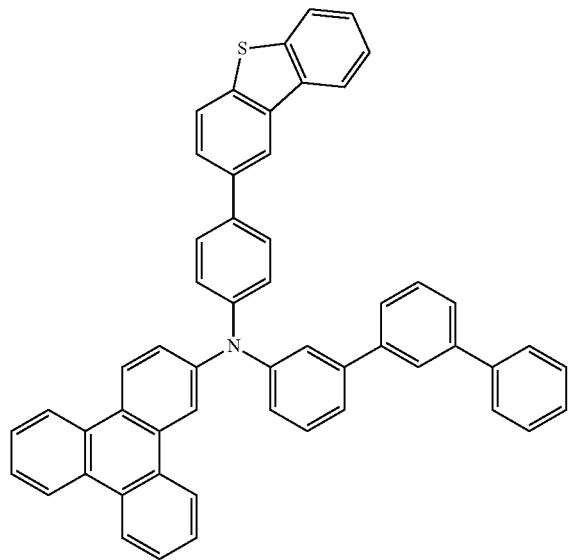
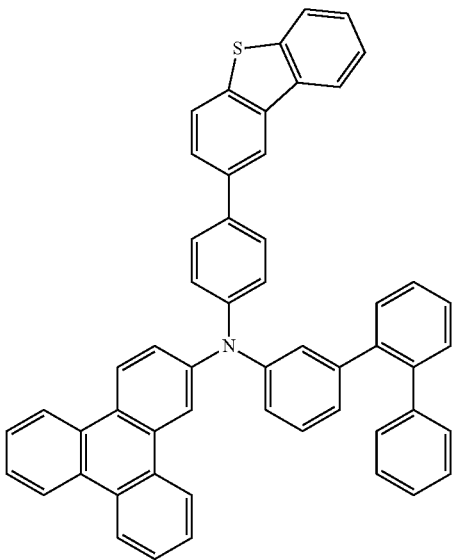
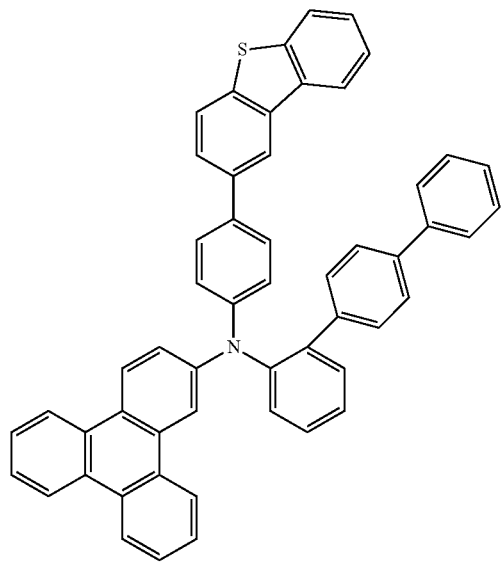
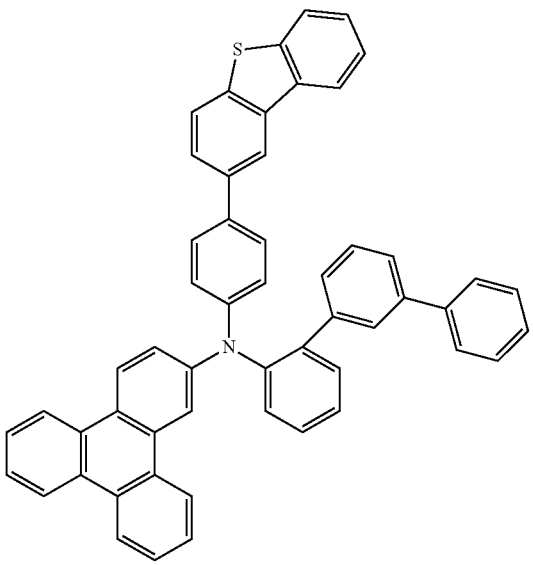

41
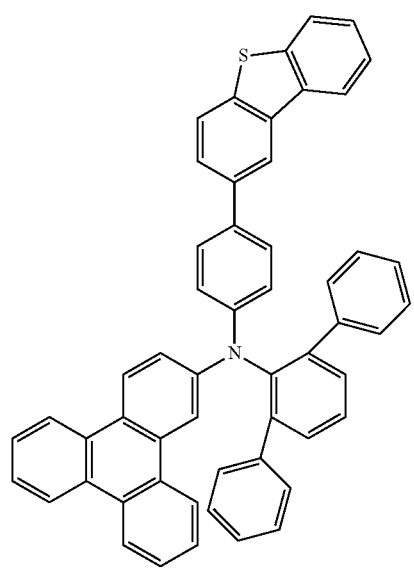
42
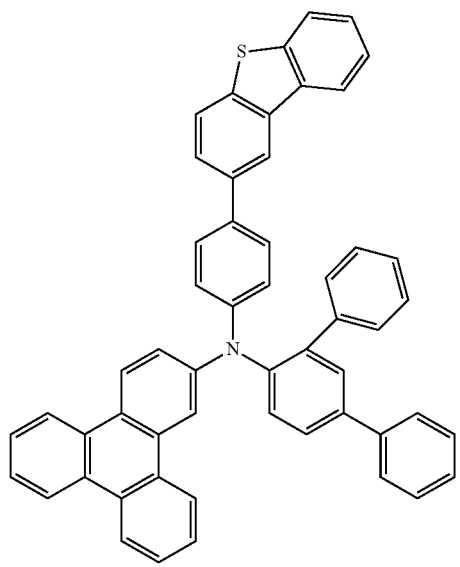
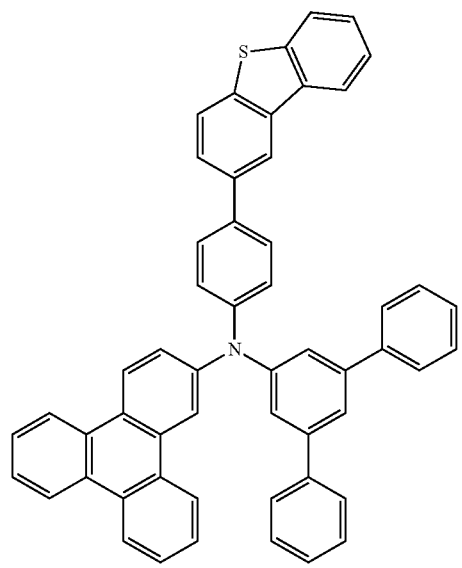
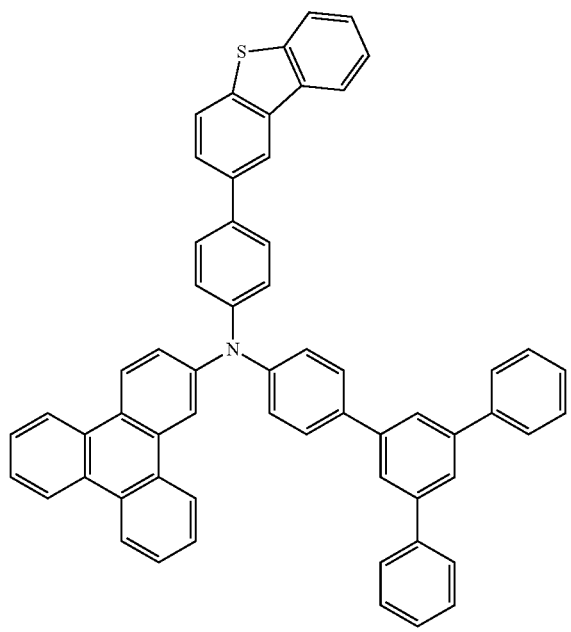

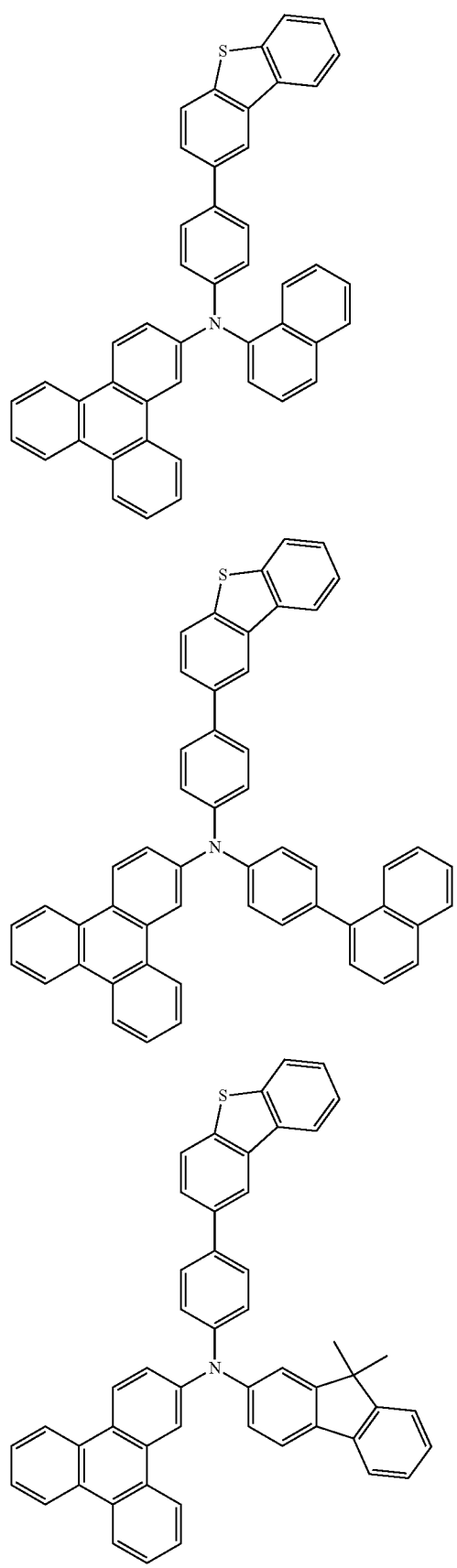
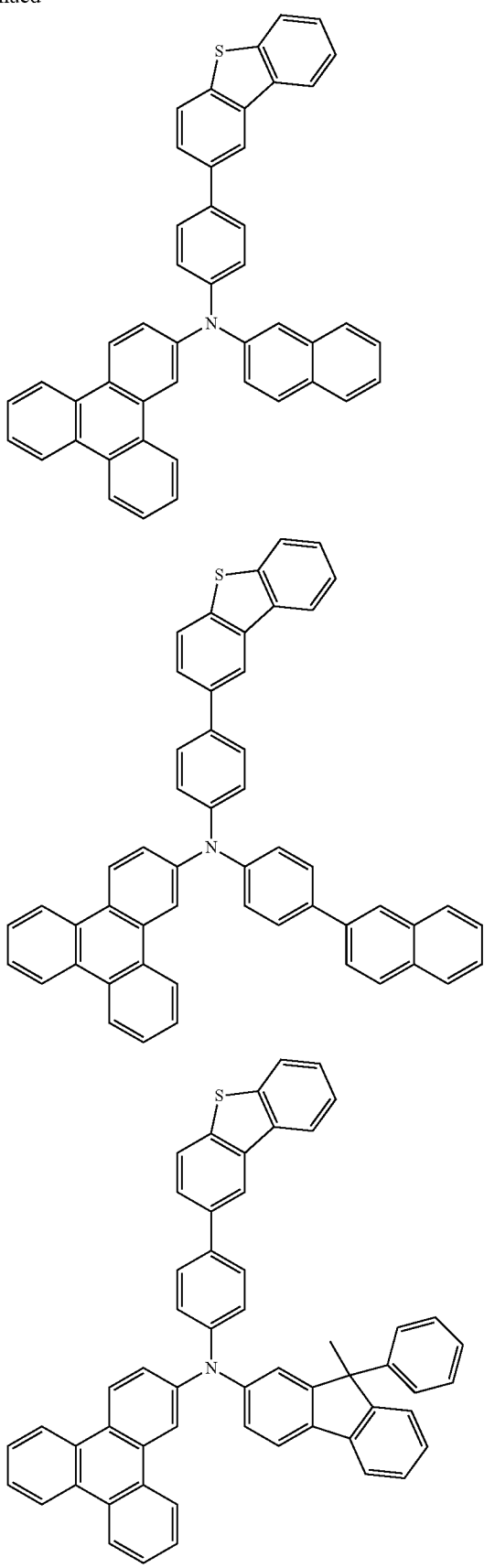

45
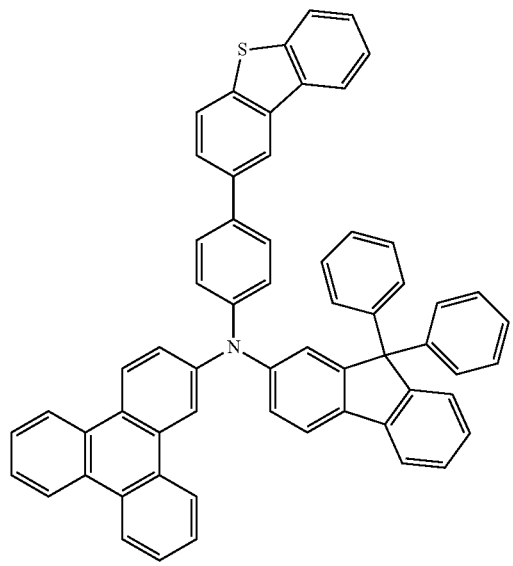
46
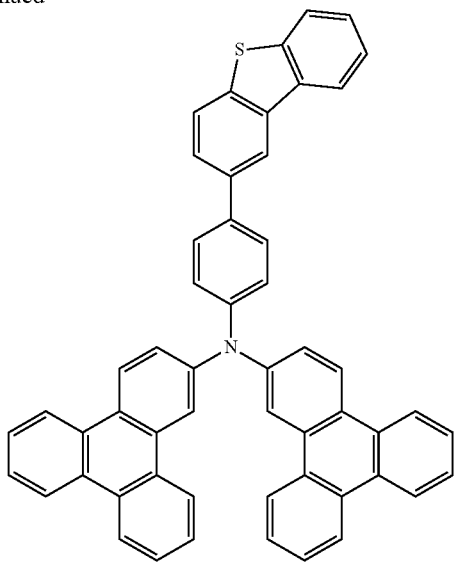
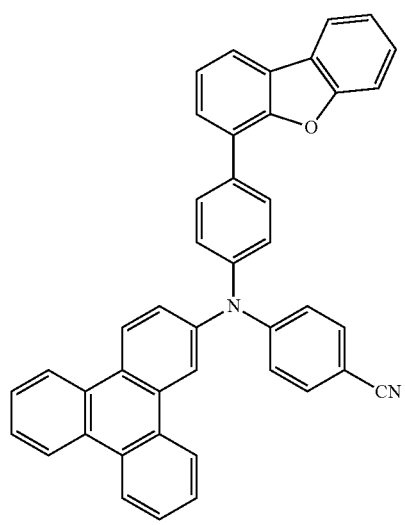
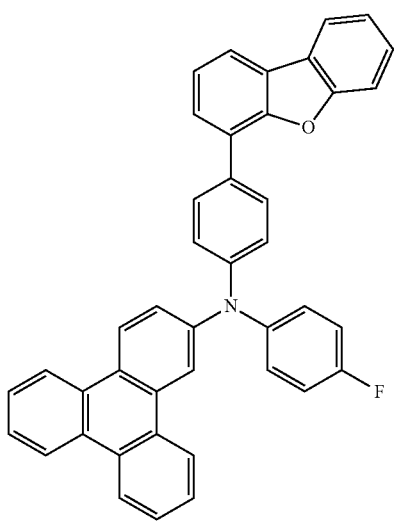
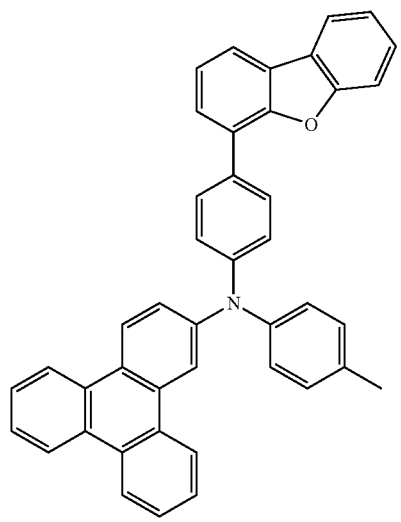
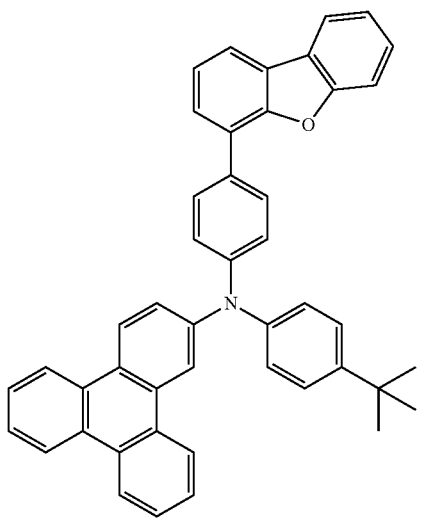

47
48
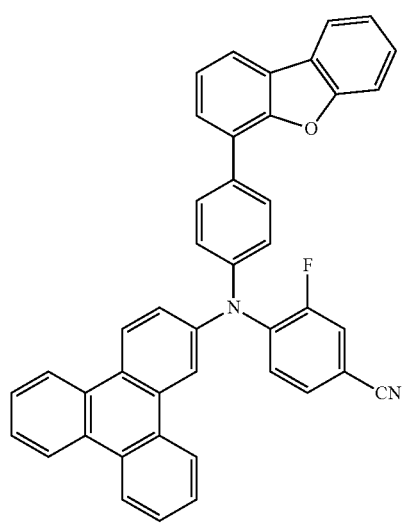
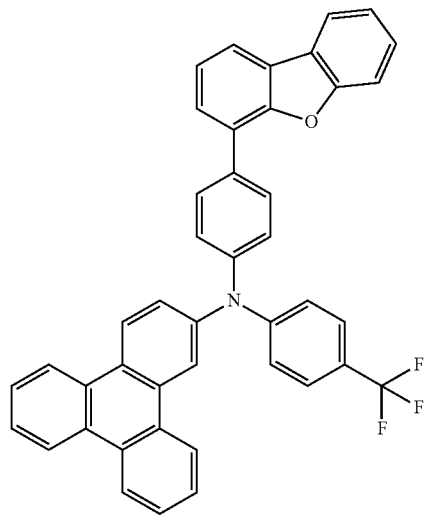
-continued
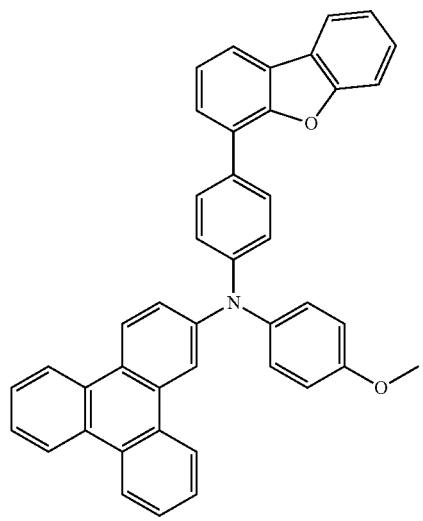
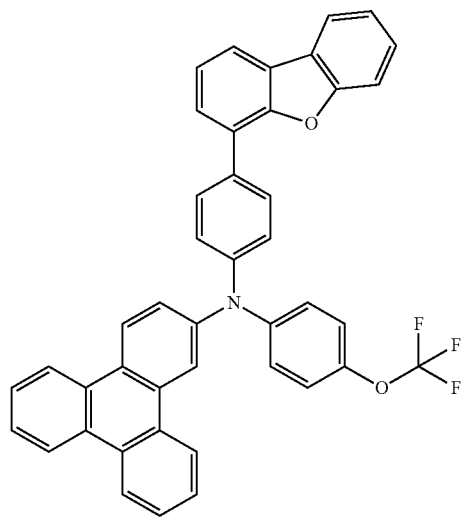
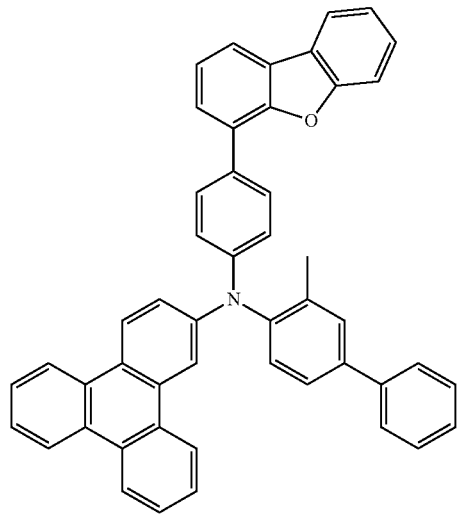
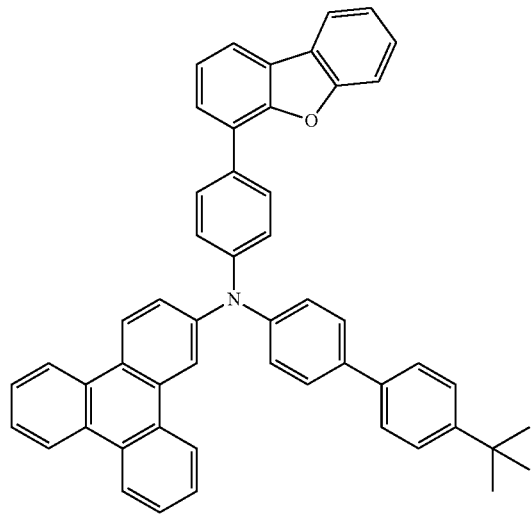

49
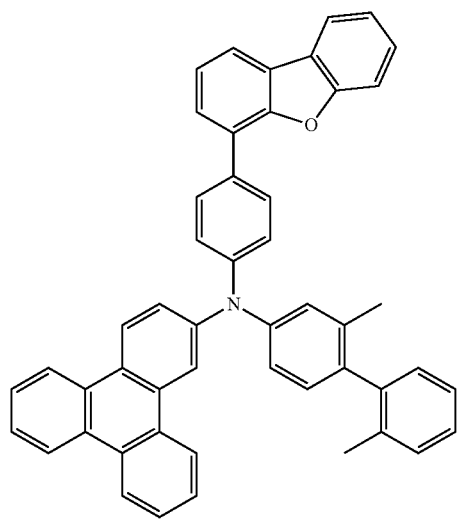
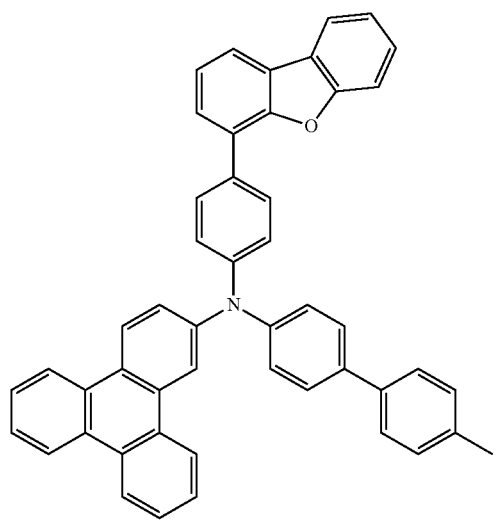
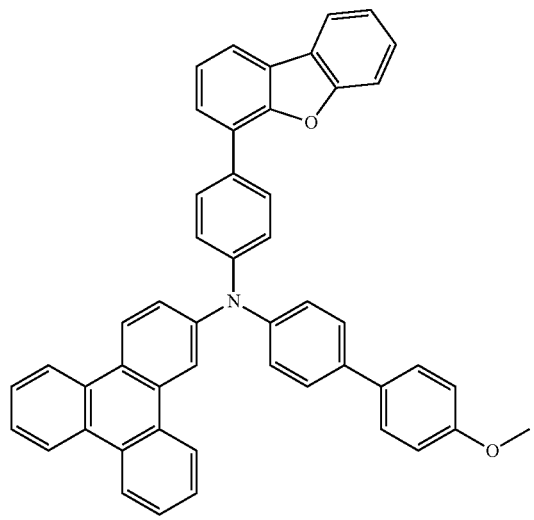
50
-continued
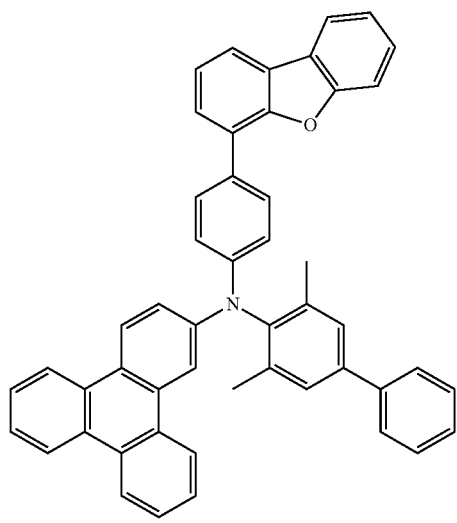
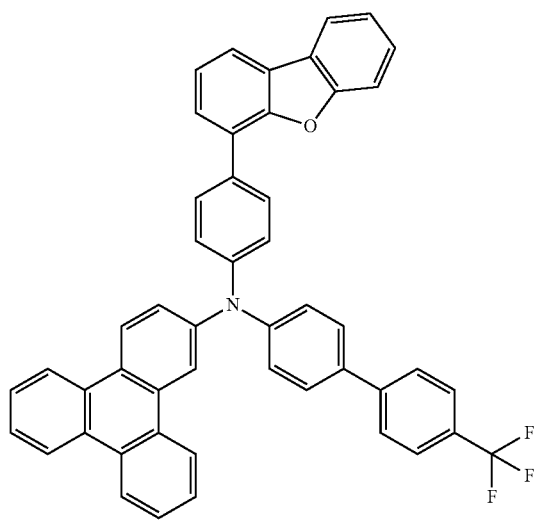
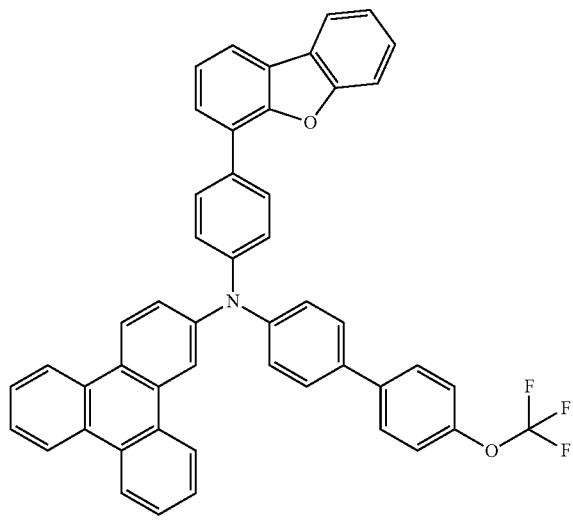

-continued
| 51 | 52 |
|---|---|
| 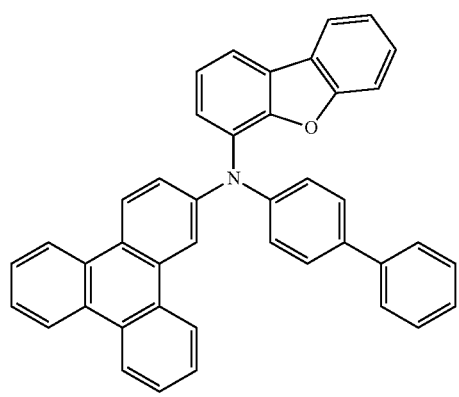 | 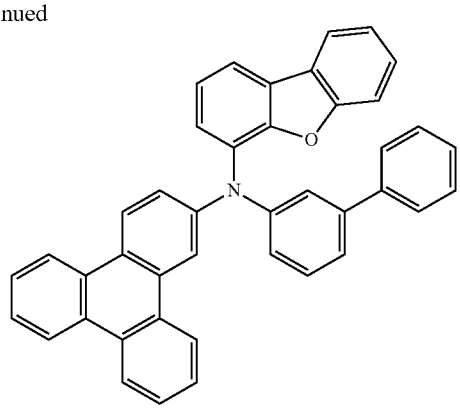 |
| 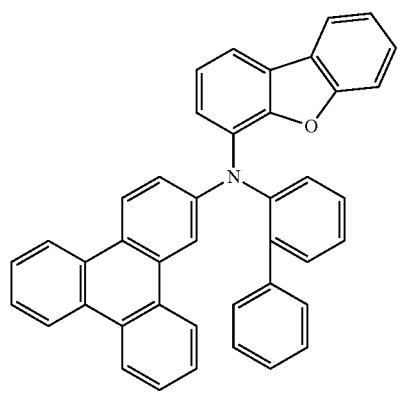 | 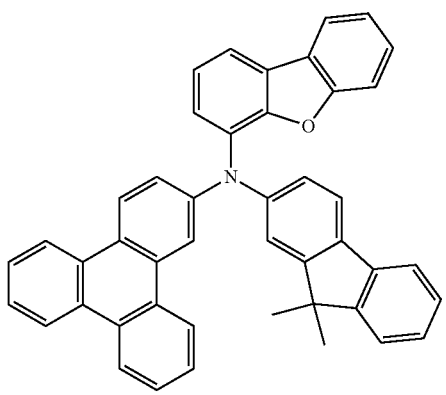 |
| 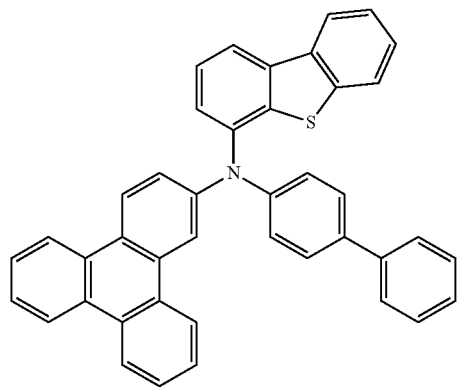 | 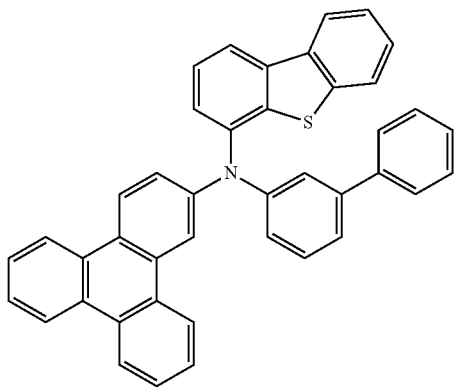 |
| 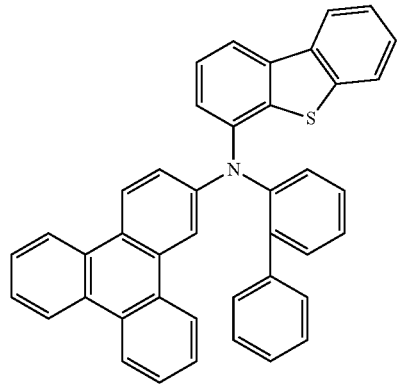 | 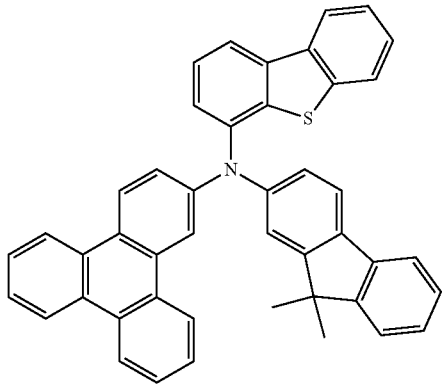 |

53
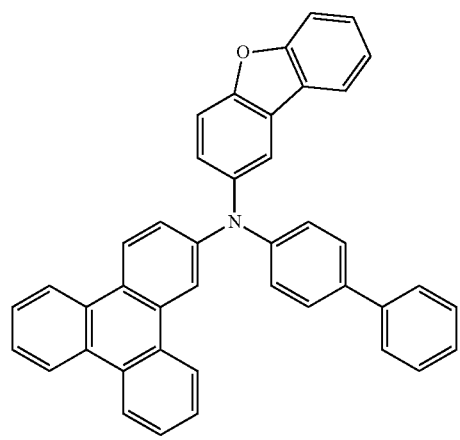
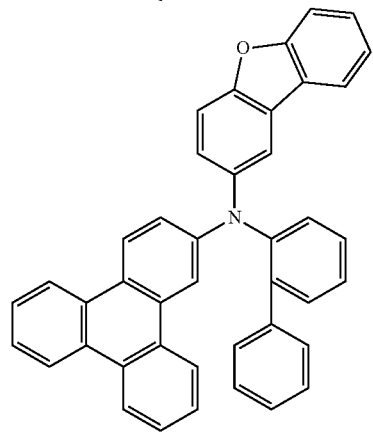
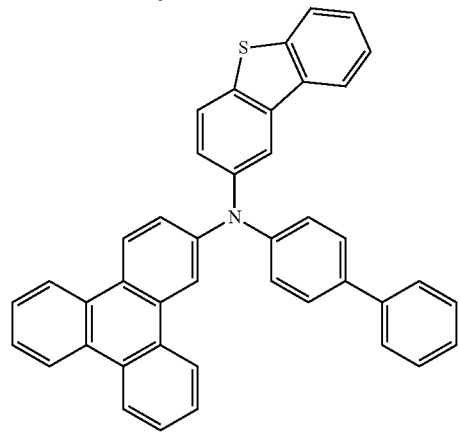
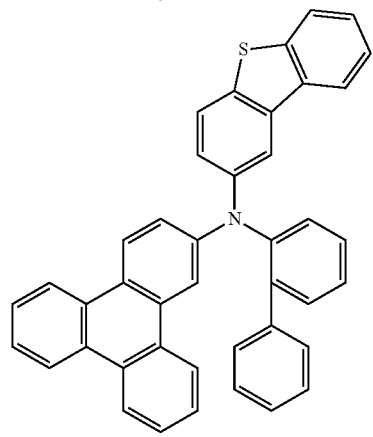
54
-continued
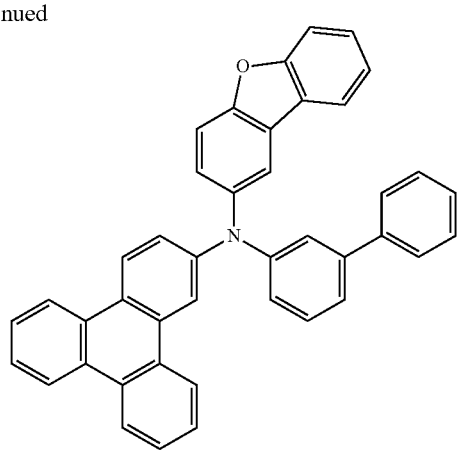
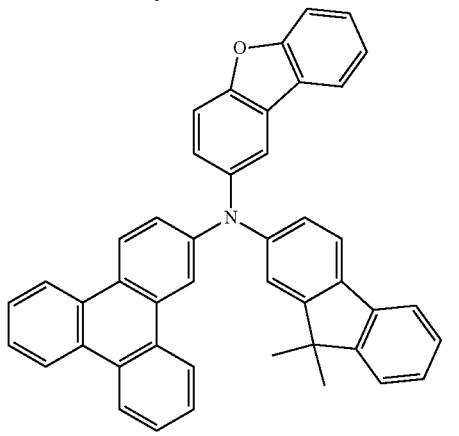
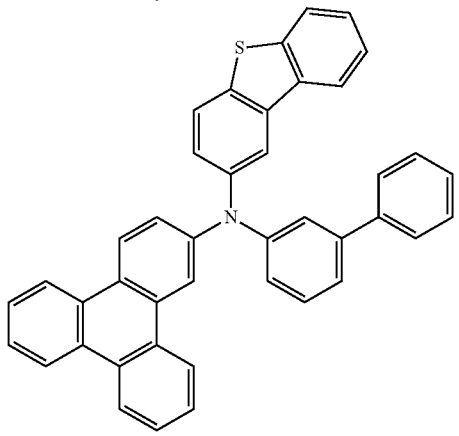
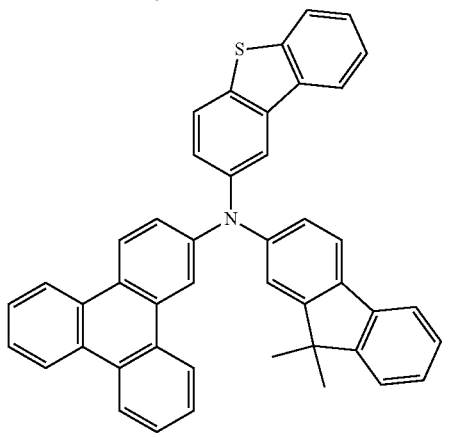

55
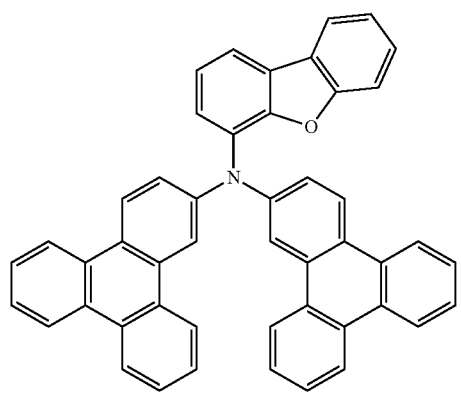
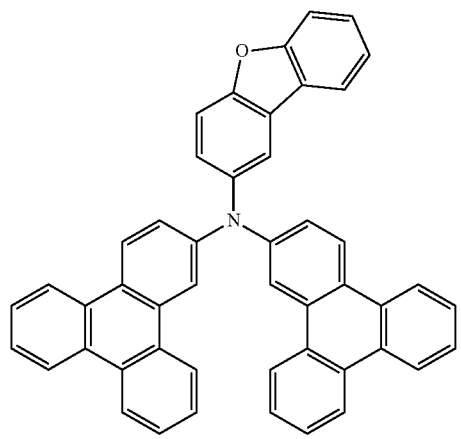
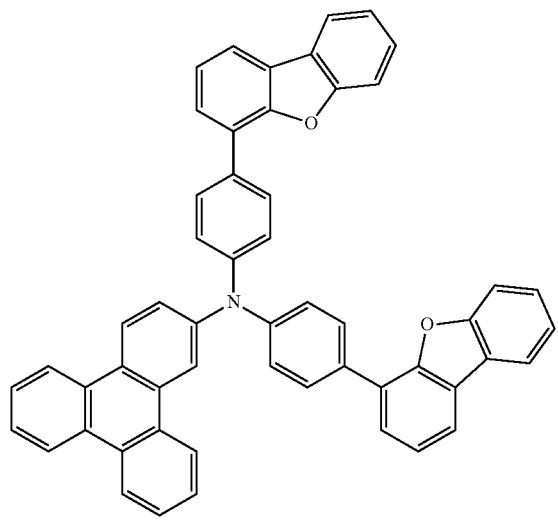
56
-continued
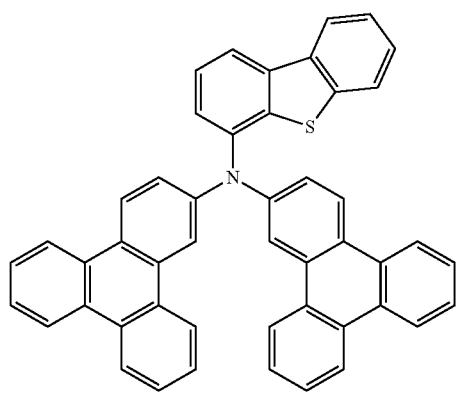
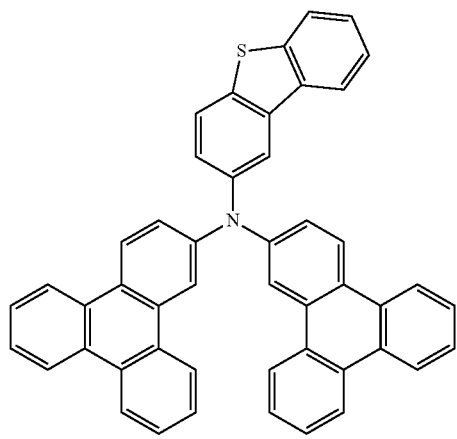
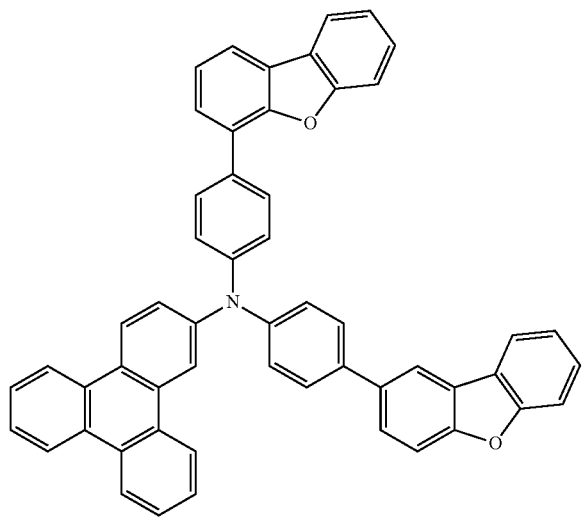

-continued
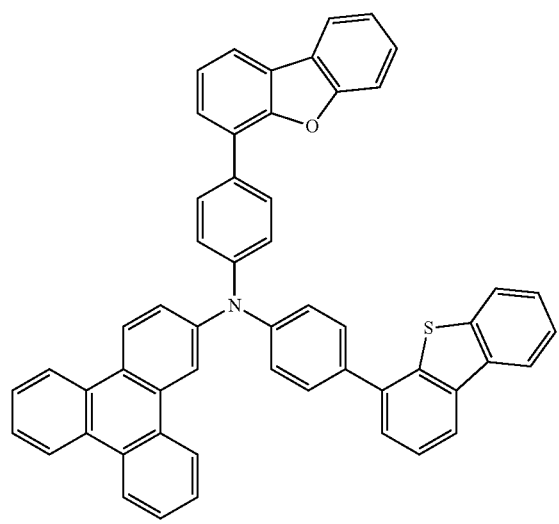
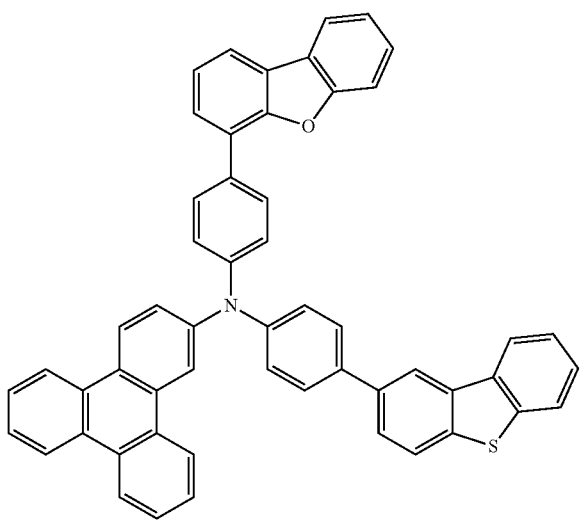
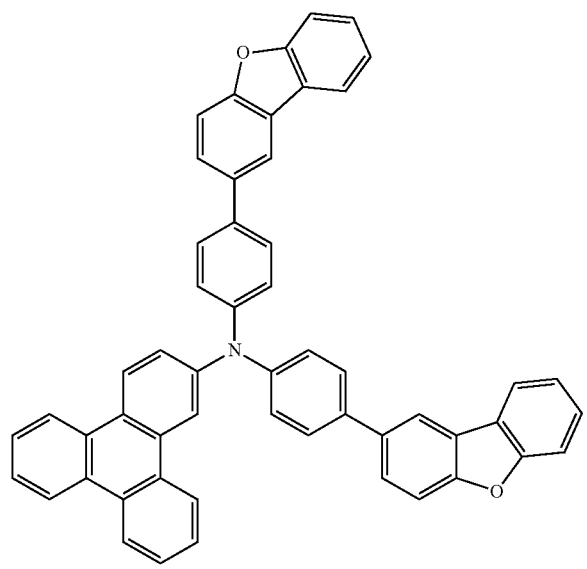
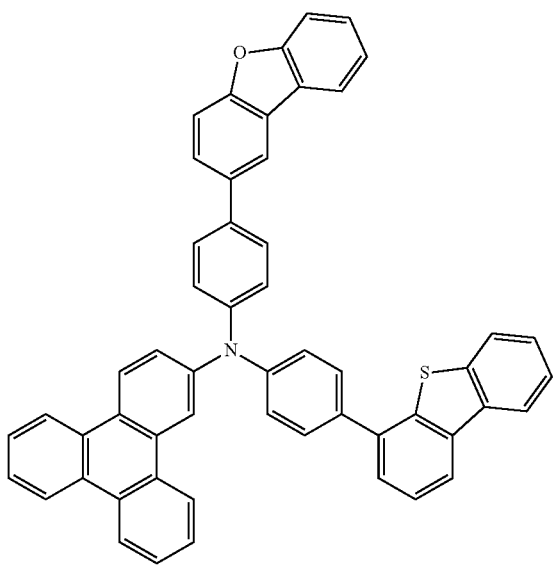
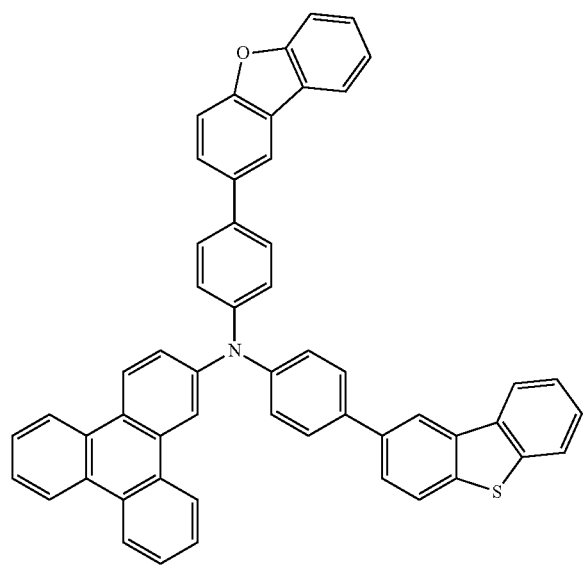
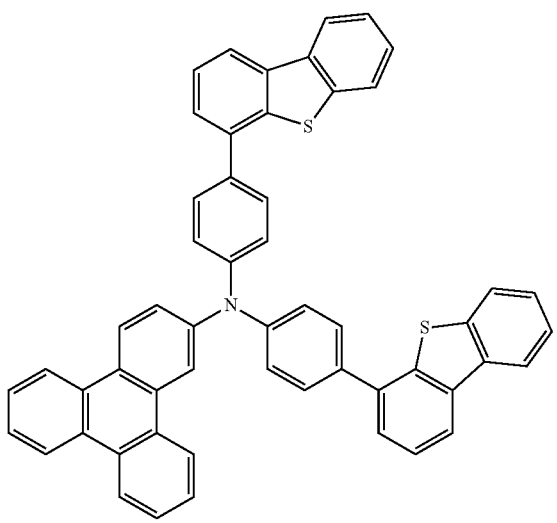

-continued
| 59 | 60 |
|---|---|
| 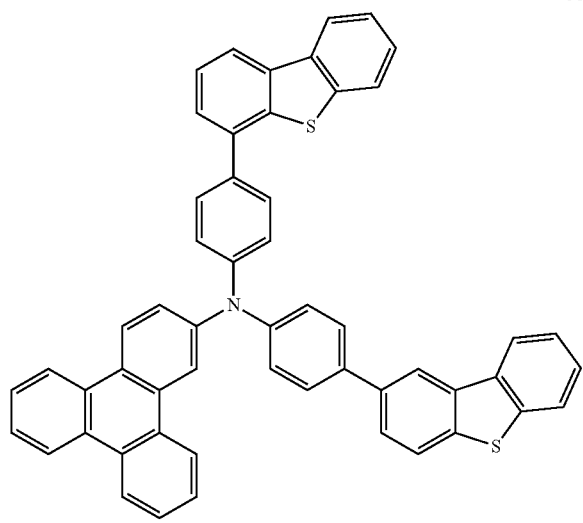 | 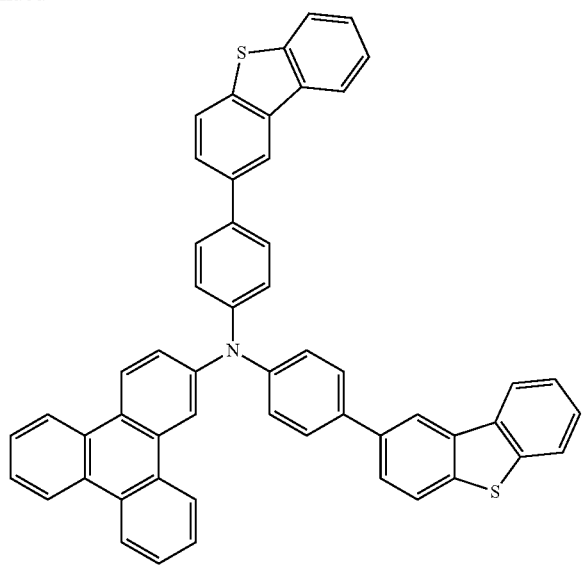 |
| 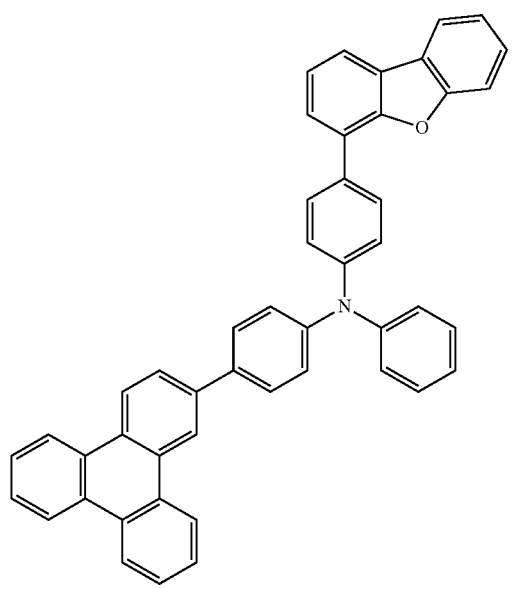 | 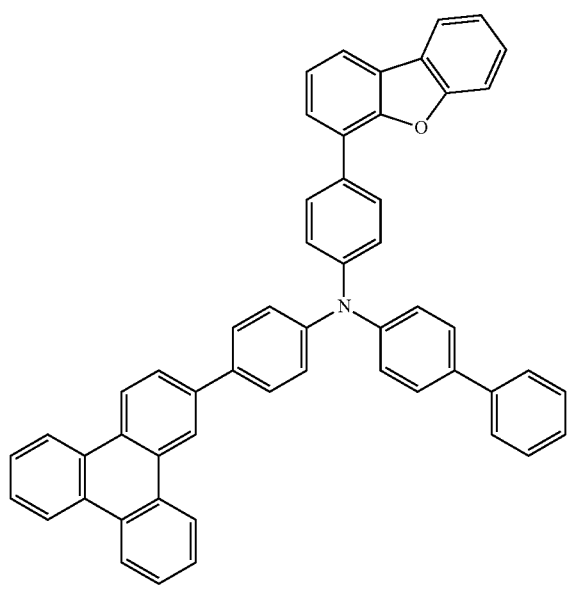 |
| 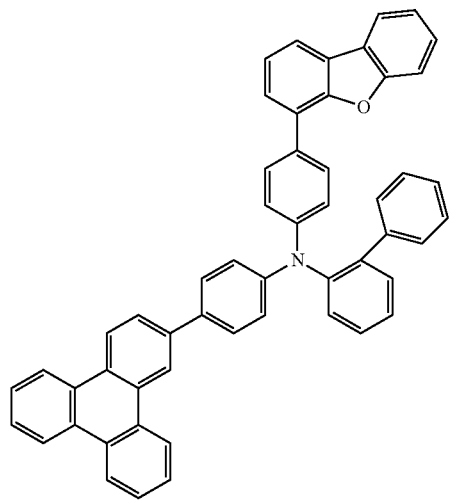 | 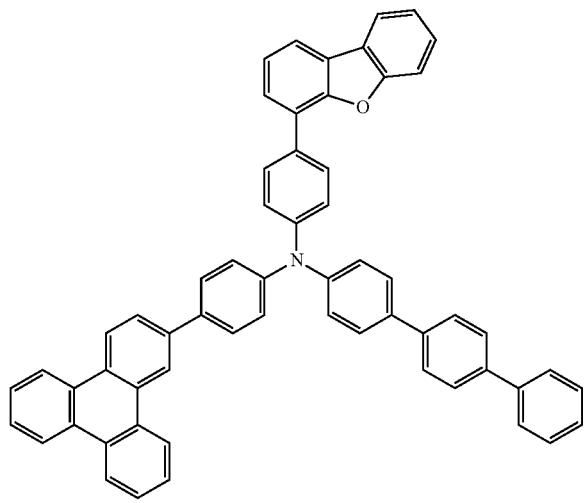 |

-continued
61
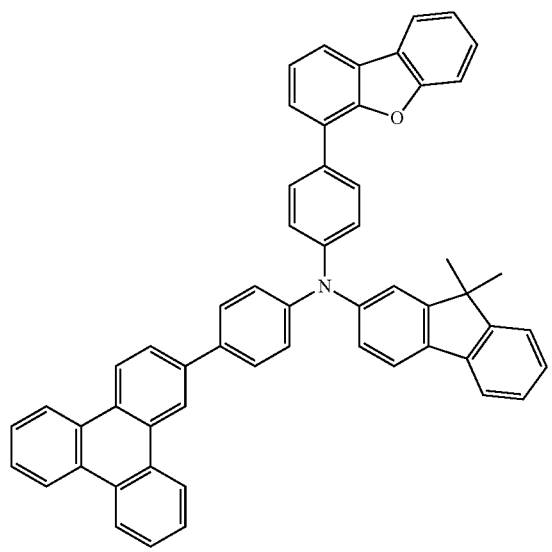
62
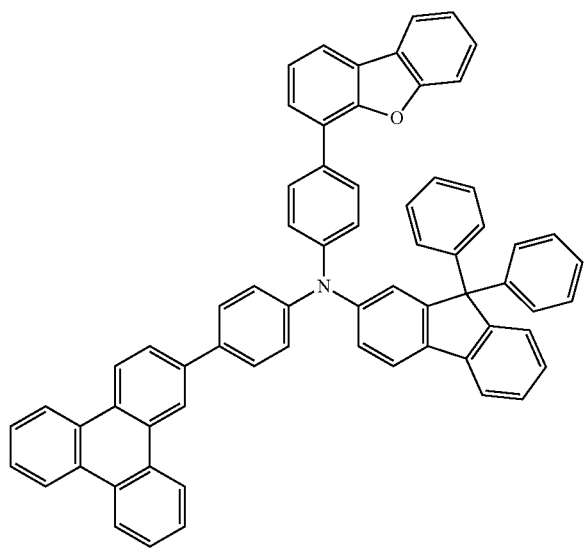
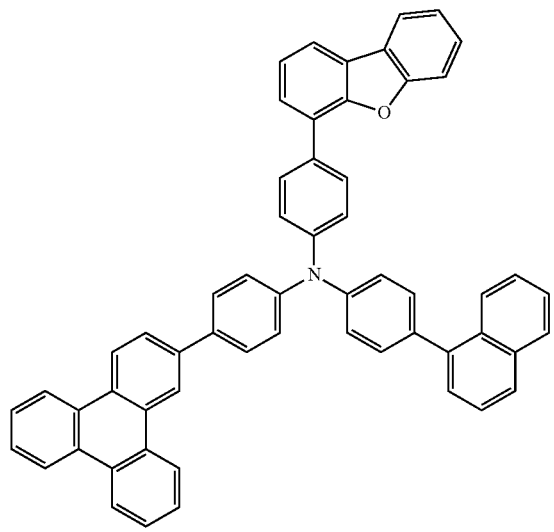
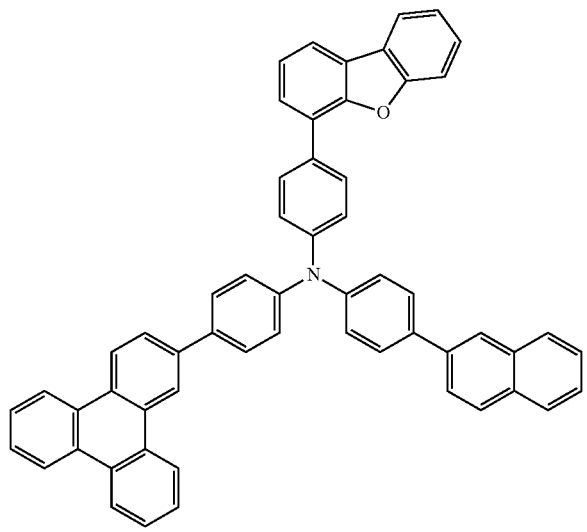
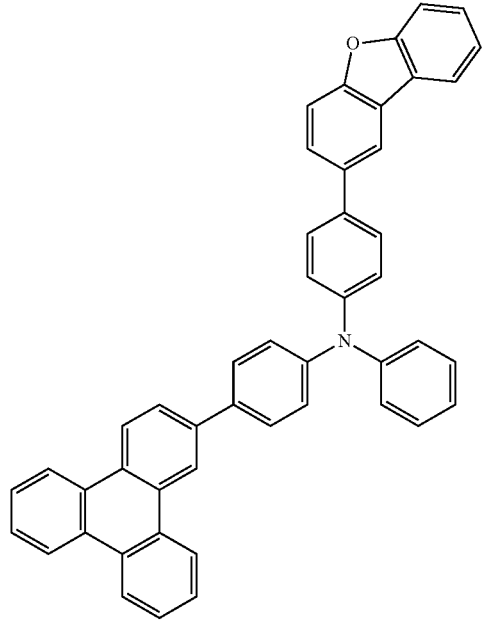
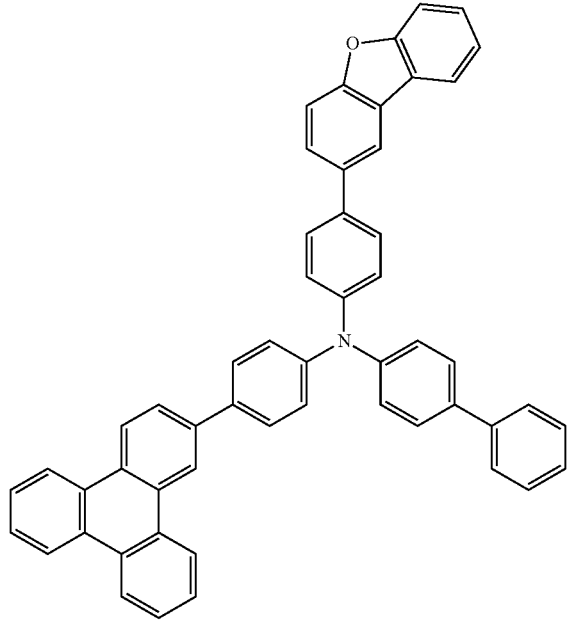

63
64
-continued
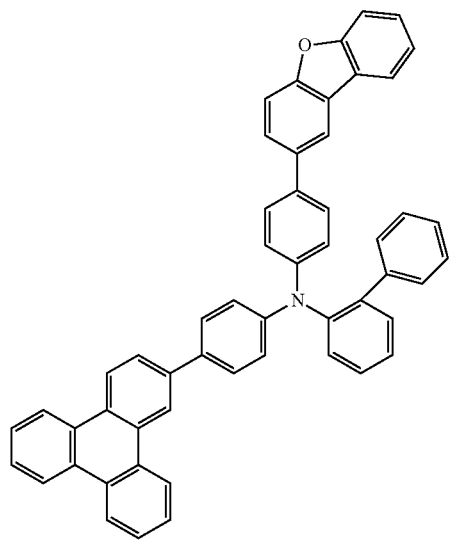
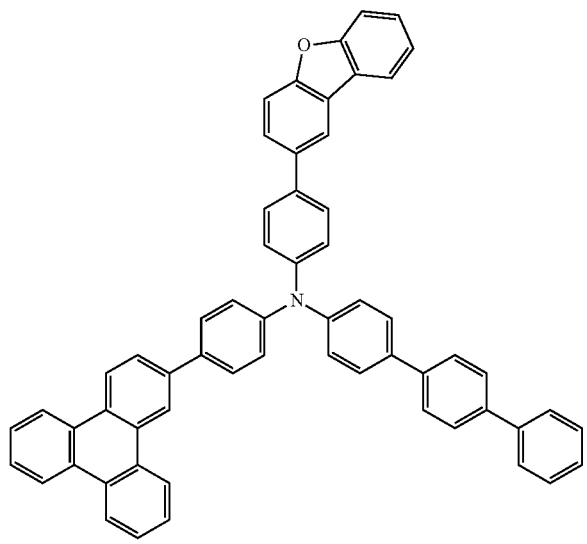
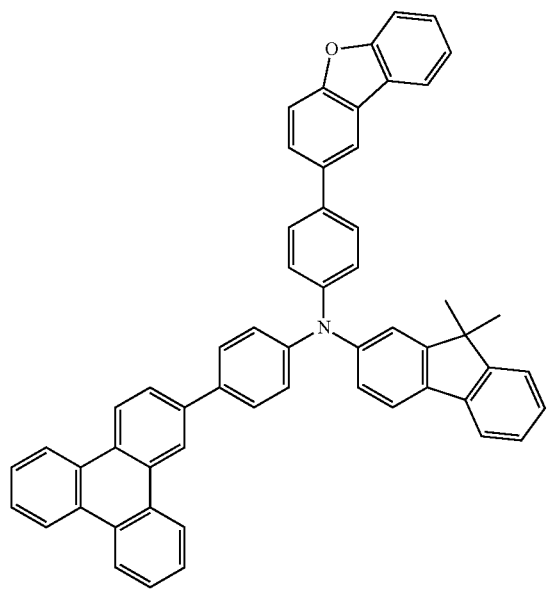
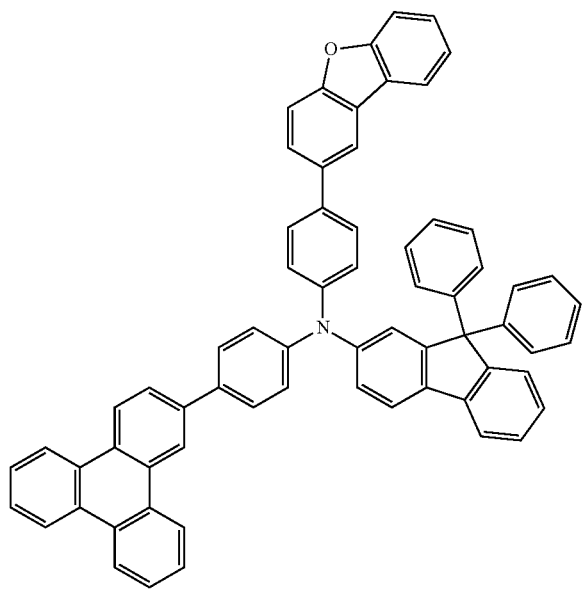
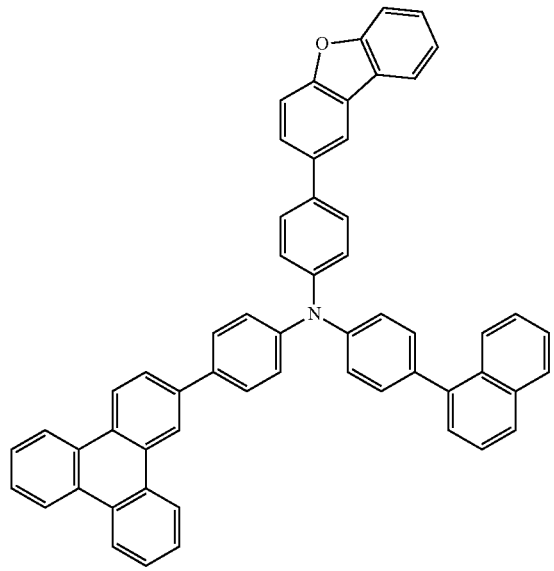
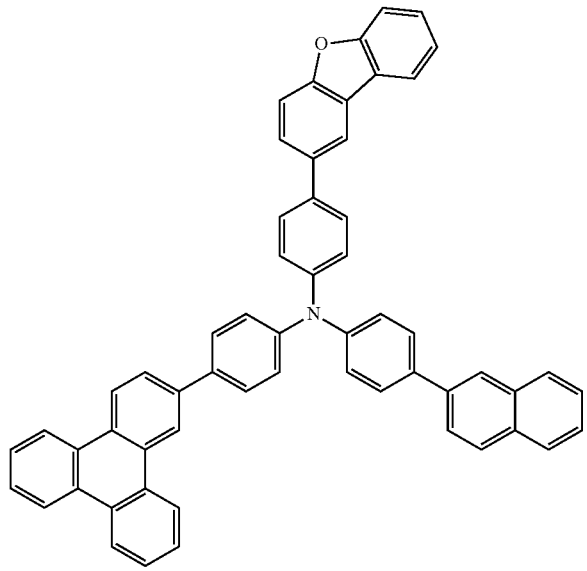

-continued
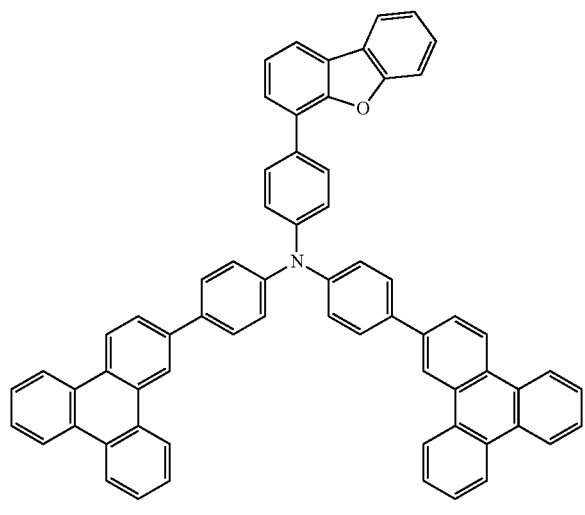
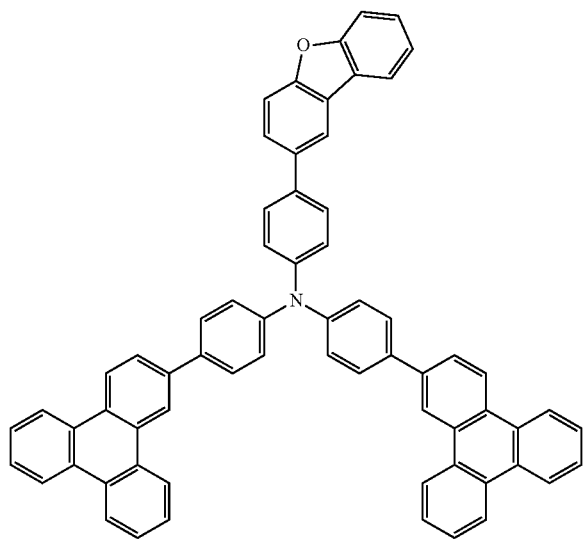
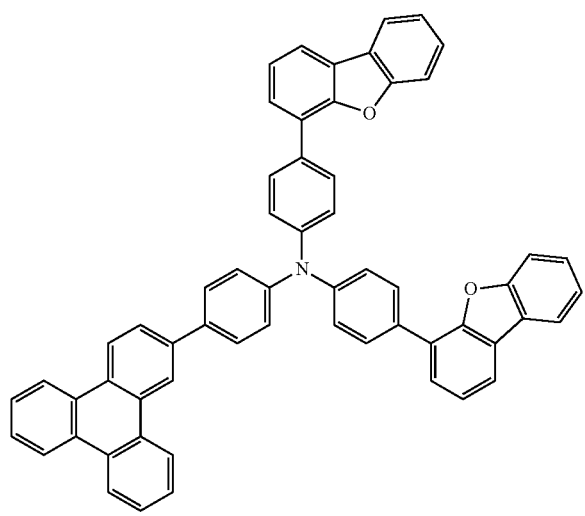
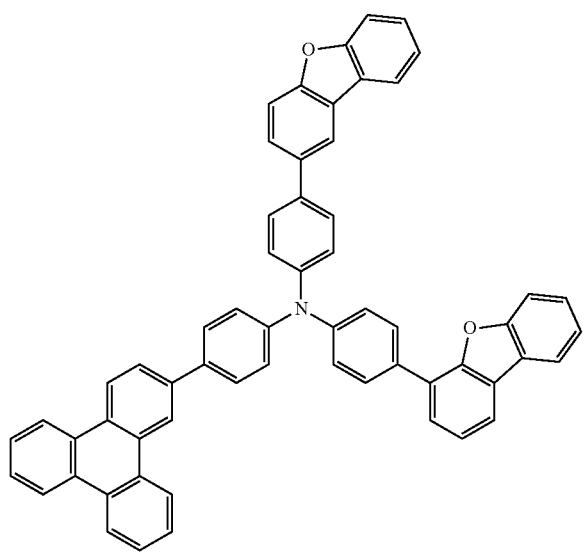
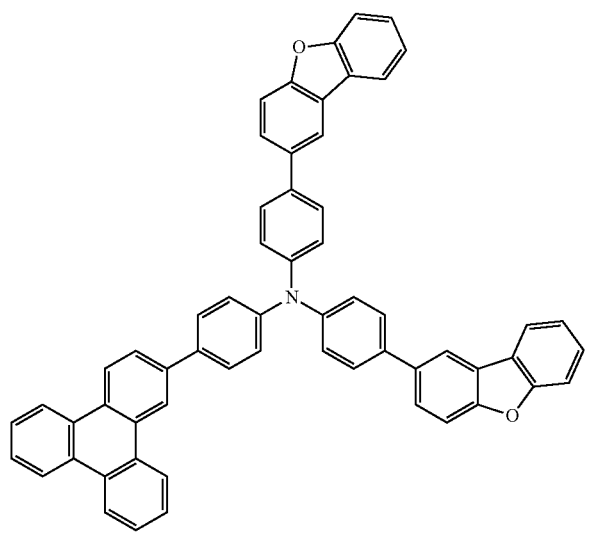
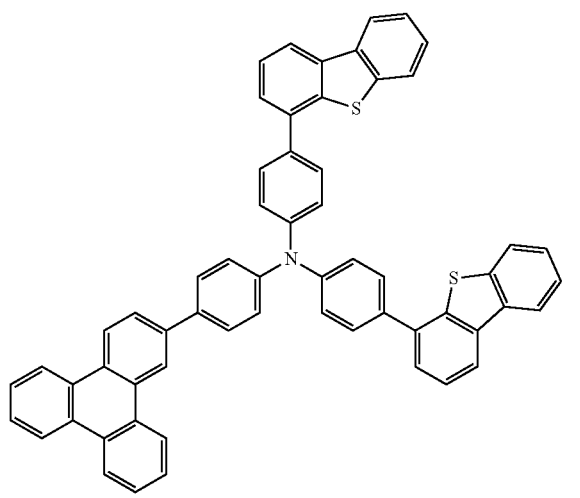

67
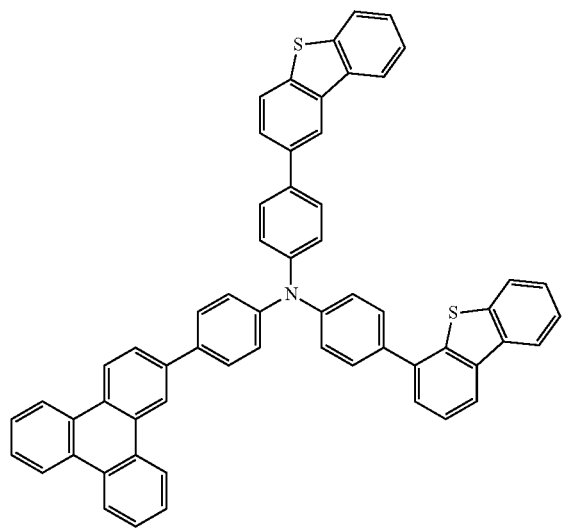
68
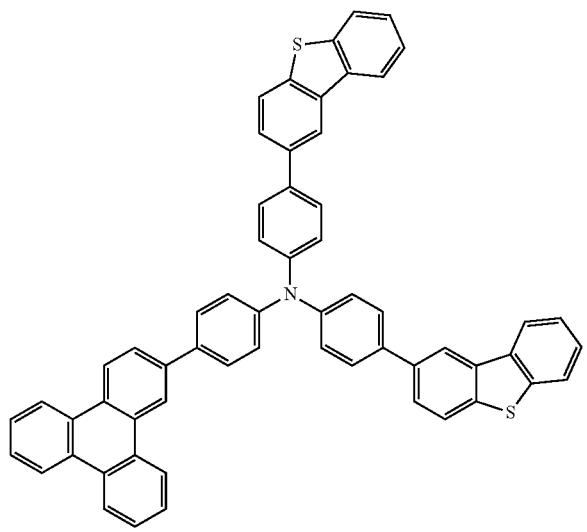
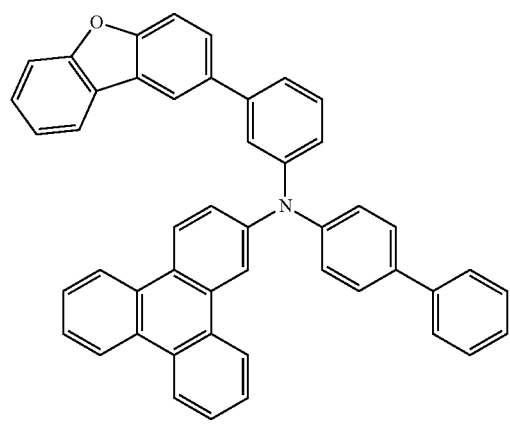
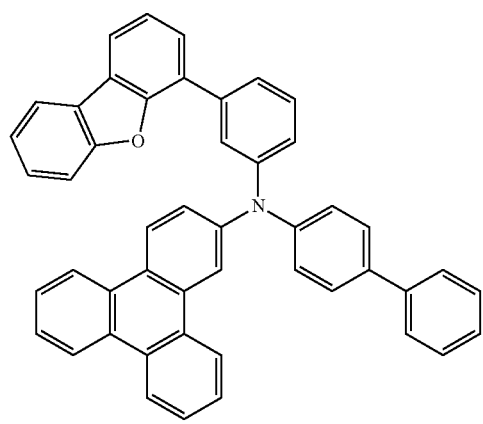
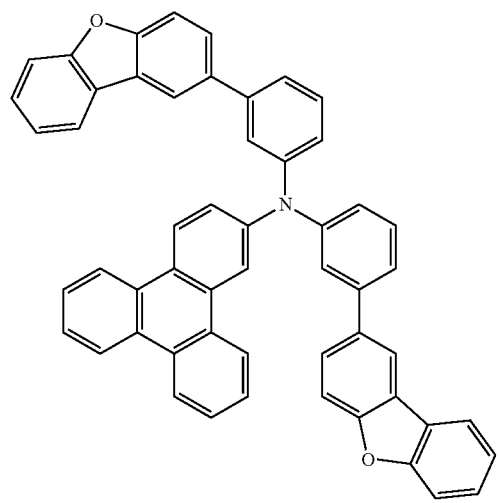
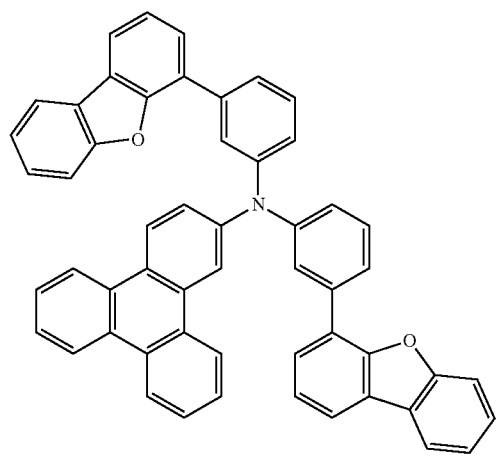

69 70
-continued
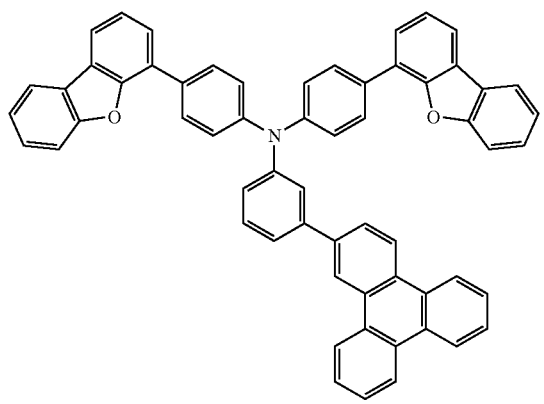
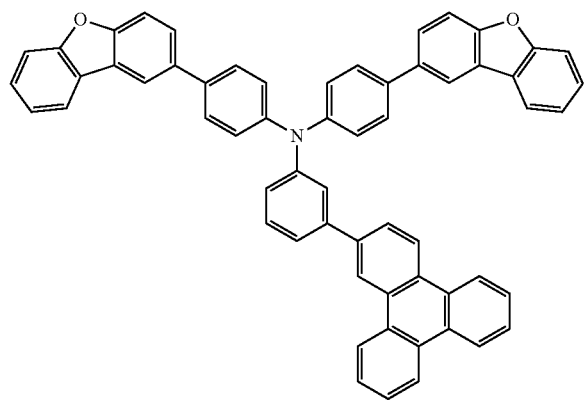
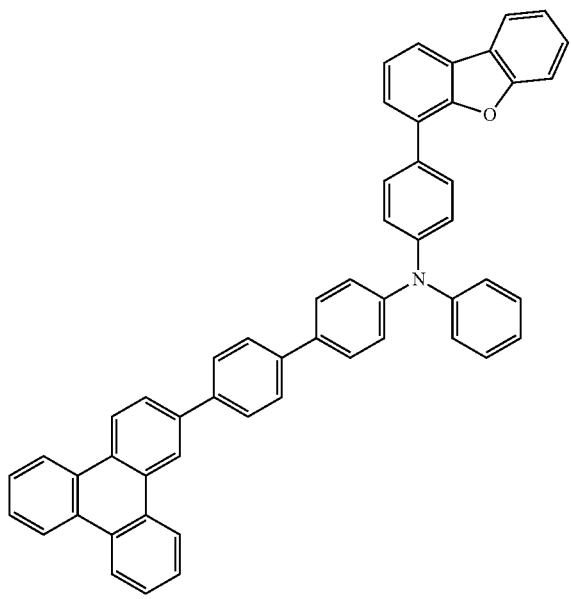
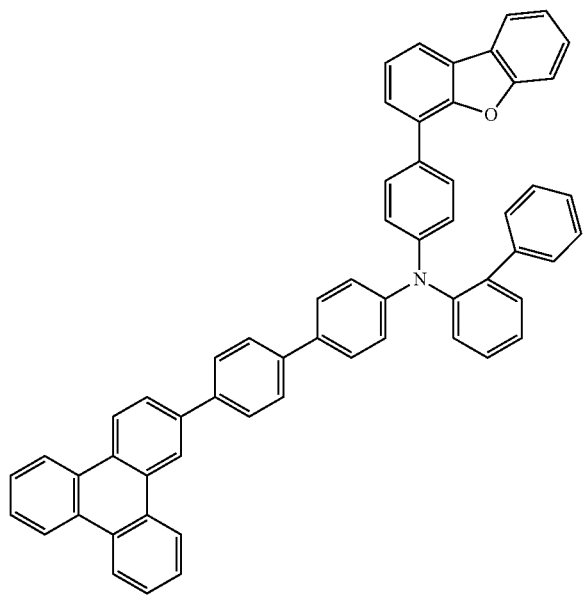
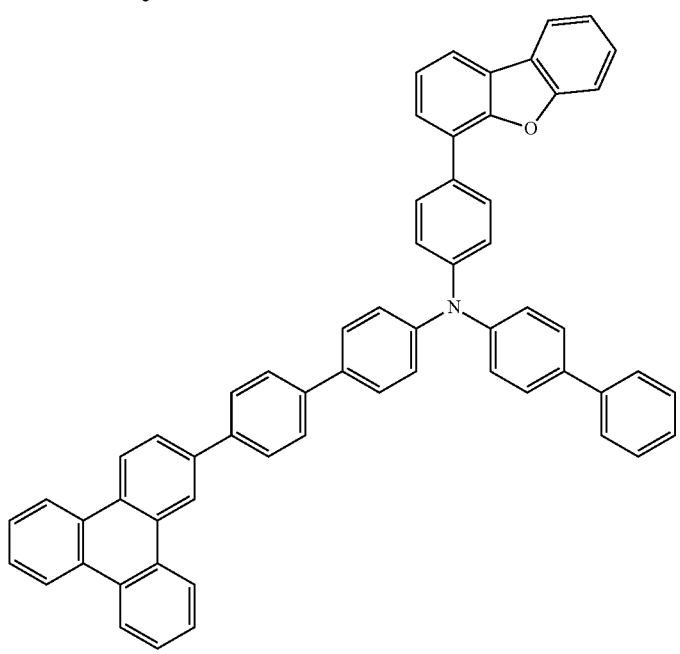

-continued
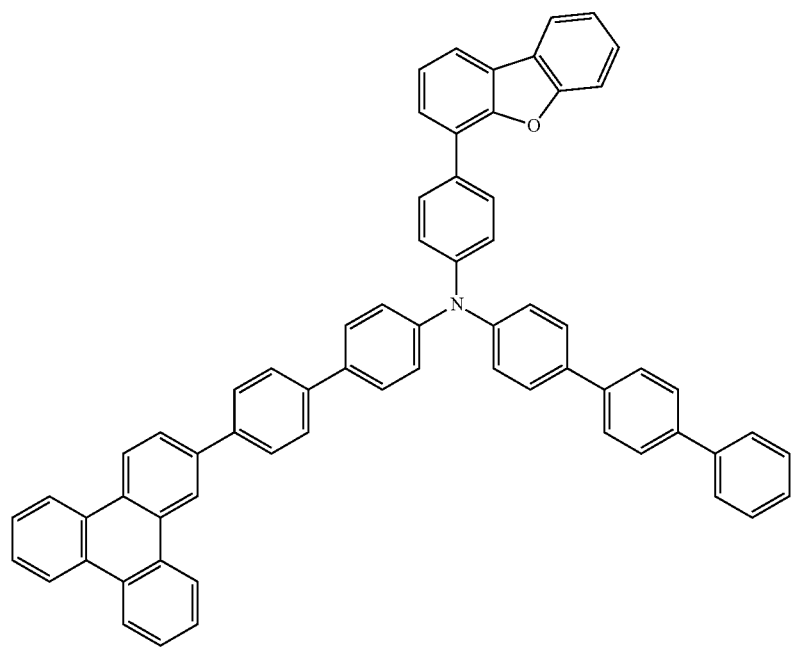
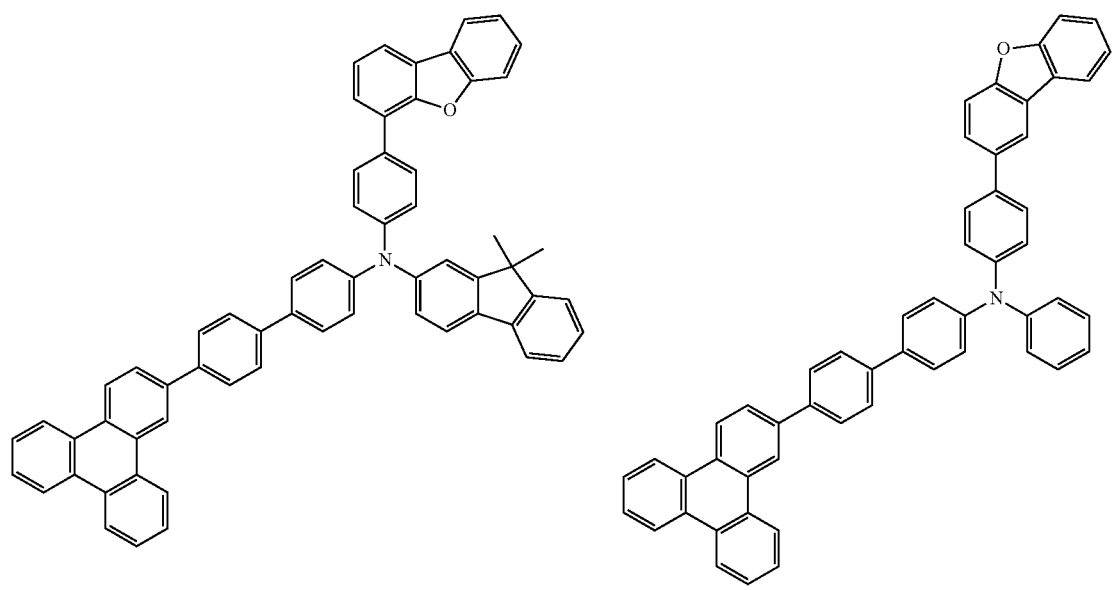

| 73 | 74 |
|---|---|
| 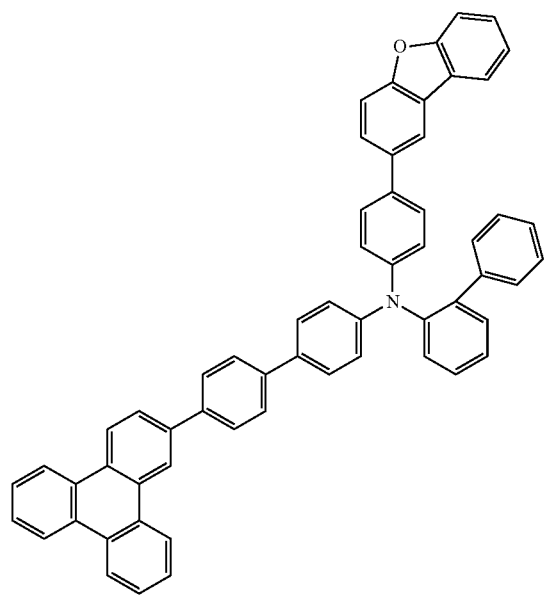 | 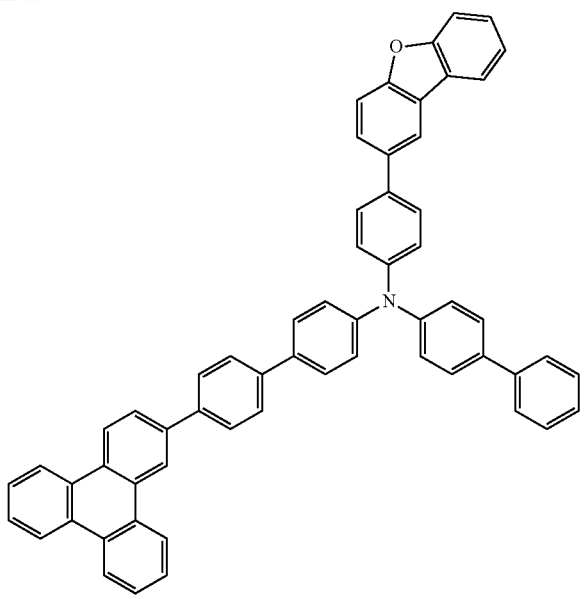 |
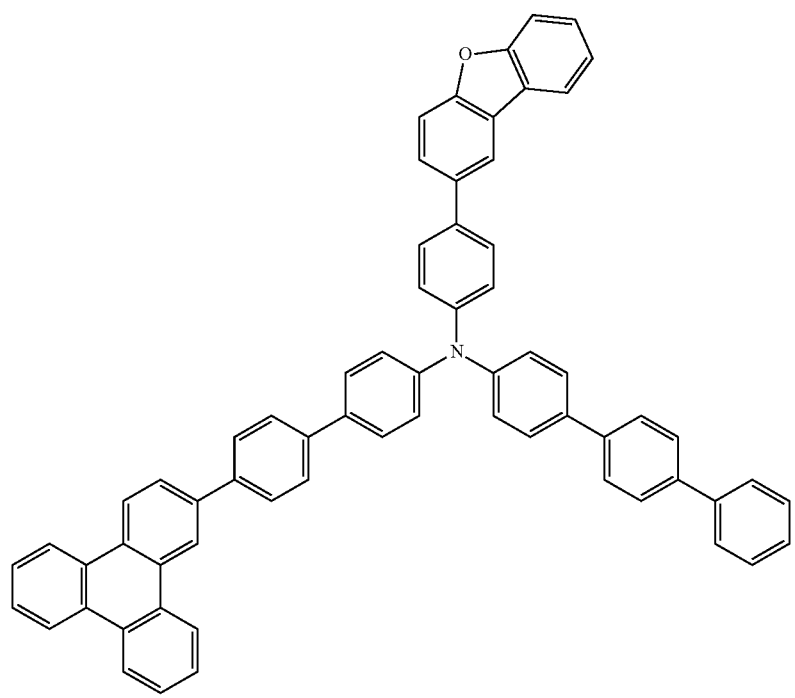

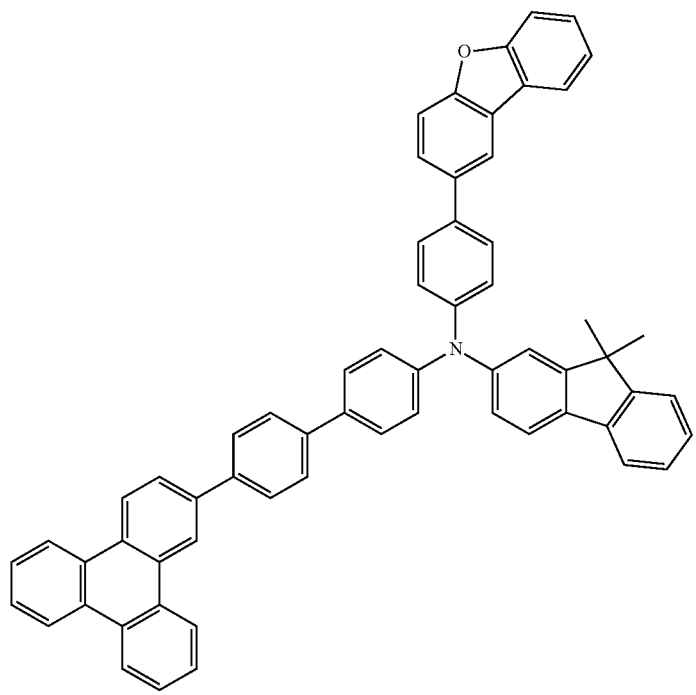
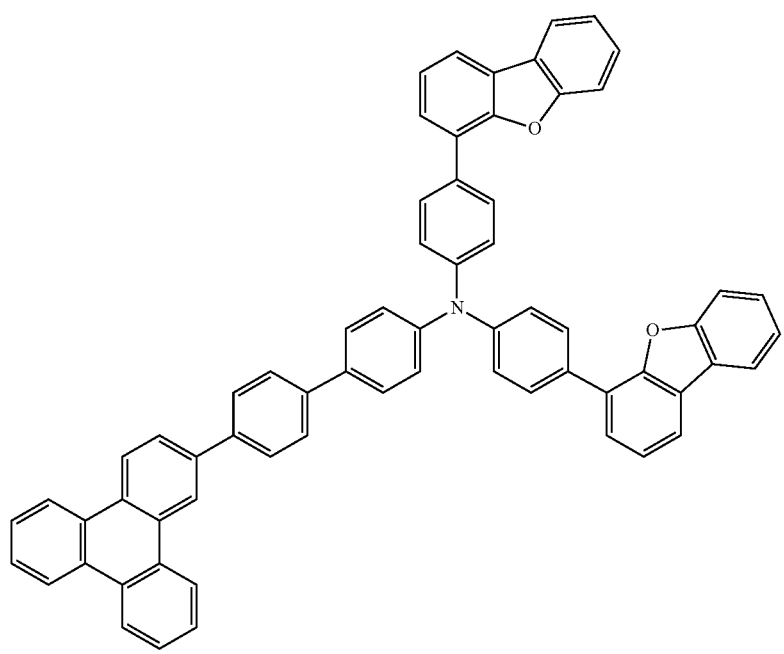

-continued
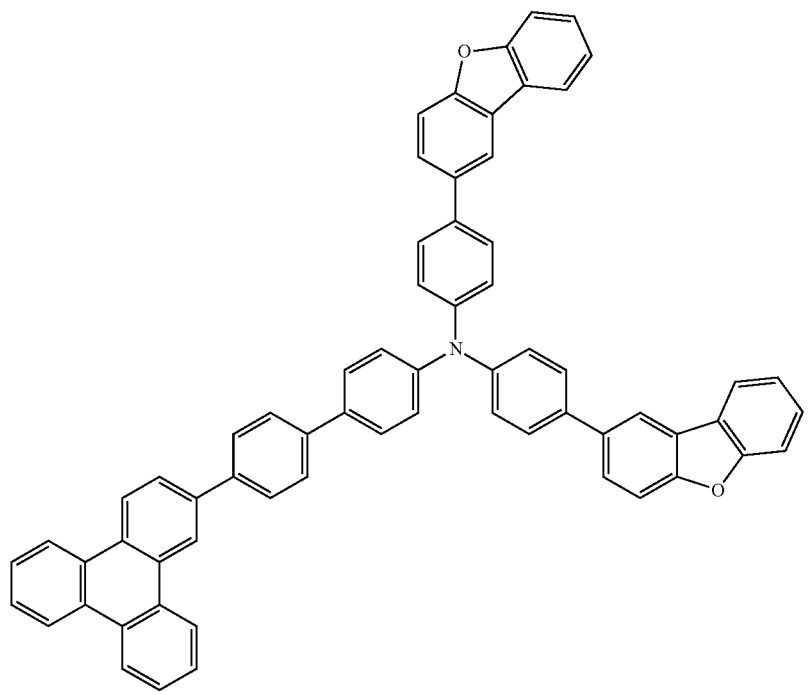

-continued
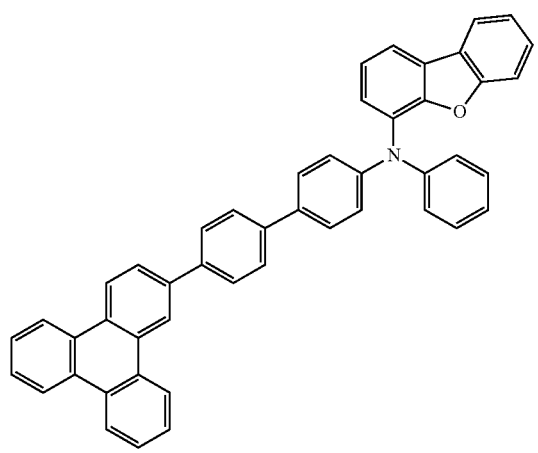
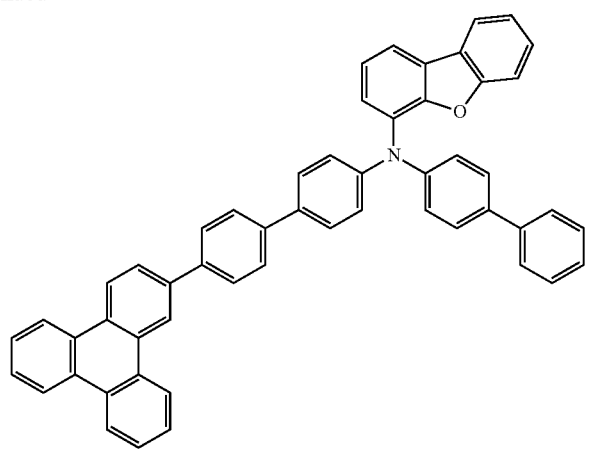
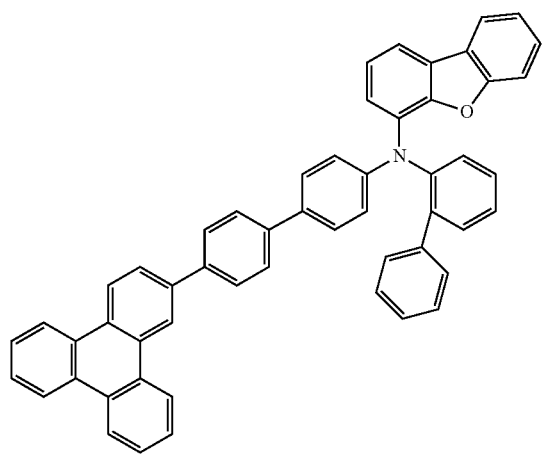
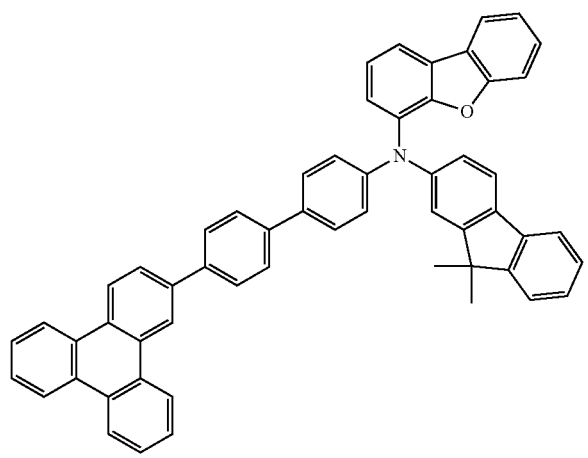
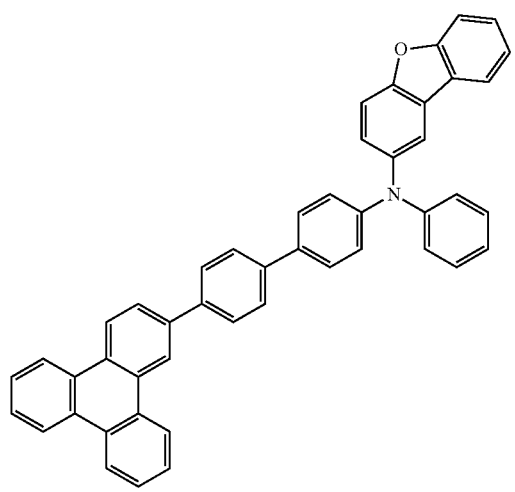
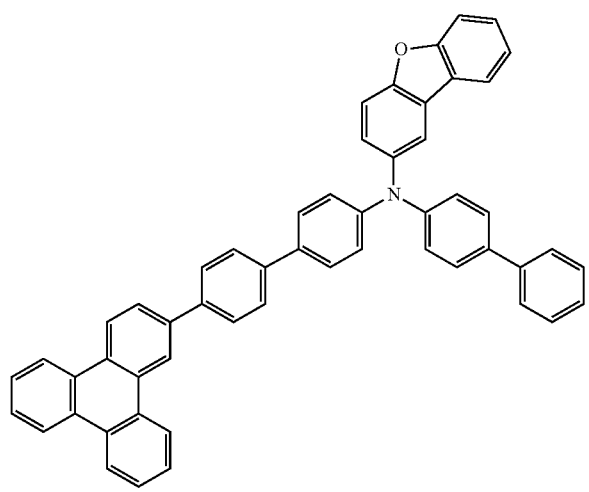

81 82
-continued
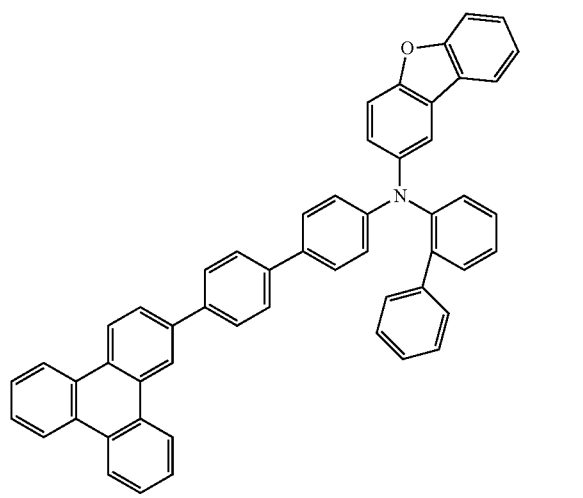
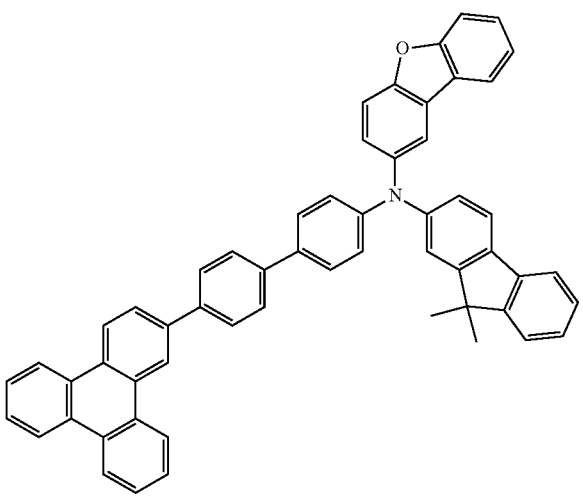
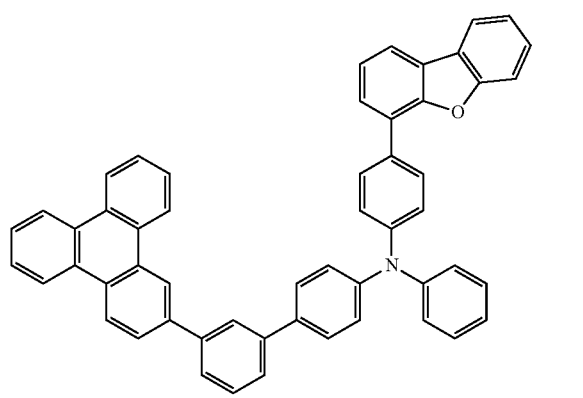
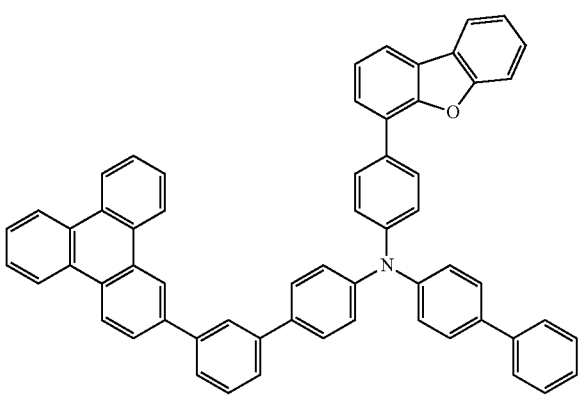
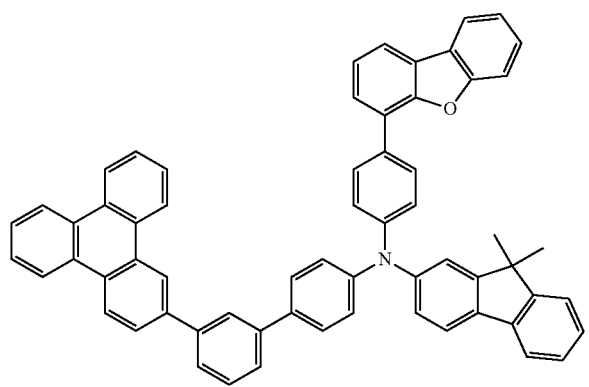
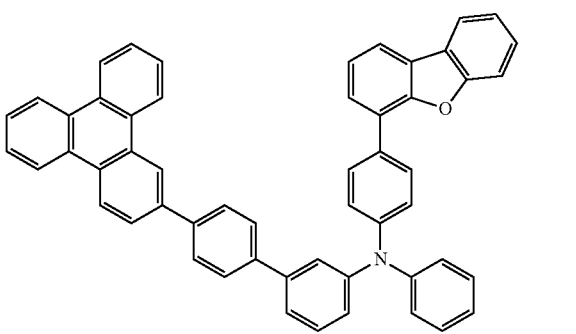
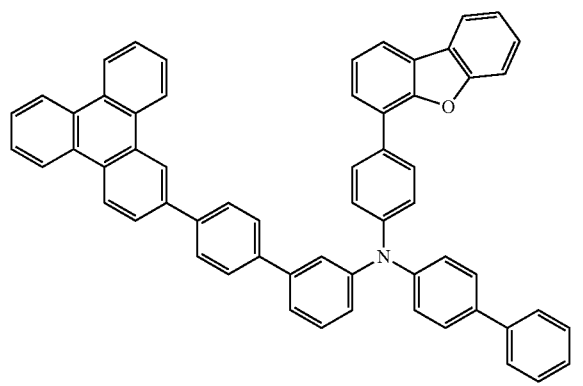
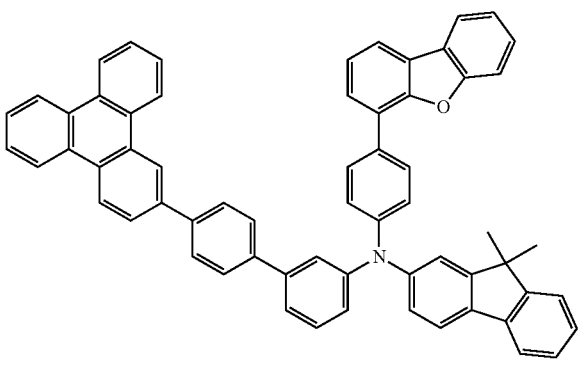

83
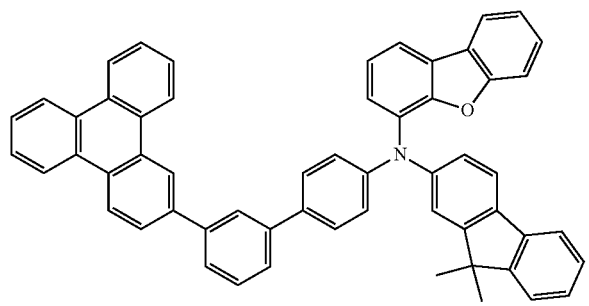
84
-continued
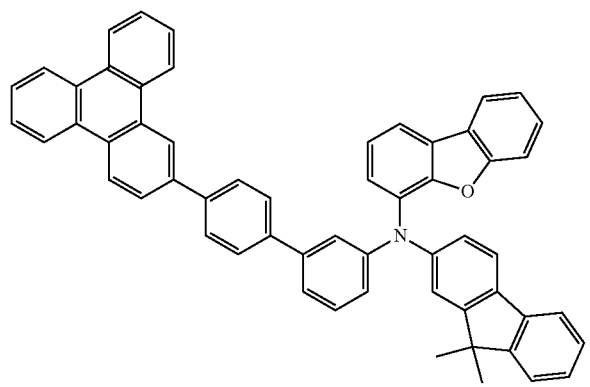
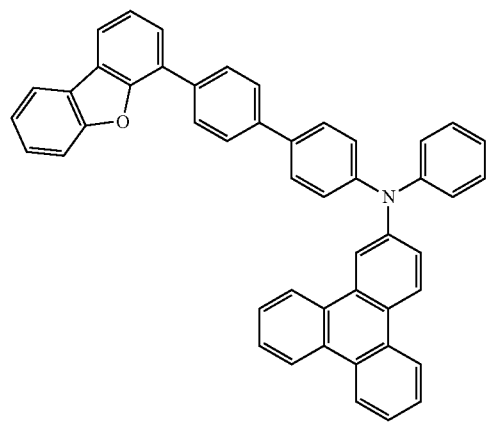
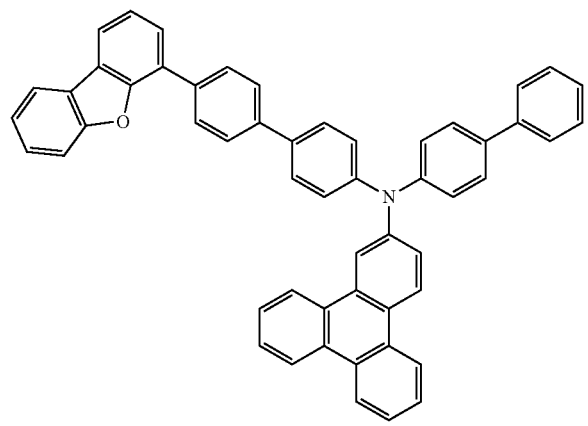
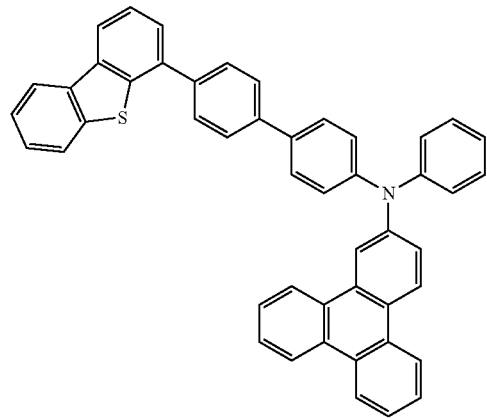
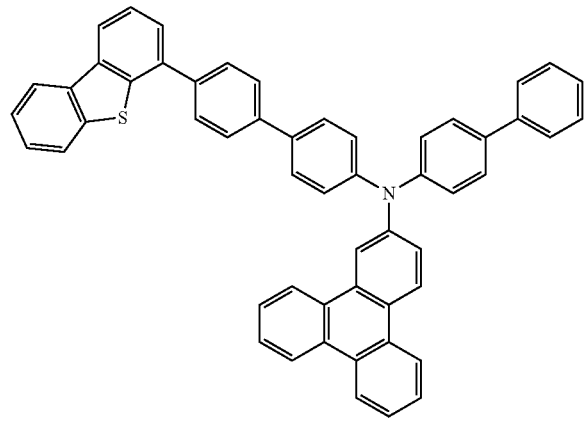
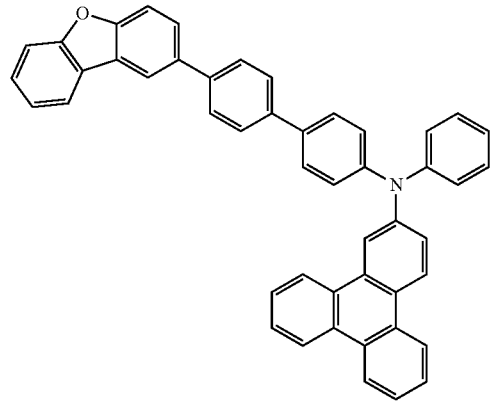
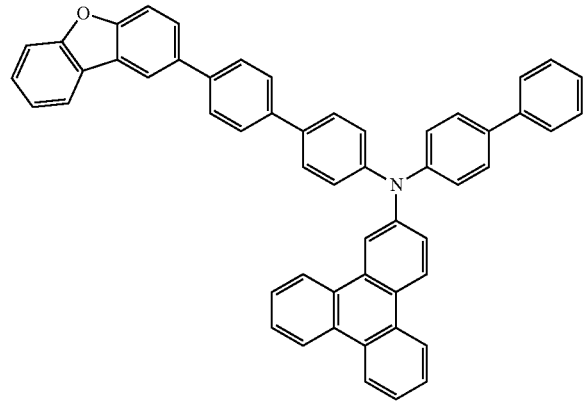

-continued
85
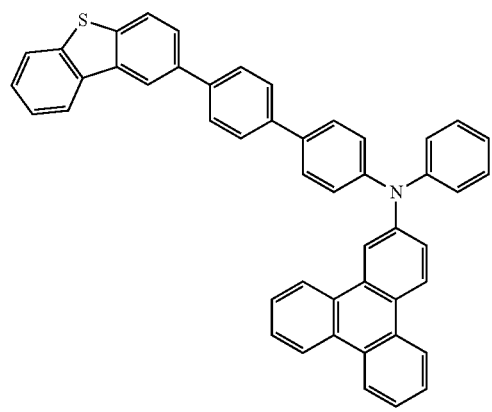
86
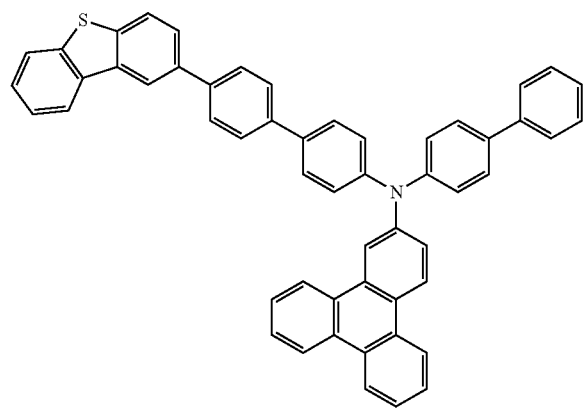
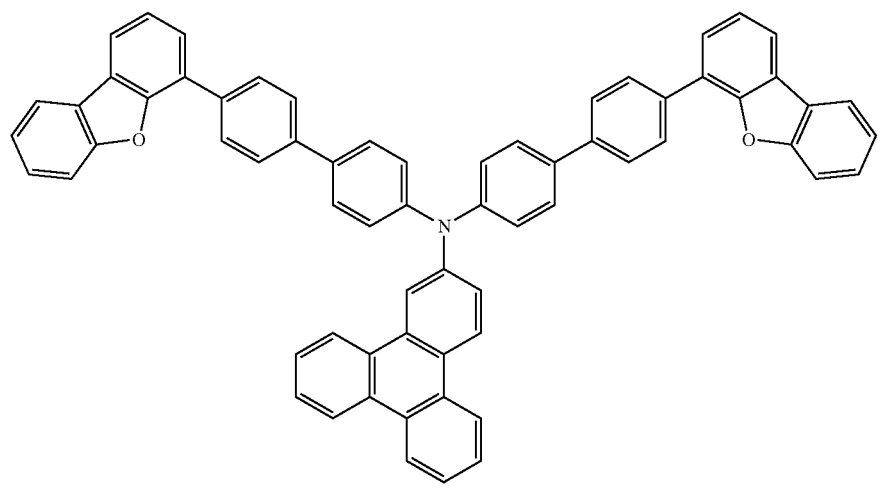
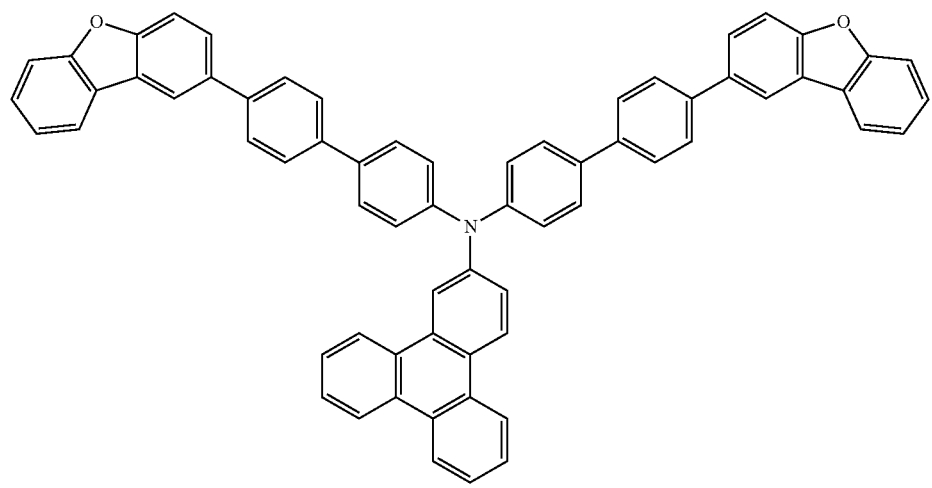

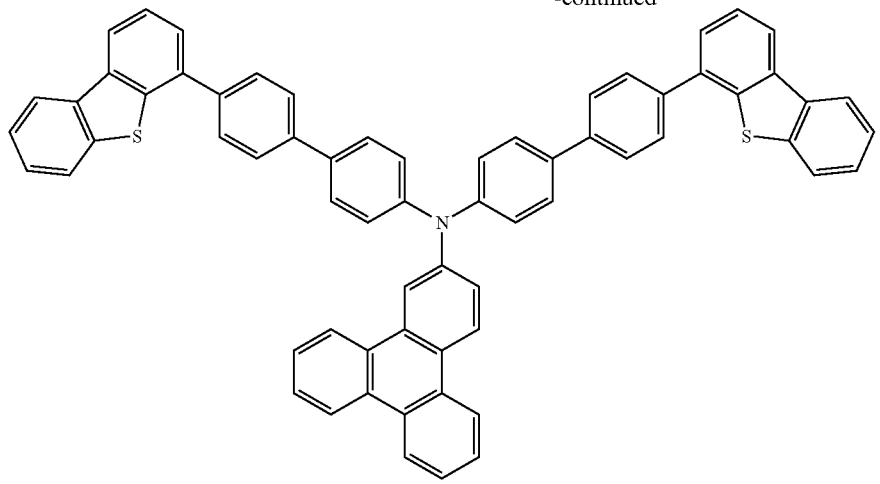
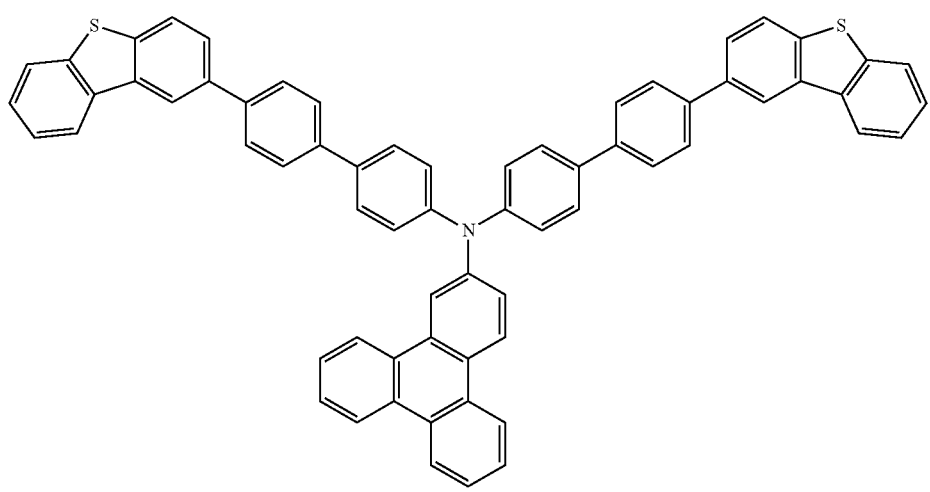
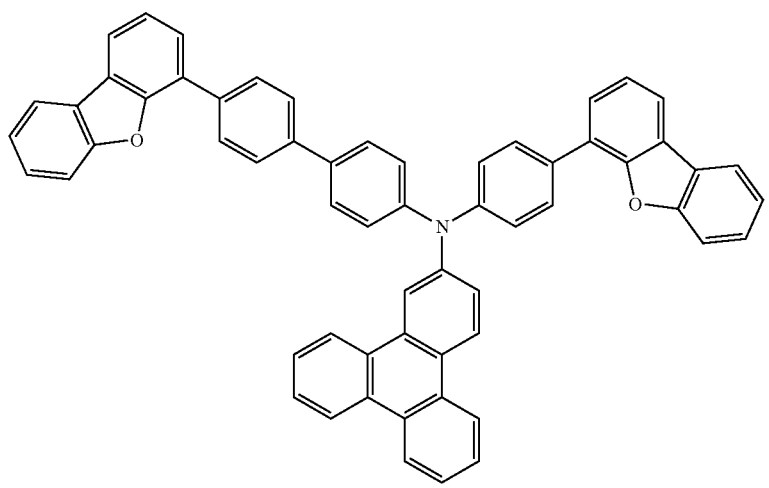

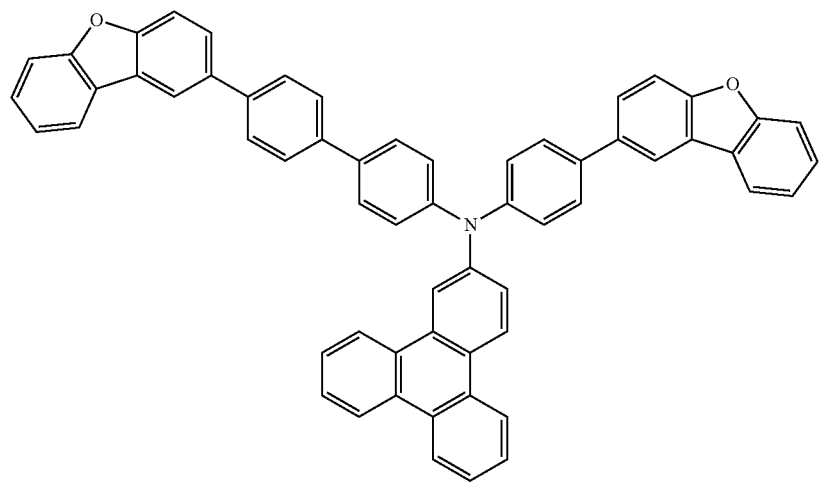
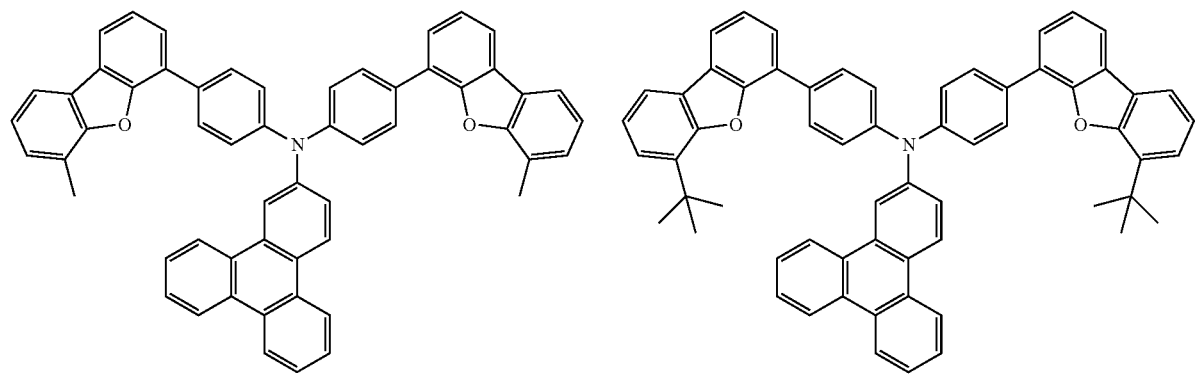
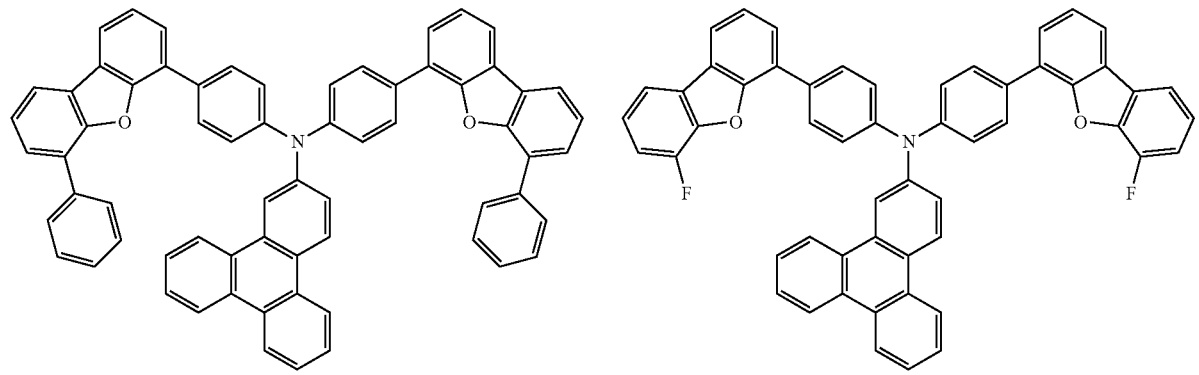
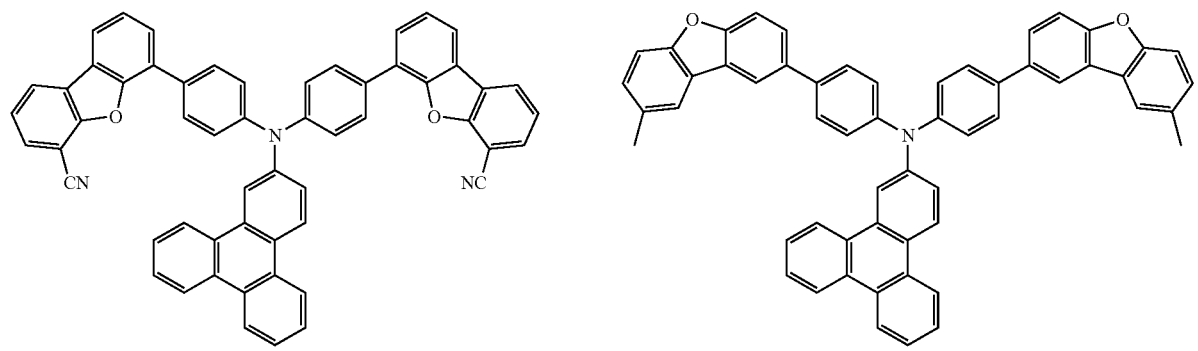

91 92
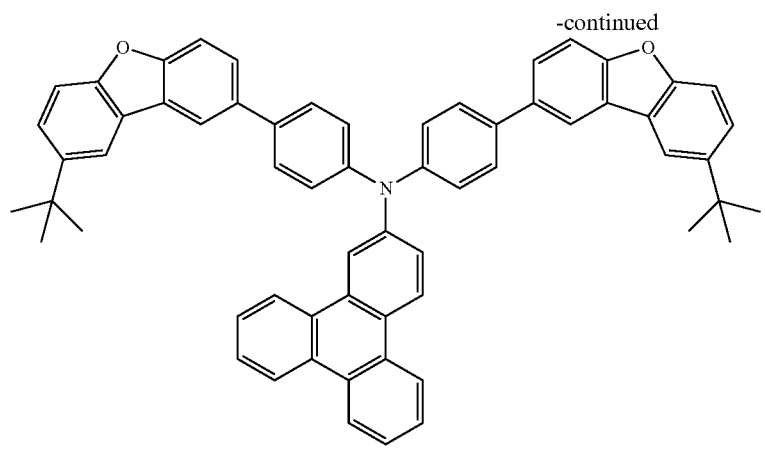
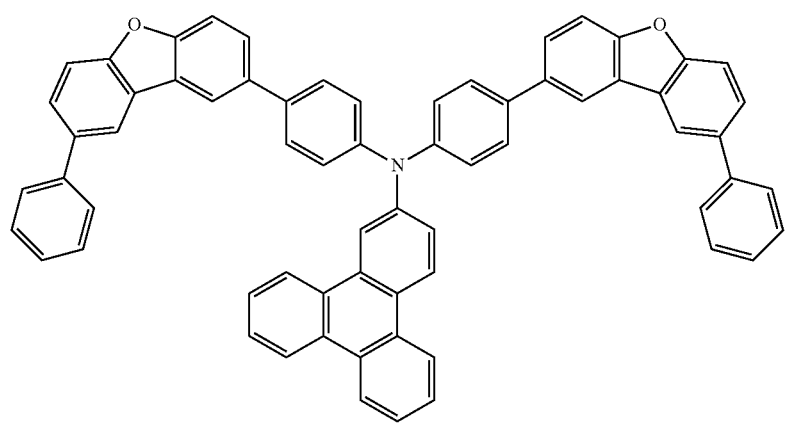
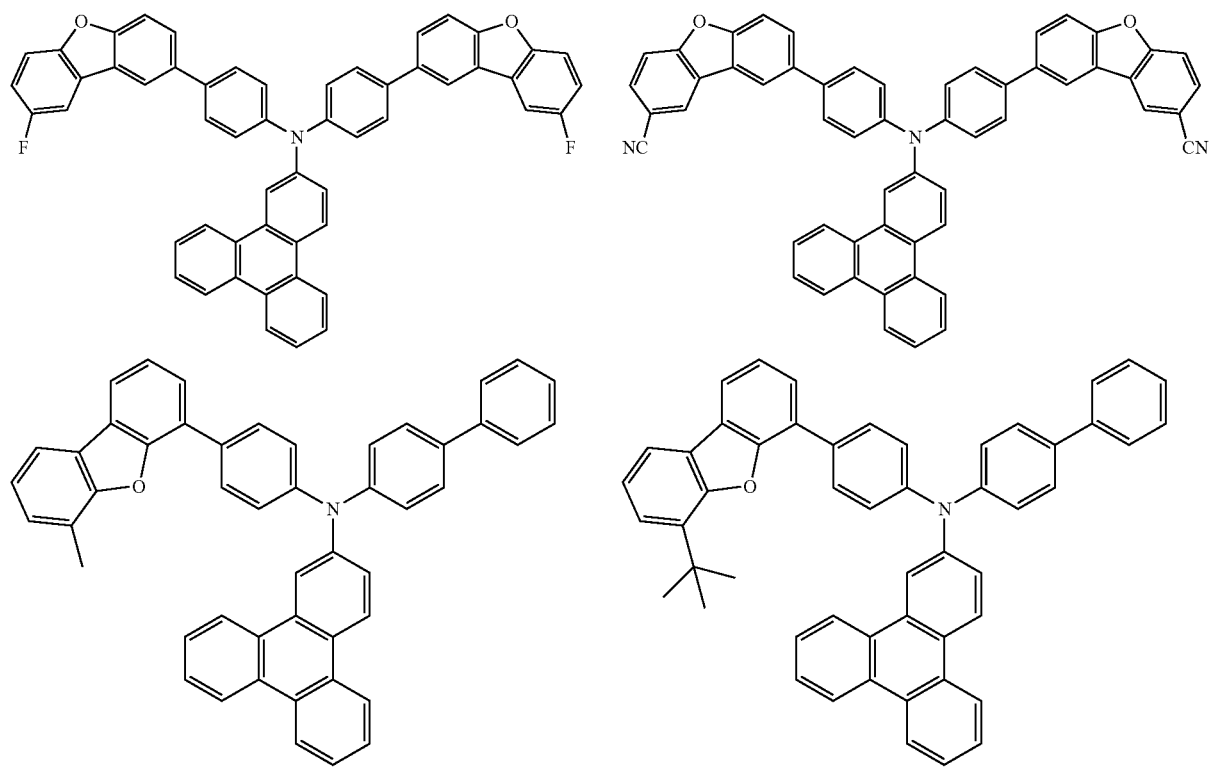

-continued
93
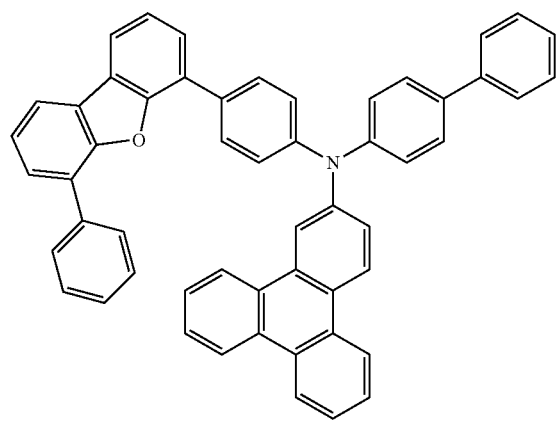
94
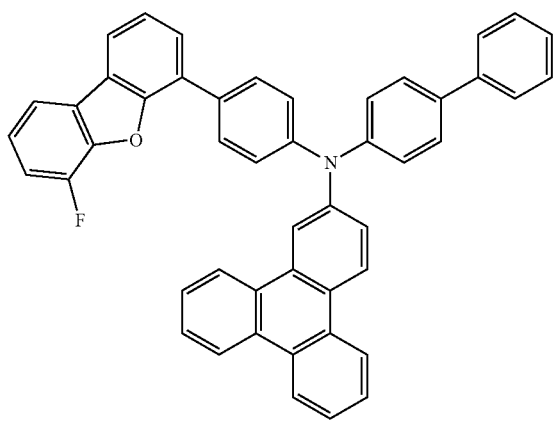
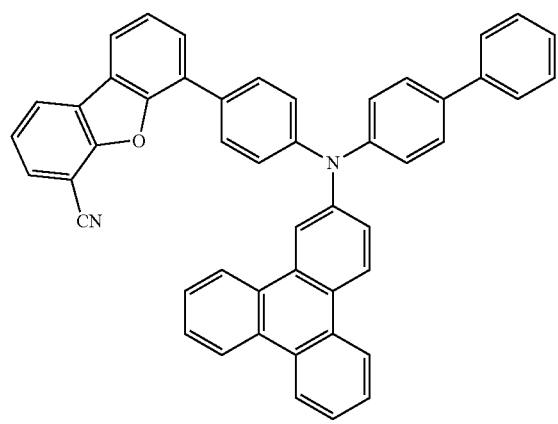
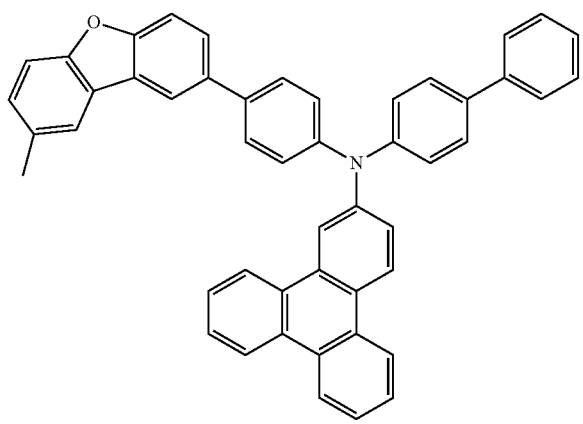
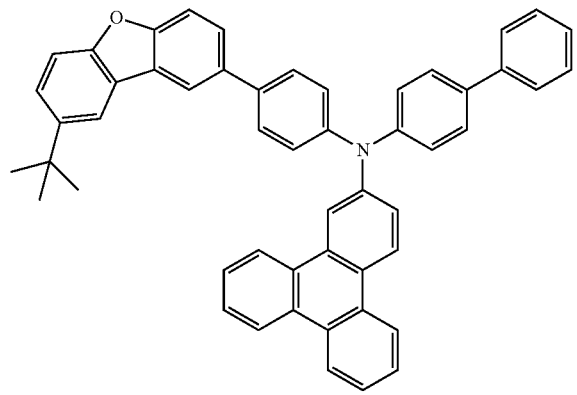
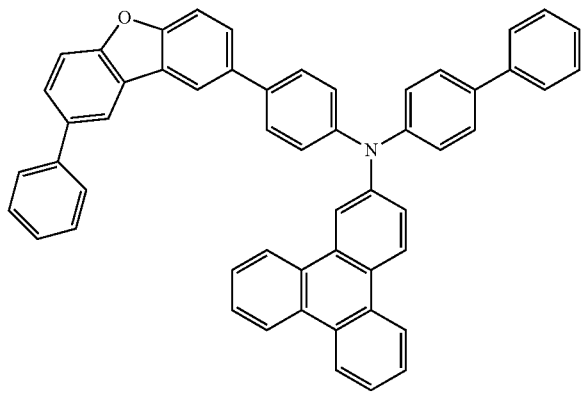
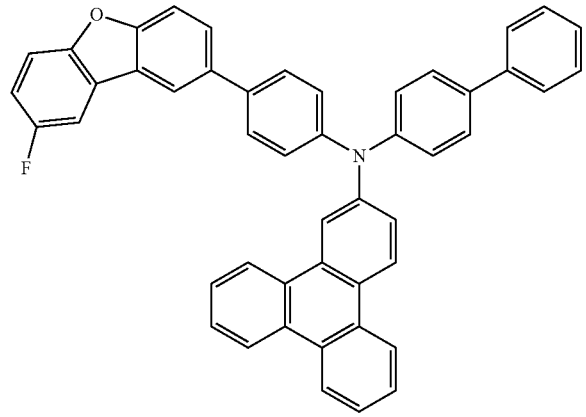
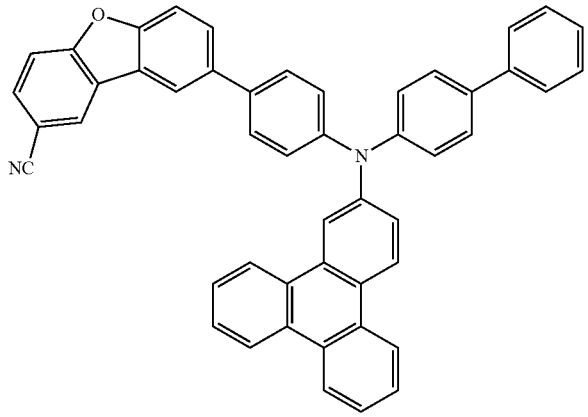

The aromatic amine derivative represented by formula (1) is useful as a material for an organic EL device, in particular, as a hole injecting layer material or a hole transporting layer material. The production method of the aromatic amine derivative of the invention is not particularly limited and one of ordinary skill in the art could easily produce it by utilizing or modifying known synthesis reactions while referring to the examples described below.

The structure of the organic EL device of the invention will be described below.

Examples of the typical device structure of the organic EL device of the invention include the following (1) to (13), although not particularly limited thereto. The device structure (8) is preferably used.

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting layer/hole transporting layer/light emitting layer/(electron transporting layer/)electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/(electron transporting layer/)electron injecting layer/cathode.

Since the aromatic amine derivative of the invention hardly crystallizes, it can be used in any of the above organic thin film layers. In view of driving at a lower voltage, the aromatic amine derivative is preferably contained in a hole injecting layer or a hole transporting layer and more preferably in a hole transporting layer. The organic EL device employing the aromatic amine derivative of the invention is not only capable of driving at a low voltage but also has a high emission efficiency and a long lifetime.

The content of the aromatic amine derivative in an organic thin film layer, preferably in a hole injecting layer or a hole transporting layer is preferably 30 to 100 mol %, more preferably 50 to 100 mol %, still more preferably 80 to 100 mol %, and particularly preferably substantially 100 mol %, each based on the total components of the organic thin film layer.

Each layer of a preferred embodiment of an organic EL device wherein the aromatic amine derivative of the invention is used in a hole transporting layer is described below.

Substrate

The organic EL device is generally formed on a light-transmissive substrate. The light-transmissive substrate is a substrate for supporting the organic EL device, which preferably has a light transmittance of 50% or higher to 400 to 700 nm visible lights and is preferably flat and smooth.

Examples of the light-transmissive substrate include glass plates and synthetic resin plates. Examples of the glass plate include plates of soda-lime glass, glass containing barium and strontium, lead glass, aluminosilicate glass, borosilicate glass, barium borosilicate glass, and quartz. Examples of the synthetic resin plate include plates of a polycarbonate resin, an acrylic resin, a polyethylene terephthalate resin, a polyether sulfide resin, and a polysulfone resin.

Anode

The anode has a function of injecting holes to a hole transporting layer or a light emitting layer and a material having a work function of 4 eV or more, preferably 4.5 eV or more is effective. Examples of the material for the anode include carbon, aluminum, vanadium, iron, cobalt, nickel, tungsten, silver, gold, platinum, palladium, alloys thereof, metal oxides, such as tin oxide and indium oxide, which have been used as ITO substrate and NESA substrate, and organic conductive resins, such as polythiophene and polypyrrole.

The anode may be formed by making the above anode material into a thin film, for example, by a vapor deposition method or a sputtering method.

When the light emitted from the light emitting layer is taken through the anode, the transmittance of the anode to the emitted light is preferably higher than 10%. The sheet resistance of the anode is preferably several hundred Ω/□ or smaller. The thickness of the anode is generally 10 nm to 1 μm and preferably 10 to 200 nm, although varies depending upon the used material.

Cathode

The cathode is formed from an electrode material, such as a metal, an alloy, an electroconductive compound, or a mixture thereof, each having a small work function (less than 4 eV). Examples thereof include magnesium, calcium, tin, lead, titanium, yttrium, lithium, ruthenium, manganese, aluminum, lithium fluoride, and alloys thereof, although not particularly limited thereto. Examples of the alloy include magnesium/silver, magnesium/indium, lithium/aluminum, although not particularly limited thereto. The ratio of the alloying metals is controlled by the temperature of deposition source, atmosphere, and vacuum level and suitably selected. The anode and cathode may be made into two or more layered structure, if needed.

The cathode may be formed by making the above electrode material into a thin film, for example, by a vapor deposition method or a sputtering method.

When the light emitted from the light emitting layer is taken through the cathode, the transmittance of the cathode to the emitted light is preferably higher than 10%. The sheet resistance of the cathode is preferably several hundred Ω/□ or smaller. The thickness of the cathode is generally 10 nm to 1 μm and preferably 50 to 200 nm.

Insulating Layer

Since an electric field is applied to ultra-thin films, pixel defects due to leak and short circuit tend to easily occur. To prevent the defects, a layer made of an insulating thin film layer may be disposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. Mixtures and laminates of these compounds may be also used.

Light Emitting Layer

The light emitting layer has the following functions (1) to (3):

(1) injecting function: function of allowing holes from the anode or the hole injecting layer to be injected to the light emitting layer and allowing electrons from the cathode or the electron injecting layer to be injected to the light emitting layer, when an electric field is applied;

(2) transporting function: function of transporting injected charges (electrons and holes) by the force of the electric field; and (3) light emitting function: function of providing the field for recombination of electrons and holes to allow the emission of light.

The light emitting layer may be different in the hole injection ability and the electron injection ability, and also in the hole transporting ability and the electron transporting ability each being expressed by a hole mobility or an electron mobility, respectively. Preferably, the light emitting layer transports one kind of charges.

The host material and the doping material for use in the light emitting layer are not particularly limited. Examples thereof include a fused polycyclic aromatic compound and its derivative, such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinyl anthracenyl)benzene; an organic metal complex such as tris(8-quinolinolato)aluminum or bis(2-methyl-8-quinolinolato)-4-(phenylphenolinato)aluminum; an arylamine derivative; a styrylamine derivative; a stilbene derivative; a coumarin derivative; a pyran derivative; an oxazone derivative; a benzothiazole derivative; a benzoxazole derivative; a benzimidazole derivative; a pyrazine derivative; a cinnamic ester derivative; a diketopyrrolopyrrole derivative; an acridone derivative; and a quinacridone derivative. Preferred are an arylamine derivative and a styrylamine derivative, with a styrylamine derivative being more preferred.

Hole Injecting Layer/Hole Transporting Layer

The hole injecting layer/hole transporting layer facilitates the injection of holes into a light emitting layer, transports holes into an emission region, and has a large hole mobility and an ionization energy generally as small as 5.7 eV. A material which transports holes to a light emitting layer at a smaller magnitude of electric field is preferably used for the hole injecting layer/hole transporting layer. The hole mobility of the material is preferably $10^{-4}$ cm$^2$/V·s or more when applying an electric field of $10^4$ to $10^6$ V/cm.

As described above, the aromatic amine derivative of the invention is preferably used as a hole injecting layer material, particularly as a hole transporting layer material. The hole transporting layer may be formed from the aromatic amine derivative of the invention alone or in combination with another material which is not particularly limited as long as it has preferred properties mentioned above and can be selected from materials generally used as a hole transporting material in a photoconductive material and known hole transporting materials used in organic EL devices. In the present invention, a material which has a hole transporting ability and can be used in a hole transporting region is called a hole transporting material.

Examples of the material for a hole transporting layer other than the aromatic amine derivative of the invention include a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and a polymeric material, such as polyvinyl carbazole, polysilane, and a conductive polymer, although not particularly limited thereto.

The material for a hole injecting layer is not particularly limited as long as it has preferred properties mentioned above and can be selected from materials generally used as a hole injecting material in a photoconductive material and known hole transporting materials used in organic EL devices. In the present invention, a material which has a hole injecting ability and can be used in a hole injecting region is called a hole injecting material. To enhance the electron injecting ability, an electron-accepting compound may be added to the electron injecting material.

In the organic EL device of the invention, a hexaazatriphenylene compound represented by formula (A) is preferably used as the hole injecting material.

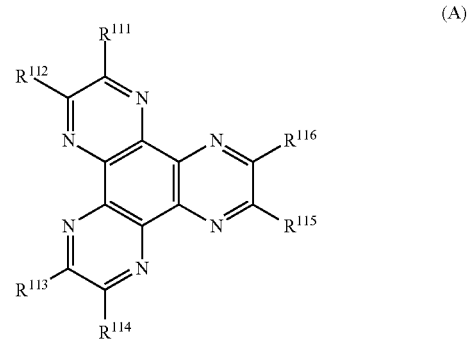

(A)

In formula (A), $R^{111}$ to $R^{116}$ independently represent a cyano group, —CONH$_2$, a carboxyl group, or —COOR$^{117}$ (wherein $R^{117}$ represents an alkyl group having 1 to 20 carbon atoms), or any of $R^{111}$ and $R^{112}$, $R^{113}$ and $R^{114}$, and $R^{115}$ and $R^{116}$ may be boded to each other to represent —CO—O—CO—.

In a preferred embodiment, $R^{111}$ to $R^{116}$ are the same and represent a cyano group, —CONH$_2$, a carboxyl group, or —COOR$^{117}$. In another preferred embodiment, $R^{111}$ and $R^{112}$, $R^{113}$ and $R^{114}$, and $R^{115}$ and $R^{116}$ are all bonded to each other to represent —CO—O—CO—.

Further examples of the hole transporting material usable in the organic EL device of the invention include an aromatic tertiary amine derivative and a phthalocyanine derivative.

Examples of the aromatic tertiary amine derivative include triphenylamine, tritolylamine, tolyldiphenylamine, N,N'-diphenyl-N,N'-(3-methylphenyl)-1,1'-biphenylyl-4,4'-diamine, N,N,N',N'-(4-methylphenyl)-1,1'-phenyl-4,4'-diamine, N,N,N',N'-(4-methylphenyl)-1,1'-biphenylyl-4,4'-diamine, N,N'-diphenyl-N,N'-dinaphthyl-1,1'-biphenylyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or a polymer constituted by a unit derived from the above aromatic tertiary amines, although not particularly limited thereto.

Examples of the phthalocyanine (Pc) derivative include, but not limited to, a phthalocyanine derivative, such as H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, and GaPc—O—GaPc, and a naphthalocyanine derivative.

In addition, the organic EL device of the invention preferably comprises a layer containing the aromatic tertiary amine derivative and/or the phthalocyanine derivative, for example, a hole transporting layer or a hole injecting layer, between a light emitting layer and an anode.

To enhance the electron injecting ability, an electron-accepting compound may be added to the electron injecting material.

Electron Injecting Layer/Electron Transporting Layer

The electron injecting layer/electron transporting layer facilitates the injection of electrons into a light emitting layer, transports electrons to an emission region, and has a large electron mobility. An adhesion improving layer is an electron injecting layer which includes a material having a particularly high adhesion to a cathode.

The emitted light is reflected by an electrode (cathode in this case). It has been known that the emitted light directly passing through an anode and the emitted light passing through the anode after reflected by the electrode interfere with each other. To effectively utilize this interference effect, the thickness of the electron transporting layer is appropriately selected from several nanometers to several micrometers. When the thickness is large, the electron mobility is preferably regulated to 10$^{-5}$ cm$^2$/Vs or more at an electric field of 10$^4$ to 10$^6$ V/cm in order to avoid the increase in voltage.

Examples of the material for use in the electron injecting layer include, but not limited to, fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. To enhance the electron injecting ability, an electron-donating compound may be added to the electron injecting material.

Examples of another effective electron injecting material include a metal complex compound and a nitrogen-containing five-membered ring derivative.

Examples of the metal complex compound include, but not limited to, 8-hydroxyquinolinatolithium, tris(8-hydroxyquinolinato)aluminum, and bis(2-methyl-8-quinolinato)(1-naphtholato)aluminum.

The nitrogen-containing five-membered ring derivative is preferably a derivative of oxazole, thiazole, oxadiazole, thiadiazole, or triazole.

In the present invention, a benzimidazole derivative represented by any of formulae (1) to (3) is preferred as the nitrogen-containing five-membered ring derivative.

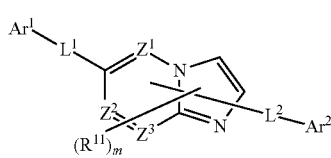

(1)

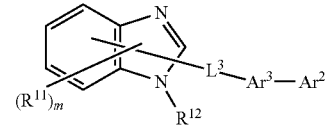

(2)

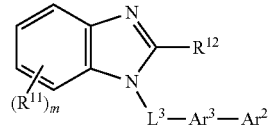

(3)

In formulae (1) to (3), Z$^1$, Z$^2$ and Z$^3$ independently represent a nitrogen atom or a carbon atom.

R$^{11}$ and R$^{12}$ independently represent a substituted or unsubstituted aryl group having 6 to 60 ring carbon atoms, a substituted or unsubstituted heteroaryl group having 3 to 60 ring carbon atoms, an alkyl group having 1 to 20 carbon atoms, a haloalkyl group having 1 to 20 carbon atoms, or an alkoxy group having 1 to 20 carbon atoms.

Subscript m is an integer of 0 to 5. When m is an integer of 2 or more, the groups R$^{11}$ may be the same or different. Two adjacent groups R$^{11}$ may be bonded to each other to form a substituted or unsubstituted aromatic hydrocarbon ring. Examples of the substituted or unsubstituted aromatic hydrocarbon ring include a benzene ring, a naphthalene ring, and an anthracene ring.

Ar$^1$ represents a substituted or unsubstituted aryl group having 6 to 60 ring carbon atoms or a substituted or unsubstituted heteroaryl group having 3 to 60 ring carbon atoms.

Ar$^2$ represents a hydrogen atom, an alkyl group having 1 to 20 carbon atoms, a haloalkyl group having 1 to 20 carbon atoms, an alkoxy group having 1 to 20 carbon atoms, a substituted or unsubstituted aryl group having 6 to 60 ring carbon atoms, or a substituted or unsubstituted heteroaryl group having 3 to 60 ring carbon atoms.

Ar$^3$ represents a substituted or unsubstituted arylene group having 6 to 60 ring carbon atoms or a substituted or unsubstituted heteroarylene group having 3 to 60 ring carbon atoms.

L$^1$, L$^2$ and L$^3$ independently represent a single bond, a substituted or unsubstituted arylene group having 6 to 60 ring carbon atoms, a substituted or unsubstituted fused heterocyclic group having 9 to 60 ring atoms or a substituted or unsubstituted fluorenylene group.

In the organic EL device of the invention, the layer including the aromatic amine derivative of the invention may further include an emission material, a doping material, a hole injecting material or an electron injecting material.

The layer including the aromatic amine derivative of the invention may further include, if necessary, a material which is known as an emission material, a doping material, a hole injecting material, or an electron injecting material, and the aromatic amine derivative may be used as a doping material.

By forming two or more organic thin film layers in an organic EL device, the decrease in the luminance and the lifetime due to the quenching can be prevented. If necessary, an emission material, a doping material, a hole injecting material, and an electron injecting material may be used in combination. The emission luminance and the emission efficiency can be improved and the emission color can be changed by the use of a doping material.

The hole transporting layer of the organic EL device of the invention may be made into two-layered structure, i.e., a first hole transporting layer (anode side) and a second hole transporting layer (cathode side). The aromatic amine derivative of the invention may be used in any of the first hole transporting layer and the second hole transporting layer.

In view of improving the stability to temperature, humidity, and atmosphere, the surface of the organic EL device of the present invention may be provided with a protective layer or the entire device may be protected by silicone oil or a resin.

Each layer of the organic EL device of the invention may be formed by any of a dry film-forming method, such as vacuum deposition, sputtering, plasma, and ion plating, and a wet film-forming method, such as spin coating, dipping, and flow coating.

In a wet film-forming method, the material for each layer is dissolved or dispersed in an appropriate solvent, such as ethanol, chloroform, tetrahydrofuran, and dioxane, and the obtained solution or dispersion is formed into a thin film. The solution and dispersion may contain a resin or an additive to improve the film-forming property and prevent a pin hole in the layer. Examples of the resin include insulating resins, such as polystyrene, polycarbonate, polyarylate, polyester, polyamide, polyurethane, polysulfone, polymethyl methacrylate, polymethyl acrylate, cellulose, and copolymers thereof; photoconductive resins, such as poly-N-vinylcarbazole and polysilane; and conductive resins, such as polythiophene and polypyrrole. Examples of the additive include an antioxidant, an ultraviolet absorber, and a plasticizer.

The thickness of each layer is not particularly limited and selected so as to obtain a good device performance. An excessively large thickness increases the applied voltage sufficient for obtaining a certain level of optical output, resulting in a poor efficiency. An excessively small thickness causes a pin hole, so a sufficient emission luminance cannot be obtained even when an electric field is applied. The thickness is preferably 5 nm to 10 μm and preferably 10 nm to 0.2 μm.

EXAMPLES

The present invention will be described below in more detail with reference to the examples. However, it should be noted that the scope of the invention is not limited thereto.

Intermediate Synthesis 1-1

Synthesis of Intermediate 1-1

Under an argon atmosphere, 750 ml of dry toluene was added to a mixture of 50.8 g (150.0 mmol) of 2-bromotriphenylene, 25.4 g (150.0 mmol) of diphenylamine, and 28.8 g (300.0 mmol) of t-butoxysodium, and the resultant mixture was stirred. After further adding 674 mg (3.0 mmol) of palladium acetate and 607 mg (3.0 mmol) of tri-t-butylphosphine, the mixture was allowed to react at 80° C. for 8 h.

After cooling, the reaction mixture was filtered through celite/silica gel. The filtrate was concentrated under reduced pressure. The obtained residue was recrystallized from toluene and the crystal was collected by filtration and dried to obtain 48.3 g of a white solid, which was identified as the intermediate 1-1 by FD-MS analysis (Field Desorption Mass Spectrometry Analysis) (yield: 82%).

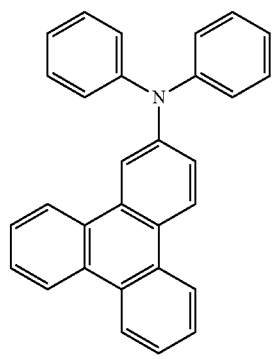

Intermediate 1-1

Intermediate Synthesis 1-2

Synthesis of Intermediate 1-2

Under an argon atmosphere, 500 ml of toluene and 300 ml of ethyl acetate were added to 20.0 g (50.6 mmol) of the intermediate 1-1, and the resultant mixture was stirred. After adding 18.0 g (101.2 mmol) of N-bromosuccinimide, the mixture was allowed to react at room temperature for 24 h. After further adding 1.0 g (5.6 mmol) of N-bromosuccinimide, the reaction was continued at room temperature for 3 h.

After adding 300 ml of water, the reaction mixture was extracted with toluene. The organic layer was washed with a saturated saline, dried over MgSO$_4$, filtrate, and concentrated. The obtained residue was recrystallized from toluene and the crystal was collected by filtration and dried to obtain 24.4 g of a white solid, which was identified as the intermediate 1-2 by FD-MS analysis (yield: 87%).

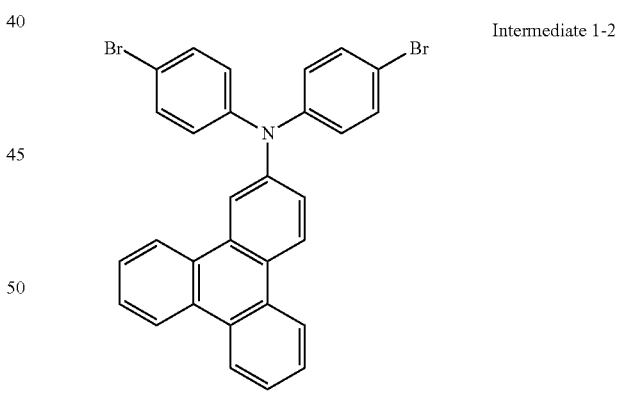

Intermediate 1-2

Intermediate Synthesis 1-3

Synthesis of Intermediate 1-3

Under an argon atmosphere, 500 ml of toluene, 300 ml of dimethoxyethane, and 160 ml (320.0 mmol) of a 2 M aqueous solution of Na$_2$CO$_3$ were added to a mixture of 49.1 g (160.0 mmol) of 2-bromotriphenylene, 25.0 g (160.0 mmol) of 4-chlorophenylboronic acid, and 3.7 g (3.20 mmol) of Pd[PPh$_3$]$_4$, and the resultant mixture was stirred for 30 h while refluxing under heating.

After the reaction, the obtained mixture was cooled to room temperature and extracted with dichloromethane in a separatory funnel. The organic layer was dried over MgSO$_4$, and then filtered and concentrated. The obtained residue was recrystallized from toluene and the crystal was collected by filtration and dried to obtain 49.0 g of a white solid, which was identified as the intermediate 1-3 by FD-MS analysis (yield: 90%).

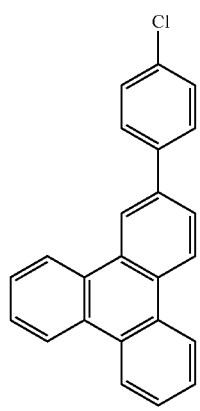

Intermediate 1-3

Intermediate Synthesis 1-4

Synthesis of Intermediate 1-4

In the same manner as in Intermediate Synthesis 1-1 except for using 30.0 g of the intermediate 1-3 in place of 2-bromotriphenylene, 30.0 g of a white solid was obtained, which was identified as the intermediate 1-4 by FD-MS analysis (yield: 71%).

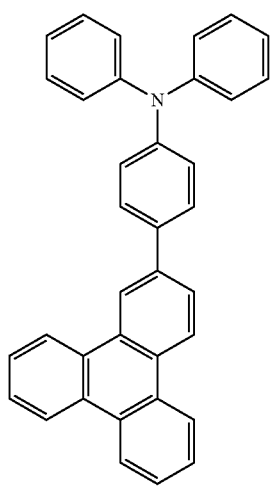

Intermediate 1-4

Intermediate Synthesis 1-5

Synthesis of Intermediate 1-5

In the same manner as in Intermediate Synthesis 1-2 except for using 30.0 g of the intermediate 1-4 in place of the intermediate 1-1, 25.4 g of a white solid was obtained, which was identified as the intermediate 1-5 by FD-MS analysis (yield: 63%).

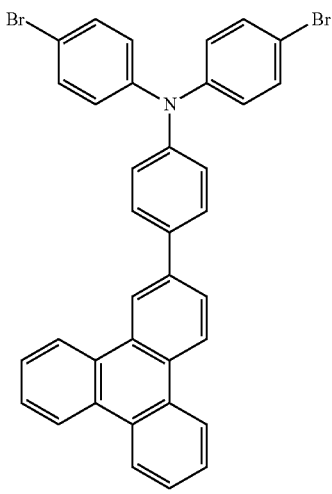

Intermediate 1-5

Intermediate Synthesis 2-1

Synthesis of Intermediate 2-1

Under an argon atmosphere, 150 ml of toluene, 150 ml of dimethoxyethane, and 150 ml (300.0 mmol) of a 2 M aqueous solution of Na$_2$CO$_3$ were added to a mixture of 28.3 g (100.0 mmol) of 4-iodobromobenzene, 22.3 g (105.0 mmol) of dibenzofuran-4-boronic acid, and 2.31 g (2.00 mmol) of Pd[PPh$_3$]$_4$, and the resultant mixture was stirred for 10 h while refluxing under heating.

After the reaction, the obtained mixture was cooled to room temperature and extracted with dichloromethane in a separatory funnel. The organic layer was dried over MgSO$_4$, and then filtered and concentrated. The concentrate was purified by silica gel column chromatography to obtain 26.2 g of a white solid, which was identified as the intermediate 2-1 by FD-MS analysis (yield: 81%).

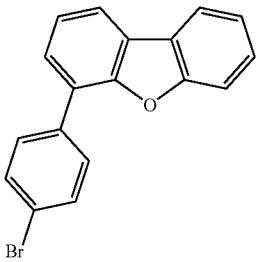

Intermediate 2-1

Intermediate Synthesis 2-2

Synthesis of Intermediate 2-2

Under an argon atmosphere, 450 ml of toluene, 100 ml of dimethoxyethane, and 110 ml (220.0 mmol) of a 2 M aqueous solution of Na$_2$CO$_3$ were added to a mixture of 24.0 g (112.0 mmol) of 4'-bromoacetanilide, 28.6 g (135.0 mmol) of dibenzofuran-4-boronic acid, and 2.6 g (2.24 mmol) of Pd[PPh$_3$]$_4$, and the resultant mixture was stirred for 10 h while refluxing under heating.

After the reaction, the obtained mixture was cooled to room temperature, and the precipitated crystal was collected by filtration. The collected crystal was dissolved in tetrahydrofuran and filtered through celite/silica gel. The filtrate was concentrated under reduced pressure. The obtained residue was washed with methanol/hexane and dried to obtain 18.0 g of a white solid, which was identified as the intermediate 2-2 by FD-MS analysis (yield: 53%).

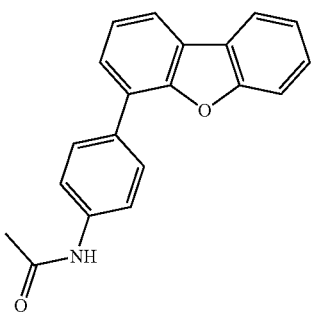

Intermediate 2-2

Intermediate Synthesis 2-3

Synthesis of Intermediate 2-3

A mixture obtained by adding 120 ml of xylene, 1200 ml of water, and 60 ml of ethanol to 18.0 g (59.7 mmol) of the intermediate 2-2 was stirred. After further adding 20.0 g (360.0 mmol) of potassium hydroxide, the resultant mixture was stirred for 10 h while refluxing under heating.

After the reaction, the obtained mixture was cooled to room temperature and extracted with toluene in a separatory funnel. The organic layer was dried over MgSO$_4$, and then filtered and concentrated. The obtained residue was recrystallized from xylene. The crystal was collected by filtration and dried to obtain 14.7 g of a white solid, which was identified as the intermediate 2-3 by FD-MS analysis (yield: 95%).

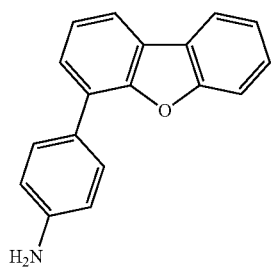

Intermediate 2-3

Intermediate Synthesis 2-4

Synthesis of Intermediate 2-4

Under a nitrogen atmosphere, 1000 ml of acetic acid was added to 150 g (0.89 mol) of dibenzofuran, and dissolved under heating. After further adding 188 g (1.18 mol) of bromine dropwise, the mixture was stirred at room temperature for 20 h. The precipitated crystal was collected by filtration and washed successively with acetic acid and water. The obtained crude product was recrystallized from methanol several times to obtain 66.8 g of a white crystal, which was identified as the intermediate 2-4 by FD-MS analysis (yield: 30%).

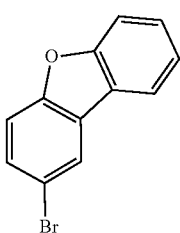

Intermediate 2-4

Intermediate Synthesis 2-5

Synthesis of Intermediate 2-5

Under an argon atmosphere, to 24.7 g (100.0 mmol) of the intermediate 2-4, 400 ml of dry tetrahydrofuran was added, and the mixture was cooled to −40° C. Then, 63 ml (100.0 mmol) of a 1.6 M hexane solution of n-butyllithium was gradually added. The reaction solution was stirred for one hour while heating to 0° C. Then, the reaction solution was cooled again to −78° C., to which a solution of 26.0 g (250.0 mmol) of trimethyl borate in 50 ml of dry tetrahydrofuran was added dropwise. After the dropwise addition, the reaction solution was stirred at room temperature for 5 h. After adding 200 ml of a 1 N hydrochloric acid, the solution was stirred for one hour and then the aqueous layer was removed. The organic layer was dried over MgSO$_4$, and the solvent was evaporated off under reduced pressure. The obtained solid was washed with toluene to obtain 15.2 g of a white crystal (yield: 72%).

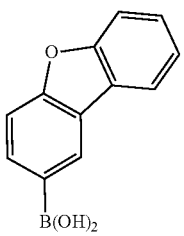

Intermediate 2-5

Intermediate Synthesis 2-6

Synthesis of Intermediate 2-6

Under an argon atmosphere, 150 ml of toluene, 150 ml of dimethoxyethane, and 150 ml (300.0 mmol) of a 2 M aqueous solution of Na$_2$CO$_3$ were added to a mixture of 28.3 g (100.0 mmol) of 4-iodobromobenzene, 22.3 g (105.0 mmol) of the intermediate 2-5, and 2.31 g (2.00 mmol) of Pd[PPh$_3$]$_4$, and the resultant mixture was stirred for 10 h while refluxing under heating.

After the reaction, the obtained mixture was extracted with dichloromethane in a separatory funnel. The organic layer was dried over MgSO₄, and then filtered and concentrated. The concentrate was purified by silica gel column chromatography to obtain 24.2 g of a white solid, which was identified as the intermediate 2-6 by FD-MS analysis (yield: 75%).

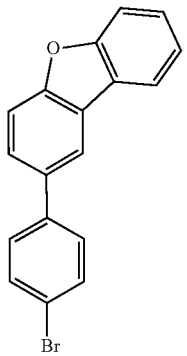

Intermediate 2-6

Intermediate Synthesis 2-7

Synthesis of Intermediate 2-7

In the same manner as in Intermediate Synthesis 2-5 except for using 26.3 g of 2-bromodibenzothiophene in place of the intermediate 2-4, 14.8 g of a white solid was obtained, which was identified as the intermediate 2-7 by FD-MS analysis (yield: 65%).

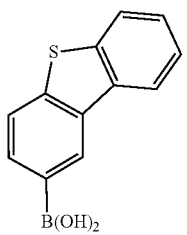

Intermediate 2-7

Intermediate Synthesis 2-8

Synthesis of Intermediate 2-8

Under an argon atmosphere, 250 ml of dry toluene was added to a mixture of 16.9 g (50.0 mmol) of 2-bromotriphenylene, 13.0 g (50.0 mmol) of the intermediate 2-3, and 9.6 g (100.0 mmol) of t-butoxysodium, and the resultant mixture was stirred. After adding 225 mg (1.0 mmol) of palladium acetate and 202 mg (1.0 mmol) of tri-t-butylphosphine, the reaction was allowed to proceed at 80° C. for 8 h.

After cooling, the reaction mixture was filtered through celite/silica gel. The filtrate was concentrated under reduced pressure. The obtained residue was recrystallized from toluene and the crystal was collected by filtration and dried to obtain 19.9 g of a white solid, which was identified as the intermediate 2-8 by FD-MS analysis (yield: 82%).

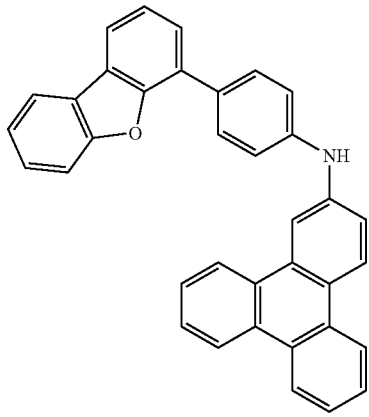

Intermediate 2-8

Synthesis Example 1

Production of Aromatic Amine Derivative H1

Under an argon atmosphere, 50 ml of toluene, 25 ml of dimethoxyethane, and 23 ml (46.0 mmol) of a 2 M aqueous solution of Na₂CO₃ were added to a mixture of 8.3 g (15.0 mmol) of the intermediate 1-2, 7.0 g (33.0 mmol) of dibenzofuran-4-boronic acid, and 0.87 g (0.75 mmol) of Pd[PPh₃]4, and the resultant mixture was stirred for 10 h while refluxing under heating.

After the reaction, the obtained mixture was extracted with toluene in a separatory funnel. The organic layer was dried over MgSO₄, and then filtered and concentrated. The concentrate was purified by silica gel column chromatography. The crude product was recrystallized from toluene and the crystal collected by filtration was dried to obtain 7.9 g of a white solid, which was identified as the aromatic amine derivative H1 by FD-MS analysis (yield: 72%).

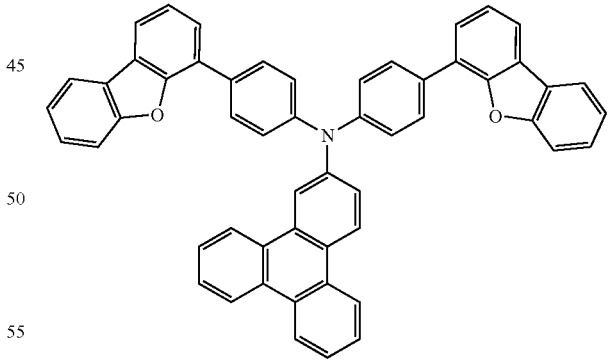

H1

Synthesis Example 2

Production of Aromatic Heterocyclic Derivative H2

In the same manner as in Synthesis Example 1 except for using 7.0 g of the intermediate 2-5 in place of dibenzofuran-4-boronic acid, 6.9 g of a white crystal was obtained, which was identified as the aromatic amine derivative H2 by FD-MS analysis (yield: 63%).

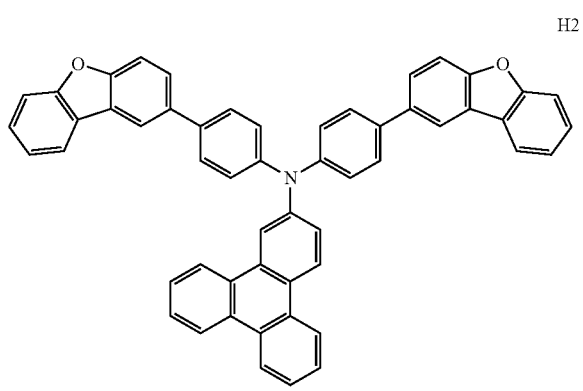 [SMILES: c1ccc2c(c1)oc1ccc(-c3ccc(N(c4ccc(-c5ccc6oc7ccccc7c6c5)cc4)c4ccc5c6ccccc6c6ccccc6c5c4)cc3)cc12]

Synthesis Example 3

Production of Aromatic Heterocyclic Derivative H3

In the same manner as in Synthesis Example 1 except for using 6.8 g of the intermediate 2-7 in place of dibenzofuran-4-boronic acid, 3.4 g of a white crystal was obtained, which was identified as the aromatic amine derivative H3 by FD-MS analysis (yield: 33%).

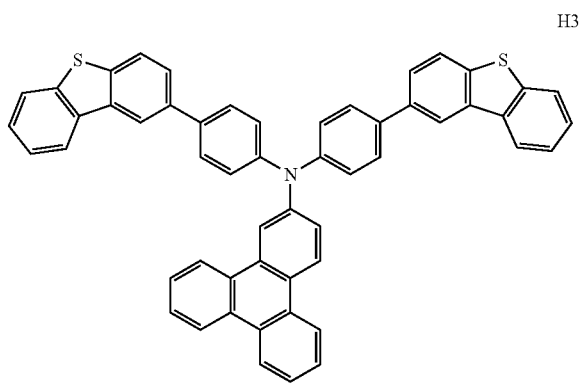 [SMILES: c1ccc2c(c1)sc1ccc(-c3ccc(N(c4ccc(-c5ccc6sc7ccccc7c6c5)cc4)c4ccc5c6ccccc6c6ccccc6c5c4)cc3)cc12]

Synthesis Example 4

Production of Aromatic Heterocyclic Derivative H4

Under an argon atmosphere, 50 ml of dry xylene was added to a mixture of 3.2 g (10.0 mmol) of the intermediate 2-6, 4.9 g (10.0 mmol) of the intermediate 2-8, 0.14 g (0.15 mmol) of $Pd_2(dba)_3$, 0.087 g (0.3 mmol) of $P(tBu)_3HBF_4$, and 1.9 g (20.0 mmol) of t-butoxysodium, and the resultant mixture was refluxed for 8 h under heating.

After the reaction, the reaction liquid was cooled to 50° C. and filtered through celite and silica gel. The filtrate was concentrated and the obtained concentrate was purified by silica gel column chromatography to obtain a white solid. The crude product was recrystallized from toluene to obtain 3.6 g of a white crystal, which was identified as the aromatic heterocyclic derivative H4 by FD-MS analysis (yield: 50%).

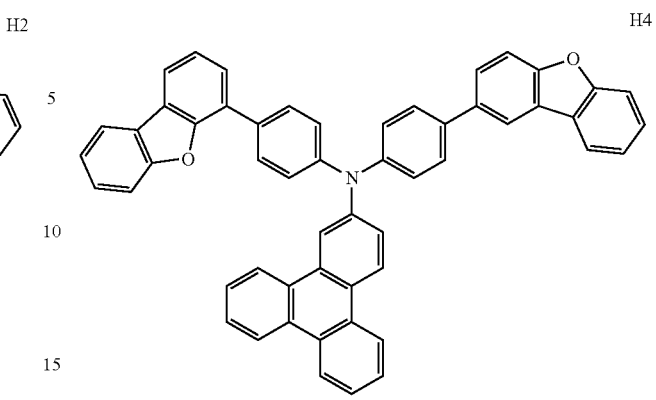

Synthesis Example 5

Production of Aromatic Heterocyclic Derivative H5

In the same manner as in Synthesis Example 4 except for using 3.1 g of 4-bromoterphenyl in place of the intermediate 2-6, 3.9 g of a white crystal was obtained, which was identified as the aromatic amine derivative H5 by FD-MS analysis (yield: 55%).

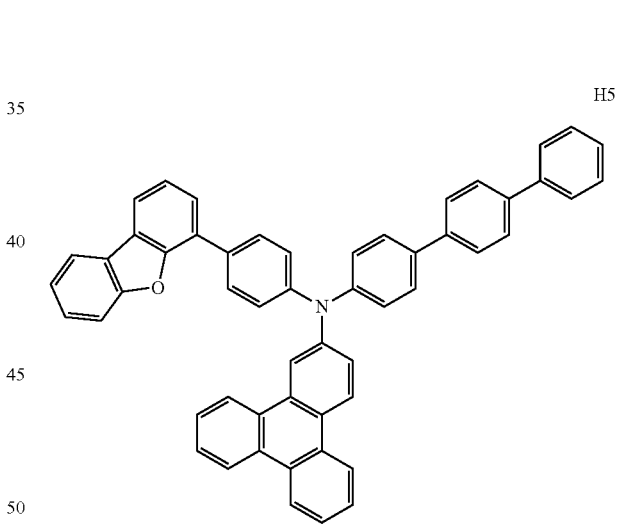

Synthesis Example 6

Production of Aromatic Heterocyclic Derivative H6

In the same manner as in Synthesis Example 4 except for using 2.7 g 2-bromo-9,9-dimethylfluorene in place of the intermediate 2-6, 3.5 g of a white crystal was obtained, which was identified as the aromatic amine derivative H6 by FD-MS analysis (yield: 52%).

111

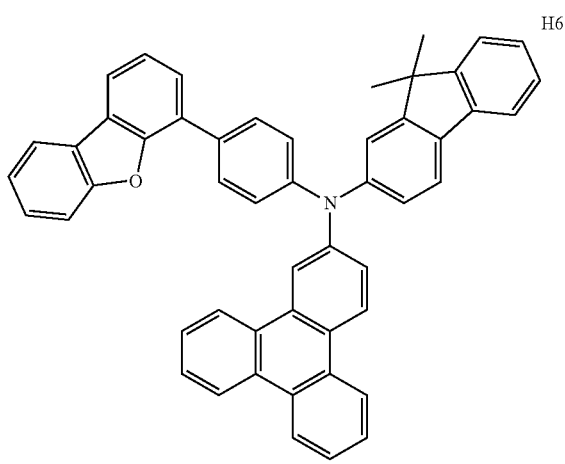 [SMILES: CC1(C)c2ccccc2-c2ccc(N(c3ccc(-c4cccc5c4oc4ccccc45)cc3)c3ccc4c5ccccc5c5ccccc5c4c3)cc21]

H6

Synthesis Example 7

Production of Aromatic Heterocyclic Derivative H7

In the same manner as in Synthesis Example 1 except for using 9.4 g of the intermediate 1-5 in place of the intermediate 1-2, 4.1 g of a white crystal was obtained, which was identified as the aromatic amine derivative H7 by FD-MS analysis (yield: 32%).

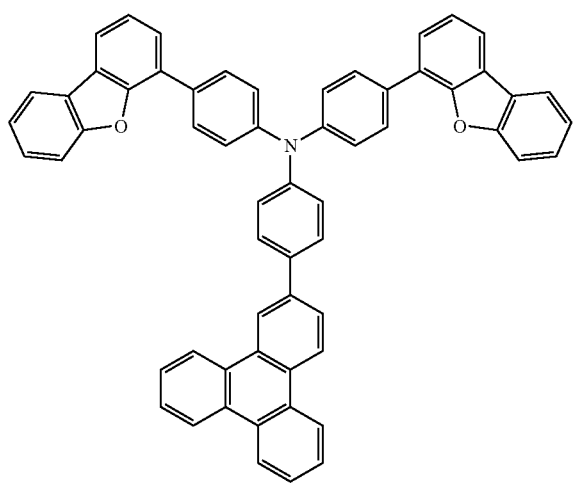

H7

Synthesis Example 8

Production of Aromatic Heterocyclic Derivative H8

In the same manner as in Synthesis Example 1 except for using 6.8 g of dibenzothiophene-4-boronic acid in place of dibenzofuran-4-boronic acid, 3.0 g of a white crystal was obtained, which was identified as the aromatic amine derivative H8 by FD-MS analysis (yield: 26%).

112

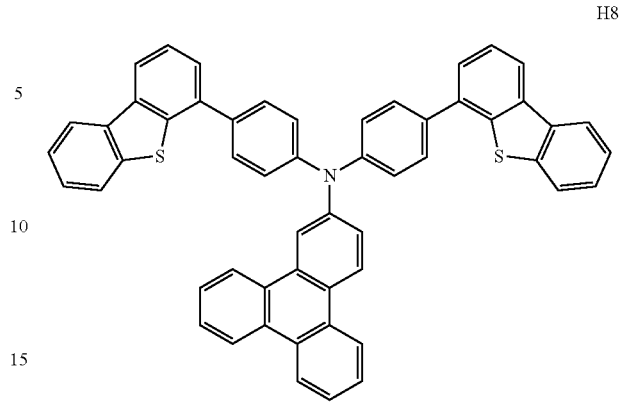

H8

Example 1

Production of Organic EL Device

A glass substrate with an ITO transparent electrode line having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following electron-accepting compound A was vapor-deposited onto the surface on the side where the transparent electrode line was formed so as to cover the transparent electrode, thereby forming a film A having a thickness of 5 nm.

On the film A, the following aromatic amine derivative TPTE as a first hole transporting material was vapor-deposited to form a first hole transporting layer having a thickness of 65 nm.

Successively after the formation of the first hole transporting layer, the aromatic amine derivative H1 as a second hole transporting material was vapor-deposited to form a second hole transporting layer having a thickness of 10 nm.

On the hole transporting layer, the compound host1-X as a first host material, the compound host2-X as a second host material, and Ir(bzq)$_3$ as a phosphorescent dopant material were co-deposited, thereby forming a green-emitting light emitting layer having a thickness of 25 nm. The concentration of the phosphorescent dopant material was 10% by mass, the concentration of the first host material was 45% by mass, and the concentration of the second host material was 45% by mass.

Next, on the phosphorescent light emitting layer, a film of the compound C having a thickness of 35 nm, a LiF film having a thickness of 1 nm, and a metallic Al film having a thickness of 80 nm were successively deposited to form an cathode. The electron injecting electrode LiF was formed at a film-forming speed of 1 Å/min.

(A)

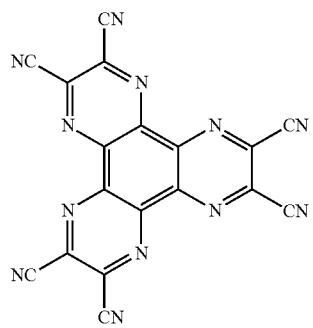

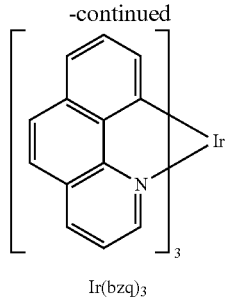

Ir(bzq)₃

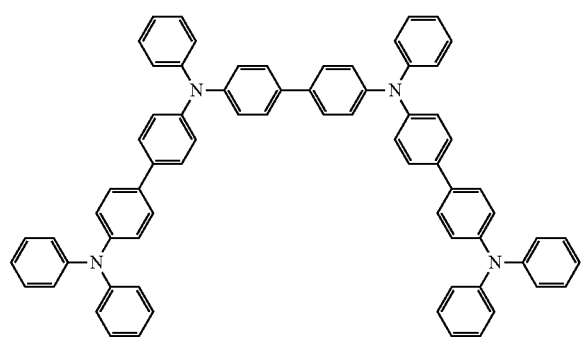

(TPTE)

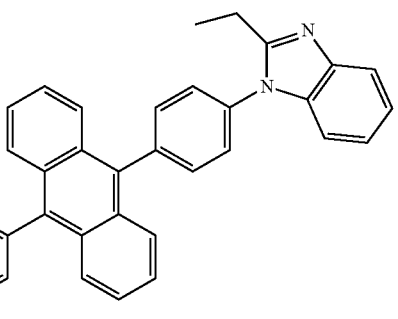

(C)

(host1-X)

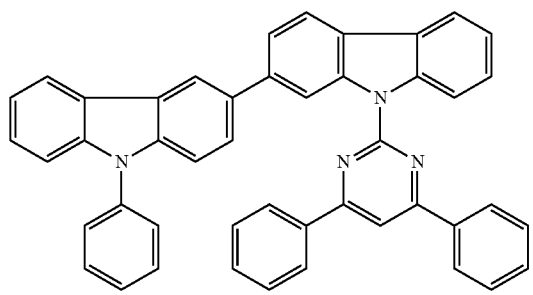

Examples 2 to 8

Production of Organic EL Device

Each organic EL device of Examples 2 to 8 was produced in the same manner as in Example 1 except for using each aromatic amine derivative listed in Table 1 as the second hole transporting material.

Comparative Examples 1 and 2

Production of organic EL device

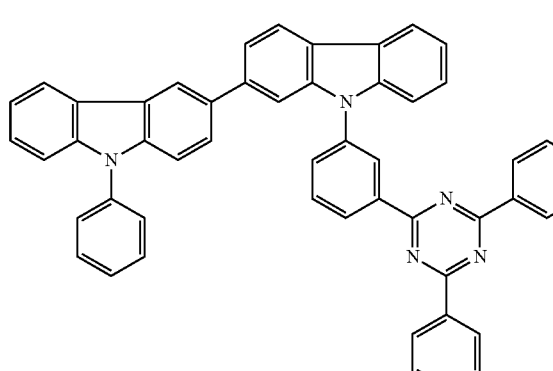

(host2-X)

Each organic EL device of Comparative Examples 1 and 2 was produced in the same manner as in Example 1 except for using each of the following comparative compounds 1 and 2 as the second hole transporting material. The comparative compound 1 is described in Patent Document 6 (paragraph 104).

Comparative compound 1

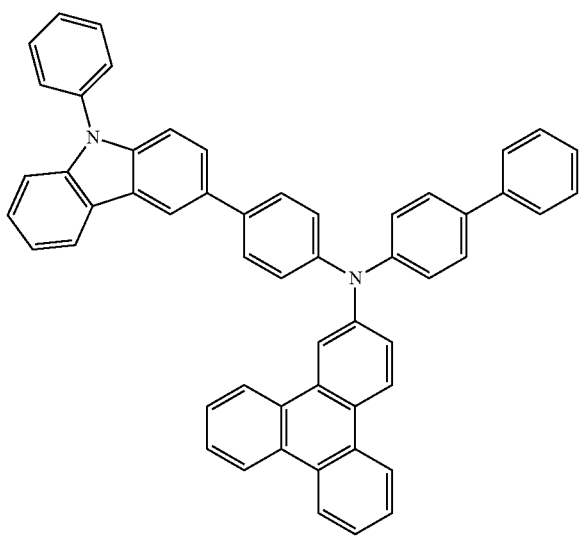

Comparative compound 2

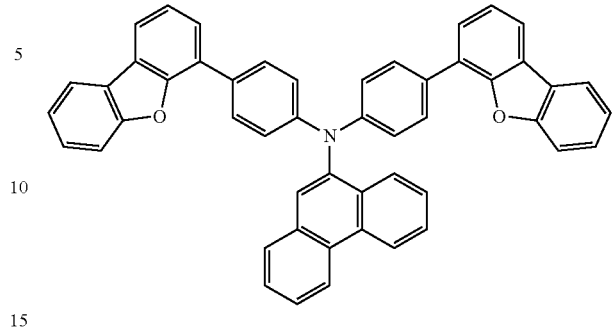

Evaluation of Emission Performance of Organic EL Device

Each organic EL device thus produced was measured for the luminance (L) and the current density by allowing the device to emit light under a direct current drive. Using the measured results, the current efficiency (L/J) and the driving voltage (V) at a current density of 10 mA/cm$^2$ were determined. In addition, the organic EL device was measured for the lifetime at a current density of 50 mA/cm$^2$. The 80% lifetime is the time taken until the luminance was reduced to 80% of the initial luminance when driving the device at constant current. The results are shown in Table 1.

TABLE 1

| | First hole transporting material | Second hole transporting material | Emission efficiency (cd/A) @10 mA/cm$^2$ | Driving voltage (V) @10 mA/cm$^2$ | 80% Lifetime (h) |
|---|---|---|---|---|---|
| Examples | | | | | |
| 1 | TPTE | H1 | 60.7 | 3.1 | 400 |
| 2 | TPTE | H2 | 61.5 | 3.1 | 370 |
| 3 | TPTE | H3 | 61.2 | 3.1 | 350 |
| 4 | TPTE | H4 | 62.2 | 3.1 | 400 |
| 5 | TPTE | H5 | 59.5 | 3.1 | 400 |
| 6 | TPTE | H6 | 60.5 | 3.0 | 350 |
| 7 | TPTE | H7 | 60.5 | 3.2 | 380 |
| 8 | TPTE | H8 | 60.8 | 3.1 | 390 |
| Comparative Examples | | | | | |
| 1 | TPTE | comparative compound 1 | 57.6 | 3.0 | 380 |
| 2 | TPTE | comparative compound 2 | 60.5 | 3.5 | 220 |

The results of Table 1 show that an organic EL device having a high efficiency even when driving it at a low voltage and having a long lifetime is obtained by using the aromatic amine derivative of the invention.

What is claimed is:

1. An organic electroluminescence device comprising an anode, a cathode, and at least one organic thin film layers between the anode and the cathode, wherein:

the at least one organic thin film layers comprises a light emitting layer and a hole transporting layer between the anode and the light emitting layer;

the hole transporting layer comprises an anode side first hole transporting layer and a cathode side second hole transporting layer; and any of the anode side first hole transporting layer and the cathode side second hole transporting layer comprise an aromatic amine derivative represented by formula (1):

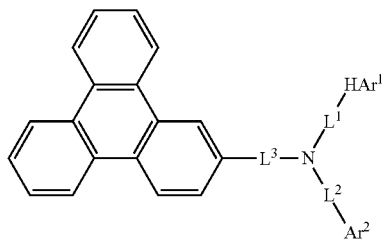
(1)

wherein HAr¹ represents a group selected from formulae (2) to (4):

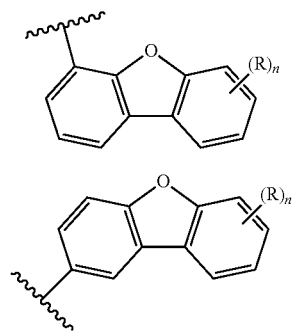
(2)

(4)

in formulae (2) to (4), n represents an integer of 0 to 4; and each R independently represents a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, when more than one R is present, the groups R may be the same or different;

$L^1$ to $L^2$ may be the same or different and each independently represents a group represented by formula (6):

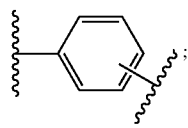
(6)

and
$L^3$ represents a single bond;
$Ar^2$ represents a group selected from formulae (8) and (10), provided that $Ar^2$ does not include a carbazole and a substitited or unsubstituted animo group:

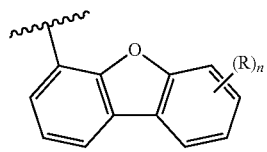
(8)

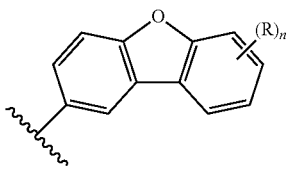
(10)

in formulae (8) to (11), n represents an integer of 0 to 4; and each R independently represents a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group, when more than one R is present, the groups R may be the same or different.

2. The organic electroluminescence according to claim 1, wherein the aromatic amine derivative is represented by formula (12):

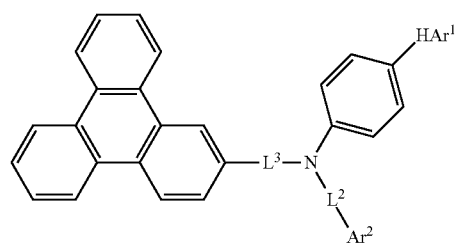
(12)

wherein HAr¹, Ar², L², and L³ are as defined in formula (1).

3. The organic electroluminescence device according to claim 1, wherein HAr1 does not include a carbazole skeleton and a substituted or unsubstituted amino group.

4. The organic electroluminescence device according to claim 1, wherein n in formulae (2) and (4) is 0.

5. The organic electroluminescence device according to claim 1, wherein n in formulae (8) and (10) is 0.

6. The organic electroluminescence device according to claim 2, wherein HAr¹ does not include a carbazole skeleton and a substituted or unsubstituted amino group.

7. The organic electroluminescence device according to claim 2, wherein n in formulae (2) and (4) is 0.

8. The organic electroluminescence device according to claim 2, wherein n in formulae (8) and (10) is 0.

9. The organic electroluminescence device according to claim 1, wherein the cathode side second hole transporting layer comprises the aromatic amine derivative.

10. The organic electroluminescence device according to claim 1, wherein the organic electroluminescence device comprises a hole injecting layer between the anode and the anode side first hole transporting layer.

11. The organic electroluminescence device according to claim 1, wherein each of $L^1$ and $L^2$ is a p-phenylene group.

12. The organic electroluminescence device according to claim 2, wherein $L^2$ is a p-phenylene group.

13. The organic electroluminescence device according to claim 1, wherein one of $HAr^1$ and $Ar^2$ is a 4-dibenzofuranyl group.

14. The organic electroluminescence device according to claim 1, wherein one of $HAr^1$ and $Ar^2$ is a 2-dibenzofuranyl group.

15. The organic electroluminescence device according to claim 1, wherein $HAr^1$ and $Ar^2$ are both 4-dibenzofuranyl groups.

16. The organic electroluminescence device according to claim 1, wherein $HAr^1$ and $Ar^2$ are both 2-dibenzofuranyl groups.

* * * * *